US008795681B2

(12) United States Patent
Wu et al.

(10) Patent No.: US 8,795,681 B2
(45) Date of Patent: Aug. 5, 2014

(54) RACCOON POXVIRUS EXPRESSING RABIES GLYCOPROTEINS

(75) Inventors: Stephen Qitu Wu, Fort Dodge, IA (US); Michael A. Gill, Fort Dodge, IA (US); Hsien-Jue Chu, Bonner Springs, KS (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 1262 days.

(21) Appl. No.: 12/128,296

(22) Filed: May 28, 2008

(65) Prior Publication Data

US 2009/0010963 A1    Jan. 8, 2009

Related U.S. Application Data

(60) Provisional application No. 60/932,492, filed on May 30, 2007.

(51) Int. Cl.
*A61K 39/205* (2006.01)
*A61K 39/275* (2006.01)
*A61K 39/295* (2006.01)
*A61K 39/116* (2006.01)
*C12N 7/01* (2006.01)
*C12N 15/863* (2006.01)

(52) U.S. Cl.
USPC ............... 424/199.1; 435/235.1; 435/239; 435/471; 435/320.1; 424/224.1; 424/201.1

(58) Field of Classification Search
None
See application file for complete search history.

(56) References Cited

U.S. PATENT DOCUMENTS

| | | | |
|---|---|---|---|
| 5,047,238 A | 9/1991 | Acree | |
| 5,266,313 A | 11/1993 | Esposito | |
| 5,348,741 A | 9/1994 | Esposito | |
| 6,024,953 A | 2/2000 | Lathe | |
| 6,106,841 A | 8/2000 | Osorio | |
| 6,183,750 B1 | 2/2001 | Paoletti | |
| 6,241,989 B1 * | 6/2001 | Scott et al. | 424/199.1 |
| 6,294,176 B1 | 9/2001 | Cochran | |
| 6,673,601 B1 | 1/2004 | Jacob | |
| 6,713,068 B1 * | 3/2004 | Audonnet et al. | 424/206.1 |
| 6,719,981 B1 | 4/2004 | Mebatsion | |
| 6,962,810 B2 | 11/2005 | Fraser | |
| 7,045,313 B1 | 5/2006 | Moss | |
| 7,067,248 B2 | 6/2006 | Hruby | |
| 7,074,413 B2 | 7/2006 | Dietzschold | |
| 7,087,234 B1 * | 8/2006 | Scott et al. | 424/199.1 |
| 7,208,313 B2 | 4/2007 | McCart | |
| 2005/0282210 A1 | 12/2005 | Maki | |

FOREIGN PATENT DOCUMENTS

WO    WO 03/097846    * 11/2003    ......... C12N 15/863

OTHER PUBLICATIONS

Hu, et al. Raccoon poxvirus live recombinant feline panleukopenia virus (FPV) VP2 and rabies virus glycoprotein bivalent vaccine. Vaccine. 1997; 15(12113): 1466-1472.*
Giavedoni, et al. A vaccinia virus double recombinant expressing the F and H genes of Rinderpest virus protects cattle against Rinderpest and causes no pock lesions. Proc. Natl. Acad. Sci. USA. 1991; 88: 8011-8015.*
Bennett, et al. Recombinant Vaccinia Viruses Protect Against Clostridium perfringens α-Toxin. Viral Immunol. 1999; 12(2): 97-105.*
Real et al. Journal of Heredity 96(3): 253-260, 2005.*
Dietzschold et al. Reviews of Infectious Diseases 10 (supplement 4): S785-S798, 1988.*
Martinez et al. Archivos de Medicina Veterinaria 31(1): [no page numbers] 1999.*
Thomas et al, Archives of Virology 49:217-227, 1975.*
Sekhar Chakrabarti et al.; Compact, Synthetic, Vaccinia Virus Early/ Late Promoter for Protein Expression; BioTechniques; vol. 23; pp. 1094-1097; 1997.
A.D. Alexander et al.; Survey of Wild Mammals in a Chesapeake Bay Area for Selected Zoonoses; J. Wildlife Diseases; vol. 8; pp. 119-126; 1972.
Chokri Bahloul et al; DNA-Based Immunization for Exploring the Enlargement of Immunological Cross-Reactivity Against the Lyssaviruses; Vaccine; vol. 16 (4); pp. 417-425; 1998.
J. C. Demartini e .; Raccoon Poxvirus Rabies Virus Glycoprotein Recombinant Vaccine in Sheep; Arch Virology; vol. 133; pp. 211-222; 1993.
Bernard Dietzschold et al.; Rhabdoviruses; Fields Virology; $3^{rd}$ Ed., pp. 1137-1159; 1996.
Joseph Esposito et al.; Vaccinia Virus Recombinants Expressing Rabies Virus Glycoprotein Protect Against Rabies; Virus Genes; Vol, 1; pp. 7-21; 1987.

(Continued)

*Primary Examiner* — Mary E Mosher
(74) *Attorney, Agent, or Firm* — Michael P. Morris; Joyce L. Morrison

(57) ABSTRACT

The present invention relates to recombinant raccoon poxvirus vectors that express the rabies virus glycoprotein gene at the hemagglutinin (ha) locus of the poxvirus genome or express the glycoprotein gene of the same or different rabies strains at the thymidine kinase (tk) and the hemagglutinin (ha) loci of the poxvirus genome, and their use as adjuvant-free vaccines. The raccoon poxvirus vector comprises the nucleic acid molecules encoding the glycoprotein of a Challenge Virus Standard rabies strain inserted and expressed at the tk locus of the poxvirus genome and of a Pasteur-Paris rabies strain inserted and expressed at the ha locus of the poxvirus genome. The vaccine may optionally contain a mixture of additional feline and canine antigens for immunization of animals. Also disclosed are methods for inducing an immune response to rabies in a mammal by administering to the mammal an effective immunizing amount of the vaccine of the invention.

28 Claims, 23 Drawing Sheets

(56) References Cited

OTHER PUBLICATIONS

Jooeph Esposito et al.; Successful Oral Rabies Vaccination of Raccoons With Raccoon Poxvirus Recombinants Expressing Rabies Virus Glycoprotein; Virology; vol. 165; pp. 313-316; 1988.

J. Esposito; Live Poxvirus-Vectored Vaccines in Wildlife Immunization Programmes: The Rabies Paradigm; Research in Virology;vol. 140; pp. 480-482; 1989.

Joseph Esposito et al.; Oral Immunization of Animals With Raccoon Poxvirus Expressing Rabies Virus Glycoprotein; Vaccine 89 eds.; Cold Spring Harbor Laboratory Press; Cold Spring, NY; pp. 403-408; 1989.

Joseph Esposito et al.; Raccoon Poxvirus Rabies—Glycoprotein Recombinant Oral Vaccine for Wildlife: Further Efficiacy and SFETY Studies and Serosurvey for Poxvirus; Vaccines 92; Cold Spring Harbor Laboratory Pess; pp. 321-329; 1992.

Y. F. Herman; Isolation and Characterization of a Naturally Occurring Pox Virus of Raccoons; 64$^{th}$ Annual Meeting of the ASM; pp. 117; 1964.

Liangbiao Hu et al.; Raccoon Poxvirus Live Recombinant Feline Panleukopenia Virus VP2 and Rabies Virus Glycoprotein Bivalent Vaccine; Vaccine; vol. 15; pp. 1466-1472; 1997.

Liangbiao Hu et al.; Raccoon Poxvirus Feline Panleukopenia Virus VP2 Recombinant Protects Cats Against FPV Challenge; Virology; vol. 218; pp. 248-252;1996.

Roderick MacFarlan et al.; Molecular Immunology; vol. 23(7); pp. 733-741; 1986.

Jorge E. Osorio et al; Recombinant Raccoon Pox Vaccine Protects Mice Against Lethal Plague; Vaccine; vol. 21; pp. 1232-1238; 2003.

Pierre Perrin et al; Rabies Immunosome (Subunit Vaccine) Structure and Immunogenicity. Pre- and Post-Exposure Protection Studies; Vaccine; vol. 3, pp. 325-332; 1985.

Stephen J. Spatz; Immunological Characterization of the Feline Herpesvirus-1 Glycoprotein B and Analysis of Its Deduced Amino Acid Sequence; Virology; vol. 197; pp. 125-136; 1993.

Stephen J. Spatz et al.; Identification of the Feline Herpesvirus Type 1 (FHV-1) Genes Encoding Glycoproteins G. D. I and E: Expression of FHV-1 Glycoprotein D in Vaccinia and Raccoon Poxvirus; J of General Virology; vol. 75; pp. 1235-1244; 1994.

Jill Taylor et al.; Efficacy Studies on a Canarypdx-Rabies Recombinant Virus; Vaccine, vol. 9; pp. 190-193; 1991.

Elaine k. Thomas et al.; Further Characterization of Raccoonpox Virus; Archives of Virology; vol. 49; pp. 217-227; 1975.

Elizabeth Yelverton et al.; Rabies Virus Glycoprotein Analogs: Biosynthesis in *Escherichia Coli*; Science; vol. 219; pp. 614-620; 1983.

A. L. Erickson et al.; Hepatitis C Virus-Specific CTL Responses in the Liver of Chimpanzees With Acute and Chronic Hepatitis C; J of Immunology; vol. 151(8); pp. 4189-4199; 1993.

Barbara Doe et al; Induction of HIV-1 Envelop (GP120)-Specific Cytotoxic T Lymphocyte Responses in Mice by Recombinant Cho Cell-Derived GP12O Is Enhanced by Enzymatic Removal of N-Linked Glycans; European Journal of Immunology; vol. 24; pp. 2369-2375; 1994.

Kathleen F. Cavallaro at al; Sequences of the Raccoon Poxvirus Hemagglutinin Protein; Virology; vol. 190(1); pp. 434-439; 1992.

Martinez et al., "Antigenic comparison and immune response in challenges mice with virus CVS and "street" and "fixed" isolates presumably atipics of rabies virus". Archivos de Medicina Veterinaria, vol. 31, No. 1, 1999.

Boles et al., "Raccoonpoxvirus Safety in Immunocompromised Mice". Poster Presented at East Carolina State University, Dec. 2011, 1 page

* cited by examiner

```
                              >PciI
                                |
         10         20      |  30         40          50         60
      TTATTGGACA CTAGATAATC ATCACATGTT ACCACAAAAT TATATAATGT ATAAATGCGA
      > RCNV HA-L Start >NcoI
                                |
         70         80      |  90         100        110        120
      AATTATTAAA CGCAAATATC CATGGGAAAA CGCGCAGTAT ACAGACGATT TTTTACAGTA 130        140        150        160        170        180
      TTTGGAGAGT TTTATAGGAA GTATATAGAG TAGAACCAGA ATTTTGTAAA AATAAATCAC 190        200        210        220        230        240
      ATTTTTATAC TAATATGAAA CAACTATCGA TAGTTATATT GCTACTATCG ATAGTATATA >EcoRV
                                |
         250        260     |  270        280        290        300
      CAACCAAACC TCATCCTACA CAGATATCAA AAAAACTAGG CGATGATGCT ACTCTATCGT >EcoRV
                                |
         310        320     |  330        340        350        360
      GTAATAGAAA CAATACACAT GGATATCTTG TCATGAGTTC TTGGTATAAG AAACCAGACT 370        380        390        400        410        420
      CCATTATTCT CTTAGCAGCC AAAAACGATG TCGTATACTT TGATGATTAT ACAGCGGATA 430        440        450        460        470        480
      AAGTATCATA CGATTCACCG TATGATACTC TAGCTACAAT TATTACAATT AAATCATTGA 490        500        510        520        530        540
      CATCTGGAGA TGCAGGTACT TATATATGCG CATTCTTTAT AACATCAACA AATGATACGG >EcoRI   >SalI
                    |       |
         550        560  |  570        580        590        600
      ATAAAATAGA TTATGAAGAA TTCGTCGACT CACAGTCCGG TCTCACCCCC GCTCTTGTAT
                                      < *  L  G  T  E  G  G  S  K  Y
```

FIG.1A

```
       610        620        630        640        650        660
GATTCCCATG AAGATATGAT CTTCCCGCTT TGGGGAGTGA CTGACACCTC CCTCCCTGTC
 S  E  W  S    S  I  I    K  G  S    Q  P  T  V    S  V  E    R  G  T 670        680        690        700        710        720
CCTCTGAGAT TGTGTTGTGT AGGTTCCGAT CGATTGACTC TTCTCCAGCA TGTCATCAGG
 G  R  L  N   H  Q  T    P  E  S    R  N  V  R    R  W  C    T  M  L 730        740        750        760        770        780
AAAATTATCA ACATCAAGGC AGTCAGGGCC CCTGCACTCA GTAATACATA CTTCCCCCAG
 F  I  I  L    M  L  A    T  L  A    G  A  S    L  L  V  Y    K  G  W 790        800        810        820        830        840
TTCGGGAGAC CCAAGTCAAC TCCTGAGATC CGTTCGTGCA CATCGGGAAG GTGAACTTCA
 N  P  L  G    L  D  V    G  S  I    R  E  H  V    D  P  L    H  V  E 850        860        870        880        890        900
ACAAAAATCCT CAGCCTCGTC ACCGTTCTTG AAAACGGTAG ACGGGTCTGC CAGGGGGTGC
 V  N  D  E    A  E  D    G  N  K    F  V  T  S    P  D  A    L  P  H 910        920        930        940        950        960
ATAAGGGGGA TAACCGAGGA TACCAACAAC TCCATATGTT GCTGGAGGAG GGATGATTGC
 M  L  P  I    V  S  S    V  L  L    E  M  H  Q    L  L  S    S  Q 970        980        990       1000       1010       1020
ATCTCTGGGA TTAAGACATT GCCGTCAGGT CCTAATATTA TACCATTGAA AAATACCCCG
 M  E  P  I    L  V  N    G  D  P    G  L  I  I    G  N  F    N  V  G 1030       1040       1050       1060       1070       1080
TTTACATGAG GATGACACCT CCCCCCAACT CTTAAACACC CTTTTGAAGG GATGATCTCA
 N  V  H  P    H  C  R    G  G  V    R  L  C  G    K  S  P    I  I  E 1090       1100       1110       1120       1130       1140
TTCCAAGTTC TGACTGACTT GTAGTGAGCA TCGGCTTCCA TCAAGGTCTT GTTGAATATG
 N  W  T  R    V  S  K    Y  H  A    D  A  E  M    L  T  K    N  F  I 1150       1160       1170       1180       1190       1200
GTATATGCTT TTCCAAACCC AGGGACAAGT TTTCTTAAAT GACTGAGACG TCTGAAACTC
 T  Y  A  K    G  N  G    P  V  L    K  R  L  H    S  L  R    R  F  S 1210       1220       1230       1240       1250       1260
ACTGACTTGG TGGTCATGAT GGACTCTAGT GCATCCAGAC ACTCCTCTCT CTTCTTGACC
 V  S  K  T    T  M  I    S  E  L    A  D  L  C    E  E  R    K  K  V
```

FIG.1B

```
      1270       1280       1290       1300       1310       1320
AACTCCTCTA CAACAAGGTG CTCAATTTCG TCTGAGCGAA AGTCGTGCAA ATTGATCAAC
 L  E  E  V   V  L  H  E   I  E  D  S   R  N  D  H   L  N  I  L 1330       1340       1350       1360       1370       1380
TGACCGGGAG GGCACCATTT GGTTTCATTT GATGTTTGCA TCGAGACCCA TGTTCCATCC
 Q  G  P  P   C  W  K  T   E  N  S  T   Q  M  S  V   W  T  G  D

>SphI
                                                |
      1390       1400       1410       1420     |  1430       1440
ATAAGTCTAA GTCCGAGAAC TCCACATAAC TGGAGTTTGC ATGCTCCTTT TAAAGACTTA
 M  L  R  L   G  L  V  G   C  L  Q  L   K  C  A  G   K  L  S  K 1450       1460       1470       1480       1490       1500
TATAGGCCTC TTTCATCTAC AAAGCCGCAA GTCTCACTCC CTTTGGATGC TCTCTTCCCT
 Y  L  G  R   E  D  V  N   G  C  T  E   S  G  K  S   A  R  K  G 1510       1520       1530       1540       1550       1560
CTACTATTGG TAAAAATGTC ACAAGACATC CCTAGTCTCG GATTCTCGGG CATCCAAATG
 R  S  N  T   N  I  D  C   S  M  G  L   R  P  N  E   P  M  W  I 1570       1580       1590       1600       1610       1620
GTGTAATCGT GGTTAGTGGA GCAGTAGGTA GAAGACACCG CTACTCCTGA GCACTTCCCG
 T  Y  D  H   N  T  S  C   Y  T  S  S   V  A  G  S   C  K  G

>XhoI
               |
      1630   |   1640       1650       1660       1670       1680
CCAGGGAAGA CCCTCGAGTG AAGGGATCTG TCATATGGGT CCAAATCTGC CACACTTGGA
 G  P  F  V   R  S  H  L   S  R  D  Y   P  D  L  D   A  V  S  P 1690       1700       1710       1720       1730       1740
GATATGATAA CGAGAGACTC CTTGGTGGTT TTTACAGTTC GAAGCCAGTG GTAGTCAGGG
 S  I  I  V   L  S  E  K   T  T  K  V   T  R  L  W   H  Y  D  P 1750       1760       1770       1780       1790       1800
TACGGATTGT GTAGAGACTC TTCATATCTG GGGTCACCGG CCATCTTCCA GTTGTACGCG
 Y  P  N  H   L  S  E  E   Y  R  P  D   G  A  M  K   W  N  Y  A

>NsiI
               |
      1810   |   1820       1830       1840       1850       1860
GCTCTACATG CATCTGGTGT TGGGCGGAAA TGCTTTCTTT TGAACGTGGT TGTGACATAA
 A  R  C  A   D  P  T  P   R  F  H  K   R  K  F  T   T  T  V  Y
```

FIG. 1C

```
      1870       1880       1890       1900       1910       1920
CCAACGAAGT TAGTGTAGGT TTCAGCCTCC GTCACAACGC CTGTGCAAGT GAACCCGTTC
 G  V  F  N  T  Y  T  E  A  E  T  V  V  G  T  C  T  F  G  N 1930       1940       1950       1960       1970       1980
ATTTTTATGG CTGAGATGTA TCCAACTTTA AGTTCCATGT AGGAGAACCC TGACAGGTTG
 M  K  I  A  S  I  Y  G  V  K  L  E  M  Y  S  F  G  S  L  N 1990       2000       2010       2020       2030       2040
GTGCATCCTT CGTCCTCCAC TACCAAATTG TTTGGGCAGC TGAGGTGATG TATGTCAATC
 T  C  G  E  D  E  V  V  L  N  N  P  C  S  L  H  H  I  D  I

>HindIII
                    |
      2050       | 2060       2070       2080       2090       2100
GGGCTCCAGG GACCAAGCTT GTCTGGTATC GTGTAAATAG GGAATTTCCC AAAACACAAT
 P  S  W  P  G  L  K  D  P  I  T  Y  I  P  F  K  G  N  C  L >KpnI
                                                        |
                                                      >NcoI
                                                        |
      2110       2120       2130       2140       2150       2160
GGAAAAACCA GAAGGGGTAC AAACAGGAGA GCCTGAGGAA CCGGTACCAT GGGTATTTAT
 P  N  V  L  L  P  V  N  L  L  A  Q  P  V  (P  V) M
                                                < Rabies Paris G >XbaI
                                  |
                          <PSEL_Promoter   >vv_P7.5_Promotor
                                  ||        |
      2170       2180       2190  ||2200    | 2210       2220
ATTCCAAAAA AAAAAAATAA AATTTCAATT TTTGCTCTAG ACATCTATAT ACTATATAGT 2230       2240       2250       2260       2270       2280
AATACCAATA CTCAAGACTA CGAAACTGAT ACAATCTCTT ATCATGTGGG TAATGTTCTC 2290       2300       2310       2320       2330       2340
GATGTCGATA GCCATATGCC CGGTAGTTGC GATATACATA AACTGATCAC TAATTCCAAA 2350       2360       2370       2380       2390       2400
CCCACCCGCT TTTTATAGTA AGTTTTTCAC CCATAAATAA TAAATACAAT AATTAATTTC
```

FIG.1D

```
           2410        2420        2430        2440        2450        2460
    TCGTAAAAGT AGAAAATATA TTCTAATTTA TTGCACGGTA AGGAAGTAGA ATCATAAAGA

>BamHI
           |
           2470 |      2480        2490        2500        2510        2520
    ACAGTGACAT GGATCCCGTC GTTTTACAAC GTCGTGACTG GGAAAACCCT GGCGTTACCC
              M  D  P  V   V  L  Q  R   R  D  W   E  N  P   G  V  T
              > LacZ ORF 2530        2540        2550        2560        2570        2580
    AACTTAATCG CCTTGCAGCA CATCCCCCTT TCGCCAGCTG GCGTAATAGC GAAGAGGCCC
     Q  L  N  R   L  A  A   H  P  P   F  A  S  W   R  N  S   E  E  A 2590        2600        2610        2620        2630        2640
    GCACCGATCG CCCTTCCCAA CAGTTGCGCA GCCTGAATGG CGAATGGCGC TTTGCCTGGT
      R  T  D  R   P  S  Q   Q  L  R   S  L  N  G   E  W  R   N  A  W 2650        2660        2670        2680        2630        2700
    TTCCGGCACC AGAAGCGGTG CCGGAAAGCT GGCTGGAGTG CGATCTTCCT GAGGCCGATA
       N  P  A  P   E  A  V   P  E  S   W  L  E  C   D  L  P   E  A  D 2710        2720        2730        2740        2750        2760
    CTGTCGTCGT CCCCTCAAAC TGGCAGATGC ACGGTTACGA TGCGCCCATC TACACCAACG
       T  V  V  V   P  S  N   W  Q  M   H  G  Y  D   A  P  I   Y  T  N 2770        2780        2790        2800        2810        2820
    TAACCTATCC CATTACGGTC AATCCGCCGT TTGTTCCCAC GGAGAATCCG ACGGGTTGTT
       V  T  Y  P   I  T  V   N  P  P   N  V  P  T   E  N  P   T  G  C 2830        2840        2850        2860        2870        2880
    ACTCGCTCAC ATTTAATGTT GATGAAAGCT GGCTACAGGA AGGCCAGACG CGAATTATTT
       Y  S  L  T   N  N  V   D  E  S   W  L  Q  E   G  Q  T   R  I  I

>HpaI
                 |
           2890 |      2900        2910        2920        2930        2940
    TTGATGGCGT TAACTCGGCG TTTCATCTGT GGTGCAACGG GCGCTGGGTC GGTTACGGCC
       N  D  G  V   N  S  A   N  H  L   W  C  N  G   R  W  V   G  Y  G 2950        2960        2970        2980        2990        3000
    AGGACAGTCG TTTGCCGTCT GAATTTGACC TGAGCGCATT TTTACGCGCC GGAGAAAACC
      Q  D  S  R   L  P  S   E  N  D   L  S  A  N   L  R  A   G  E  N
```

FIG.1E

```
       3010       3020       3030       3040       3050       3060
GCCTCGCGGT GATGGTGCTG CGTTGGAGTG ACGGCAGTTA TCTGGAAGAT CAGGATATGT
 R  L  A  V  M  V  L  R  W  S  D  G  S  Y  L  E  D  Q  D  M 3070       3080       3090       3100       3110       3120
GGCGGATGAG CGGCATTTTC CGTGACGTCT CGTTGCTGCA TAAACCGACT ACACAAATCA
 W  R  M  S  G  I  F  R  D  V  S  L  L  H  K  P  T  T  Q  I 3130       3140       3150       3160       3170       3180
GCGATTTCCA TGTTGCCACT CGCTTTAATG ATGATTTCAG CCGCGCTGTA CTGGAGGCTG
 S  D  F  H  V  A  T  R  N  N  D  D  F  S  R  A  V  L  E  A 3190       3200       3210       3220       3230       3240
AAGTTCAGAT GTGCGGCGAG TTGCGTGACT ACCTACGGGT AACAGTTTCT TTATGGCAGG
 E  V  Q  M  C  G  E  L  R  D  Y  L  R  V  T  V  S  L  W  Q 3250       3260       3270       3280       3290       3300
GTGAAACGCA GGTCGCCAGC GGCACCGCGC CTTTCGGCGG TGAAATTATC GATGAGCGTG
 G  E  T  Q  V  A  S  G  T  A  P  F  G  G  E  I  I  D  E  R 3310       3320       3330       3340       3350       3360
GTGGTTATGC CGATCGCGTC ACACTACGTC TCAAGGTCGA AAACCCGAAA CTGTGGAGCG
 G  G  Y  A  D  R  V  T  L  R  L  K  V  E  N  P  K  L  W  S 3370       3380       3390       3400       3410       3420
CCGAAATCCC GAATCTCTAT CGTGCGGTGG TTGAACTGCA CACCGCCGAC GGCACGCTGA
 A  E  I  P  N  L  Y  R  A  V  V  E  L  H  T  A  D  G  T  L 3430       3440       3450       3460       3470       3480
TTGAAGCAGA AGCCTGCGAT GTCGGTTTCC GCGAGGTGCG GATTGAAAAT GGTCTGCTGC
 I  E  A  E  A  C  D  V  G  F  R  E  V  R  I  E  N  G  L  L
                                             >HpaI
                                               |
       3490       3500       3510     |  3520       3530       3540
TGCTGAACGG CAAGCCGTTG CTGATTCGAG GCGTTAACCG TCACGAGCAT CATCCTCTGC
 L  L  N  G  K  P  L  L  I  R  G  V  N  R  H  E  H  H  P  L
                                       >EcoRV
                                         |
       3550       3560       3570       3580       3590       3600
ATGGTCAGGT CATGGATGAG CAGACGATGG TGCAGGATAT CCTGCTGATG AAGCAGAACA
 H  G  Q  V  M  D  E  Q  T  M  V  Q  D  I  L  L  M  K  Q  N
```

FIG.1F

```
     3610       3620       3630       3640       3650       3660
ACTTTAACGC CGTGCGCTGT TCGCATTATC CGAACCATCC GCTGTGGTAC ACGCTGTGCG
  N  N  N   A  V  R  C   S  H  Y   P  N  H  P   L  W  Y   T  L  C 3670       3680       3690       3700       3710       3720
ACCGCTACGG CCTGTATGTG GTGGATGAAG CCAATATTGA AACCCACGGC ATGGTGCCAA
  D  R  Y  G  L  Y  V  V  D  E   A  N  I  E   T  H  G   M  V  P
                                            >MluI
                                              |
     3730       3740       3750       3760       3770       3780
TCAATCGTCT GACCGATGAT CCGCGCTGGC TACCGGCGAT GAGCGAACGC GTAACGCGAA
  I  N  R  L   T  D  D   P  R  W   L  P  A  M   S  E  R   V  T  R 3790       3800       3810       3820       3830       3840
TGGTGCAGCG CGATCGTAAT CACCCGAGTG TGATCATCTG GTCGCTGGGG AATGAATCAG
  M  V  Q  R   D  R  N   H  P  S   V  I  I  W   S  L  G   N  E  S 3850       3860       3870       3880       3890       3900
GCCACGGCGC TAATCACGAC GCGCTGTATC GCTGGATCAA ATCTGTCGAT CCTTCCCGCC
  G  H  G  A   N  H  D   A  L  Y   R  W  I  K   S  V  D   P  S  R 3910       3920       3930       3940       3950       3960
CGGTGCAGTA TGAAGGCGGC GGAGCCGACA CCACGGCCAC CGATATTATT TGCCCGATGT
  P  V  Q  Y   E  G  G   G  A  D   T  T  A  T   D  I  I   C  P  M 3970       3980       3990       4000       4010       4020
ACGCGCGCGT GGATGAAGAC CAGCCCTTCC CGGCTGTGCC GAAATGGTCC ATCAAAAAAT
  Y  A  R  V   D  E  D   Q  P  F   P  A  V  P   K  W  S   I  K  K 4030       4040       4050       4060       4070       4080
GGCTTTCGCT ACCTGGAGAG ACGCGCCCGC TGATCCTTTG CGAATACGCC CACGCGATGG
  W  L  S  L   P  G  E   T  R  P   L  I  L  C   E  Y  A   H  A  M 4090       4100       4110       4120       4130       4140
GTAACAGTCT TGGCGGTTTC GCTAAATACT GGCAGGCGTT TCGTCAGTAT CCCCGTTTAC
  G  N  S  L   G  G  F   A  K  Y   W  Q  A  N   R  Q  Y   P  R  L 4150       4160       4170       4180       4190       4200
AGGGCGGCTT CGTCTGGGAC TGGGTGGATC AGTCGCTGAT TAAATATGAT GAAAACGGCA
  Q  G  G  F   V  W  D   W  V  D   Q  S  L  I   K  Y  D   E  N  G 4210       4220       4230       4240       4250       4260
ACCCGTGGTC GGCTTACGGC GGTGATTTTG GCGATACGCC GAACGATCGC CAGTTCTGTA
  N  P  W  S   A  Y  G   G  D  F   G  D  T  P   N  D  R   Q  F  C
```

FIG.1G

```
              4270       4280       4290       4300       4310       4320
         TGAACGGTCT GGTCTTTGCC GACCGCACGC CGCATCCAGC GCTGACGGAA GCAAAACACC
          M  N  G  L  V  N  A  D  R  T  P  H  P  A  L  T  E  A  K  H 4330       4340       4350       4360       4370       4380
         AGCAGCAGTT TTTCCAGTTC CGTTTATCCG GGCAAACCAT CGAAGTGACC AGCGAATACC
          Q  Q  Q  N  F  Q  F  R  L  S  G  Q  T  I  E  V  T  S  E  Y

>SacI
                                |
              4390       4400  |  4410       4420       4430       4440
         TGTTCCGTCA TAGCGATAAC GAGCTCCTGC ACTGGATGGT GGCGCTGGAT GGTAAGCCGC
          L  F  R  H  S  D  N  E  L  L  H  W  M  V  A  L  D  G  K  P 4450       4460       4470       4480       4490       4500
         TGGCAAGCGG TGAAGTGCCT CTGGATGTCG CTCCACAAGG TAAACAGTTG ATTGAACTGC
          L  A  S  G  E  V  P  L  D  V  A  P  Q  G  K  Q  L  I  E  L

>MluI
                                                        |
              4510       4520       4530       4540    | 4550       4560
         CTGAACTACC GCAGCCGGAG AGCGCCGGGC AACTCTGGCT CACAGTACGC GTAGTGCAAC
          P  E  L  P  Q  P  E  S  A  G  Q  L  W  L  T  V  R  V  V  Q 4570       4580       4590       4600       4610       4620
         CGAACGGGAC CGCATGGTCA GAAGCCGGGC ACATCAGCGC CTGGCAGCAG TGGCGTCTGG
          P  N  A  T  A  W  S  E  A  G  H  I  S  A  W  Q  Q  W  R  L 4630       4640       4650       4660       4670       4680
         CGGAAAACCT CAGTGTGACG CTCCCCGCCG CGTCCCACGC CATCCCGCAT CTGACCACCA
          A  E  N  L  S  V  T  L  P  A  A  S  H  A  I  P  H  L  T  T 4690       4700       4710       4720       4730       4740
         GCGAAATGGA TTTTTGCATC GAGCTGGGTA ATAAGCGTTG GCAATTTAAC CGCCAGTCAG
          S  E  M  D  N  C  I  E  L  G  N  K  R  W  Q  N  N  R  Q  S 4750       4760       4770       4780       4790       4800
         GCTTTCTTTC ACAGATGTGG ATTGGCGATA AAAAACAACT GCTGACGCCG CTGCGCGATC
          G  N  L  S  Q  M  W  I  G  D  K  K  Q  L  L  T  P  L  R  D 4810       4820       4830       4840       4850       4860
         AGTTCACCCG TGCACCGCTG GATAACGACA TTGGCGTAAG TGAAGCGACC CGCATTGACC
          Q  F  T  R  A  P  L  D  N  D  I  G  V  S  E  A  T  R  I  D
```

FIG. 1H

```
        4870       4880       4890       4900       4910       4920
    CTAACGCCTG GGTCGAACGC TGGAAGGCGG CGGGCCATTA CCAGGCCGAA GCAGCGTTGT
     P  N  A  W  V  E  R  W  K  A  A  G  H  Y  Q  A  E  A  A  L
                                                        >MluI
                                                         |
        4930       4940       4950       4960       4970  |   4980
    TGCAGTGCAC GGCAGATACA CTTGCTGATG CGGTGCTGAT TACGACCGGT CACGCGTGGC
     L  Q  C  T  A  D  T  L  A  D  A  V  L  I  T  T  G  H  A  W 4990       5000       5010       5020       5030       5040
    AGCATCAGGG GAAAACCTTA TTTATCAGCC GGAAAACCTA CCGGATTGAT GGTAGTGGTC
     Q  H  Q  G  K  T  L  N  I  S  R  K  T  Y  R  I  D  G  S  G 5050       5060       5070       5080       5090       5100
    AAATGGCGAT TACCGTTGAT GTTGAAGTGG CGAGCGATAC ACCGCATCCG GCGCGGATTG
     Q  M  A  I  T  V  D  V  E  V  A  S  D  T  P  H  P  A  R  I 5110       5120       5130       5140       5150       5160
    GCCTGAACTG CCAGCTGGCG CAGGTAGCAG AGCGGGTAAA CTGGCTCGGA TTAGGGCCGC
     G  L  N  C  Q  L  A  Q  V  A  E  R  V  N  W  L  G  L  G  P 5170       5180       5190       5200       5210       5220
    AAGAAAACTA TCCCGACCGC CTTACTGCCG CCTGTTTTGA CCGCTGGGAT CTGCCATTGT
     Q  E  N  Y  P  D  R  L  T  A  A  C  N  D  R  W  D  L  P  L

>PciI
     |
     | 5230       5240       5250       5260       5270       5280
    CAGACATGTA TACCCCGTAC GTCTTCCCGA GCGAAAACGG TCTGCGCTGC GGGACGCGCG
     S  D  M  Y  T  P  Y  V  F  P  S  E  N  G  L  R  C  G  T  R 5290       5300       5310       5320       5330       5340
    AATTGAATTA TGGCCCACAC CAGTGGCGCG GCGACTTCCA GTTCAACATC AGCCGCTACA
     E  L  N  Y  G  P  H  Q  W  R  G  D  F  Q  F  N  I  S  R  Y 5350       5360       5370       5380       5390       5400
    GTCAACAGCA ACTGATGGAA ACCAGCCATC GCCATCTGCT GCACGCGGAA GAAGGCACAT
     S  Q  Q  Q  L  M  E  T  S  H  R  H  L  L  H  A  E  E  G  T 5410       5420       5430       5440       5450       5460
    GGCTGAATAT CGACGGTTTC CATATGGGGA TTGGTGGCGA CGACTCCTGG AGCCCGTCAG
     W  L  N  I  D  G  F  H  M  G  I  G  G  D  D  S  W  S  P  S
```

FIG. 1I

>EcoRI

```
        5470       5480       5490       5500       5510       5520
   TATCGGCGGA ATTCCAGCTG AGCGCCGTTC GCTACCATTA CCAGTTGGTC TGGTGTCAAA
    V  S  A  E  F  Q  L  S  A  V  R  Y  H  Y  Q  L  V  W  C  Q
```

>BamHI

```
       |5530       5540       5550       5560       5570       5580
   AATAAGGATC CTCGATACCA ACAACGGTAG AAAGTGTTAC AATATCTACT ACAAAATATA
    K  *>          > HA-R Start
```

>SpeI

```
   |    5590       5600       5610       5620       5630       5640
   CAACTAGTGA CTTTATAGAG ATATTTGGCA TTGTTTCACT AATTTTATTA TTGGCCGTGG 5650       5660       5670       5680       5690       5700
   CGATTTTCTG TATTATATAT TATTTCTGTA GTGGACGGTC TCGTAAACAA GAAACAAATA 5710       5720       5730       5740       5750       5760
   TATTATAGAT TTTAACTCAG ATAAATGTCT GGAATAATTA AATCTATCGT TTTGAGCGGA 5770       5780       5790       5800       5810       5820
   CCATCTGGTT CCGGCAAGAC AGCTATAGTC AGGAGACTCT TACAAGATTA TGGAAATATA 5830       5840       5850       5860       5870       5880
   TTTGGATTTG TGGTATCCCA TACCACTAGA TTTCCTCGTC CTATGGAACG AGAAGGTGTC
```

>HpaI

```
        5890     | 5900       5910       5920       5930       5940
   GTCTACCATT ACGTTAACAG AGAGGCCATT TGGAAGGGAA TAGCCGCTGG AAACTTGCTA 59520       5960       5970       5980       5990       6000
   GAACATACAG AGTTTTTGGG AAATATTTAT GGGACTTCTA AAACATCCAT GAACACAGCT 6010       6020       6030       6040       6050       6060
   GCTATTAATA ATCGTATATG TGTTATGGAT TTAAACATTG ACGGAGTTAG GAGTCTTAAA 6070       6080       6090       6100       6110       6120
   AACACATACT TGATGCCTTA CTCTGTTTAT ATAAGACCTA CATCTCTTAA AATGGTAGAA
```

FIG.1J

>SphI

```
        6130       6140       6150       6160       6170       6180
    ACTGCATGCC CTGATGCGGT ATTTTCTCCT TACGCATCTG TGCGGTATTT CACACCGCAT 6190       6200       6210       6220       6230       6240
    ATGGTGCACT CTCAGTACAA TCTGCTCTGA TGCCGCATAG TTAAGCCAGC CCCGACACCC 6250       6260       6270       6280       6290       6300
    GCCAACACCC GCTGACGCGC CCTGACGGGC TTGTCTGCTC CCGGCATCCG CTTACAGACA 6310       6320       6330       6340       6350       6360
    AGCTGTGACC GTCTCCGGGA GCTGCATGTG TCAGAGGTTT TCACCGTCAT CACCGAAACG 6370       6380       6390       6400       6410       6420
    CGCGAGACGA AAGGGCCTCG TGATACGCCT ATTTTTATAG GTTAATGTCA TGATAATAAT 6430       6440       6450       6460       6470       6480
    GGTTTCTTAG ACGTCAGGTG GCACTTTTCG GGGAAATGTG CGCGGAACCC CTATTTGTTT 6490       6500       6510       6520       6530       6540
    ATTTTTCTAA ATACATTCAA ATATGTATCC GCTCATGAGA CAATAACCCT GATAAATGCT 6550       6560       6570       6580       6590       6600
    TCAATAATAT TGAAAAAGGA AGAGTATGAG TATTCAACAT TTCCGTGTCG CCCTTATTCC
                                  M  S  I  Q  H  F  R  V  A  L  I  P
                              > Ampicillin ORF 6610       6620       6630       6640       6650       6660
    CTTTTTTGCG GCATTTTGCC TTCCTGTTTT TGCTCACCCA GAAACGCTGG TGAAAGTAAA
     N  N  A  A  N  C  L  P  V  N  A  H  P  E  T  L  V  K  V  K 6670       6680       6690       6700       6710       6720
    AGATGCTGAA GATCAGTTGG GTGCACGAGT GGGTTACATC GAACTGGATC TCAACAGCGG
     D  A  E  D  Q  L  G  A  R  V  G  Y  I  E  L  D  L  N  S  G 6730       6740       6750       6760       6770       6780
    TAAGATCCTT GAGAGTTTTC GCCCCGAAGA ACGTTTTCCA ATGATGAGCA CTTTTAAAGT
     K  I  L  E  S  N  R  P  E  E  R  N  P  M  M  S  T  N  K  V 6790       6800       6810       6820       6830       6840
    TCTGCTATGT GGCGCGGTAT TATCCCGTAT TGACGCCGGG CAAGAGCAAC TCGGTCGCCG
     L  L  C  G  A  V  L  S  R  I  D  A  G  Q  E  Q  L  G  R  R
```

FIG.1K

```
      6850       6860       6870       6880       6890       6900
CATACACTAT TCTCAGAATG ACTTGGTTGA GTACTCACCA GTCACAGAAA AGCATCTTAC
  I  H  Y   S  Q  N    D  L  V    E  Y  S    P  V  T    E  K  H  L  T 6910       6920       6930       6940       6950       6960
GGATGGCATG ACAGTAAGAG AATTATGCAG TGCTGCCATA ACCATGAGTG ATAACACTGC
  D  G  M   T  V  R    E  L  C    S  A  A  I  T  M  S    D  N  T  A 6970       6980       6990       7000       7010       7020
GGCCAACTTA CTTCTGACAA CGATCGGAGG ACCGAAGGAG CTAACCGCTT TTTTGCACAA
  A  N  L   L  L  T    I  G  G    P  K  E    L  T  A    N  L  H  N 7030       7040       7050       7060       7070       7080
CATGGGGGAT CATGTAACTC GCCTTGATCG TTGGGAACCG GAGCTGAATG AAGCCATACC
  M  G  D   H  V  T    R  L  D  R  W  E  P    E  L  N    E  A  I  P 7090       7100       7110       7120       7130       7140
AAACGACGAG CGTGACACCA CGATGCCTGT AGCAATGGCA ACAACGTTGC GCAAACTATT
  N  D  E   R  D  T    T  M  P  V  A  M  A    T  T  L    R  K  L  L 7150       7160       7170       7180       7190       7200
AACTGGCGAA CTACTTACTC TAGCTTCCCG GCAACAATTA ATAGACTGGA TGGAGGCGGA
  T  G  E   L  L  T    L  A  S  R  Q  Q  L    I  D  W    M  E  A  D 7210       7220       7230       7240       7250       7260
TAAAGTTGCA GGACCACTTC TGCGCTCGGC CCTTCCGGCT GGCTGGTTTA TTGCTGATAA
  K  V  A   G  P  L    L  R  S    A  L  P    A  G  W    N  I  A  D  K 7270       7280       7390       7300       7310       7320
ATCTGGAGCC GGTGAGCGTG GGTCTCGCGG TATCATTGCA GCACTGGGGC CAGATGGTAA
  S  G  A   G  E  R    G  S  R    G  I  I    A  A  L    G  P  D  G  K 7330       7340       7350       7360       7370       7380
GCCCTCCCGT ATCGTAGTTA TCTACACGAC GGGGAGTCAG GCAACTATGG ATGAACGAAA
  P  S  R   I  V  V    I  Y  T  T  G  S  Q    A  T  M    D  E  R  N 7390       7400       7410       7420       7430       7440
TAGACAGATC GCTGAGATAG GTGCCTCACT GATTAAGCAT TGGTAACTGT CAGACCAAGT
  R  Q  I   A  E  I    G  A  S    L  I  K  H  W  *

7450       7460       7470       7480       7490       7500
TTACTCATAT ATACTTTAGA TTGATTTAAA ACTTCATTTT TAATTTAAAA GGATCTAGGT 7510       7520       7530       7540       7550       7560
GAAGATCCTT TTTGATAATC TCATGACCAA AATCCCTTAA CGTGAGTTTT CGTTCCACTG
```

FIG. 1L

```
       7570       7580       7590       7600       7610       7620
  AGCGTCAGAC CCCGTAGAAA AGATCAAAGG ATCTTCTTGA GATCCTTTTT TTCTGCGCGT 7630       7640       7650       7660       7670       7680
  AATCTGCTGC TTGCAAACAA AAAAACCACC GCTACCAGCG GTGGTTTGTT TGCCGGATCA 7690       7700       7710       7720       7730       7740
  AGAGCTACCA ACTCTTTTTC CGAAGGTAAC TGGCTTCAGC AGAGCGCAGA TACCAAATAC 7750       7760       7770       7780       7790       7800
  TGTTCTTCTA GTGTAGCCGT AGTTAGGCCA CCACTTCAAG AACTCTGTAG CACCGCCTAC 7810       7820       7830       7840       7850       7860
  ATACCTCGCT CTGCTAATCC TGTTACCAGT GGCTGCTGCC AGTGGCGATA AGTCGTGTCT 7870       7880       7890       7900       7910       7920
  TACCGGGTTG GACTCAAGAC GATAGTTACC GGATAAGGCG CAGCGGTCGG GCTGAACGGG 7930       7940       7950       7960       7970       7980
  GGGTTCGTGC ACACAGCCCA GCTTGGAGCG AACGACCTAC ACCGAACTGA GATACCTACA 7990       8000       8010       8020       8030       8040
  GCGTGAGCTA TGAGAAAGCG CCACGCTTCC CGAAGGGAGA AAGGCGGACA GGTATCCGGT 8050       8060       8070       8080       8090       8100
  AAGCGGCAGG GTCGGAACAG GAGAGCGCAC GAGGGAGCTT CCAGGGGGAA ACGCCTGGTA 8110       8120       8130       8140       8150       8160
  TCTTTATAGT CCTGTCGGGT TTCGCCACCT CTGACTTGAG CGTCGATTTT TGTGATGCTC 8170       8180       8190       8200       8210       8220
  GTCAGGGGGG CGGAGCCTAT GGAAAAACGC CAGCAACGCG GCCTTTTTAC GGTTCCTGGC

>PciI
                    |
       8230       8240 |     8250       8260       8270       8280
  CTTTTGCTGG CCTTTTGCTC ACATGTTCTT TCCTGCGTTA TCCCCTGATT CTGTGGATAA 8290       8300       8310       8320       8330       8340
  CCGTATTACC GCCTTTGAGT GAGCTGATAC CGCTCGCCGC AGCCGAACGA CCGAGCGCAG

>SacI
                                     |
       8350       8360       8370 |
  CGAGTCAGTG AGCGAGGAAG CGGAAGAGAG CTC
```

FIG. 1M

Major restriction enzymes that cut pFD2003SEL-GPV-PV between 1 and 3 times

| Enzyme | # Sites | Location | | |
|---|---|---|---|---|
| BamHI | 2 | 2471 | 5526 | |
| EcoRI | 2 | 558 | 5469 | |
| EcoRV | 3 | 265 | 324 | 3578 |
| HindIII | 1 | 2055 | | |
| HpaI | 3 | 2891 | 3515 | 5895 |
| KpnI | 1 | 2147 | | |
| MluI | 3 | 3767 | 4547 | 4972 |
| NcoI | 2 | 80 | 2147 | |
| NsiI | 1 | 1812 | | |
| PciI | 3 | 24 | 5224 | 8241 |
| SacI | 2 | 4405 | 8372 | |
| SalI | 1 | 564 | | |
| SpeI | 1 | 5583 | | |
| SphI | 2 | 1423 | 6128 | |
| XbaI | 1 | 2196 | | |
| XhoI | 1 | 1633 | | |

Major restriction enzymes that do not cut the pFD2003SEL-GPV-PV

BglII KasI NheI NotI NruI PmeI PstI SacII SmaI XmaI

FIG.2B

ANTIGENIC SITES

G PV — NH2 — SP — II — c b — III a — TM — COOH

Rabies G-cDNA (G-PV) was amplified by RT-PCR from rabies PV-Paris; KpnI – SalI rabies GPV-PV fragment was subclone into the pFD2003SEL.

pFD2003SEL-GPV-PV
8373 bp, Ap^r

Labeled sites: PciI, SacI, PciI, NcoI, HA Left, EcoRV, EcoRV, EcoRI, SalI, Multiple cloning sites, Rabies Paris G, SphI, XhoI, NsiI, HindIII, KpnI, NcoI, XbaI, PSEL Promoter, vv P7.5 Promoter, BamHI, HpaI, HpaI, MluI, EcoRV, LacZ ORF, MluI, SacI, MluI, PciI, EcoRI, BamHI, SpeI, HA Right, HpaI, SphI, Ampcillin ORF

FIG.3A

| LANE | SAMPLES (DNA TEMPLATE) | PRIMERS (GEL A) | PRIMERS (GEL B) | TARGET GENE | RESULTS |
|---|---|---|---|---|---|
| 1 | Lambda/Hind III Marker | NA | NA | NA | NA |
| 2 | rRCNV-Rabies G2, MSV | HA-08, HA-Pst | TK-LW, TK-RW | wt *ha/tk* | −* |
| 3 | rRCNV-Rabies G2, x + 5 | HA-08, HA-Pst | TK-LW, TK-RW | wt *ha/tk* | − |
| 4 | DNA Purification Negative Control-01 | HA-08, HA-Pst | TK-LW, TK-RW | wt *ha/tk* | − |
| 5 | DNA Purification Negative Control-02 | HA-08, HA-Pst | TK-LW, TK-RW | wt *ha/tk* | − |
| 6 | PCR Negative Control (water) | HA-08, HA-Pst | TK-LW, TK-RW | wt *ha/tk* | − |
| 7 | PCR Positive Control (RCNV Esposito-3) | HA-08, HA-Pst | TK-LW, TK-RW | wt *ha/tk* | +** |
| 8 | rRCNV-Rabies G2, MSV | HA-Pst, gp-1F | TK-RR, gJE-F1 | Rabies G | + |
| 9 | rRCNV-Rabies G2, x + 5 | HA-Pst, gp-1F | TK-RR, gJE-F1 | Rabies G | + |
| 10 | DNA Purification Negative Control-01 | HA-Pst, gp-1F | TK-RR, gJE-F1 | Rabies G | − |
| 11 | DNA Purification Negative Control-02 | HA-Pst, gp-1F | TK-RR, gJE-F1 | Rabies G | − |
| 12 | PCR Negative Control (water) | HA-Pst, gp-1F | TK-RR, gJE-F1 | Rabies G | − |
| 13 | PCR Positive Control (RCNV Esposito-3) | HA-Pst, gp-1F | TK-RR, gJE-F1 | Rabies G | − |
| 14 | 1kb DNA Ladder Marker | NA | NA | NA | NA |

Note: NA, not applicable; *−, PCR negative; **+, PCR positive; RCNV Esposito −3 dilution used as positive control.

FIG.5C

| LANE | SAMPLES | PRIMERS | GENE TARGET | RESULTS |
|---|---|---|---|---|
| 1 | Lambda/HindIII Marker | | | |
| 2 | rRCNV-Rabies G2 MSV | HA-Pst, PW-04 | 1806-bp Pasteur-Paris rabies G and its flanking region | + |
| 3 | rRCNV-Rabies G2 X + 5 | HA-Pst, PW-04 | | + |
| 4 | Negative control (water) | HA-Pst, PW-04 | | − |
| 5 | rRCNV-Rabies G2 MSV | TK-RR, PW-03 | 1910-bp CVS rabies G and its flanking region | + |
| 6 | rRCNV-Rabies G2 X + 5 | TK-RR, PW-03 | | + |
| 7 | Negative control (water) | TK-RR, PW-03 | | − |
| 8 | 1 kb DNA ladder Marker | | | |

FIG.7 rRCNV-Rabies G2 MSV (undiluted, $10^0$)

FIG.8A rRCNV-Rabies G2 X + 5 ($10^{-4}$ dilution)

FIG.8B

SEQUENCE LISTING

```
<160> NUMBER OF SEQ ID NOS: 13

<210> SEQ ID NO 1
<211> LENGTH: 8373
<212> TYPE: DNA
<213> ORGANISM: Artificial Sequence
<220> FEATURE:
<223> OTHER INFORMATION: plasmid

<400> SEQUENCE: 1
ttattggaca ctagataatc atcacatgtt accacaaaat tatataatgt ataaatgcga      60
aattattaaa cgcaaatatc catgggaaaa cgcgcagtat acagacgatt ttttacagta     120
tttggagagt tttataggaa gtatatagag tagaaccaga attttgtaaa aataaatcac     180
atttttatac taatatgaaa caactatcga tagttatatt gctactatcg atagtatata     240
caaccaaacc tcatcctaca cagatatcaa aaaaactagg cgatgatgct actctatcgt     300
gtaatagaaa caatacacat ggatatcttg tcatgagttc ttggtataag aaaccagact     360
ccattattct cttagcagcc aaaaacgatg tcgtatactt tgatgattat acagcggata     420
aagtatcata cgattcaccg tatgatactc tagctacaat tattacaatt aaatcattga     480
catctggaga tgcaggtact tatatatgcg cattctttat aacatcaaca aatgatacgg     540
```

-continued

```
ataaaataga ttatgaagaa ttcgtcgact cacagtccgg tctcaccccc gctcttgtat    600
gattcccatg aagatatgat cttcccgctt tggggagtga ctgacacctc cctccctgtc    660
cctctgagat tgtgttgtgt aggttccgat cgattgactc ttctccagca tgtcatcagg    720
aaaattatca acatcaaggc agtcagggcc cctgcactca gtaatacata cttccccag    780 ttcgggagac ccaagtcaac tcctgagatc cgttcgtgca catcgggaag gtgaacttca    840
acaaaatcct cagcctcgtc accgttcttg aaaacggtag acgggtctgc caggggtgc    900 ataaggggga taaccgagga taccaacaac tccatatgtt gctggaggag ggatgattgc    960
atctctggga ttaagacatt gccgtcaggt cctaatatta taccattgaa aaataccccg   1020
tttacatgag gatgacacct cccccaact cttaaacacc cttttgaagg gatgatctca   1080
ttccaagttc tgactgactt gtagtgagca tcggcttcca tcaaggtctt gttgaatatg   1140
gtatatgctt ttccaaaccc agggacaagt tttcttaaat gactgagacg tctgaaactc   1200
actgacttgg tggtcatgat ggactctagt gcatccagac actcctctct cttcttgacc   1260
aactcctcta caacaaggtg ctcaatttcg tctgagcgaa agtcgtgcaa attgatcaac   1320
tgaccgggag ggcaccattt ggtttcattt gatgtttgca tcgagaccca tgttccatcc   1380
ataagtctaa gtccgagaac tccacataac tggagtttgc atgctccttt taaagactta   1440
tataggcctc tttcatctac aaagccgcaa gtctcactcc ctttggatgc tctcttccct   1500
ctactattgg taaaaatgtc acaagacatc cctagtctcg gattctcggg catccaaatg   1560
gtgtaatcgt ggttagtgga gcagtaggta gaagacaccg ctactcctga gcacttcccg   1620
ccagggaaga ccctcgagtg aagggatctg tcatatgggt ccaaatctgc cacacttgga   1680
gatatgataa cgagagactc cttggtggtt tttacagttc gaagccagtg gtagtcaggg   1740
tacggattgt gtagagactc ttcatatctg gggtcaccgg ccatcttcca gttgtacgcg   1800
gctctacatg catctggtgt tgggcggaaa tgctttcttt tgaacgtggt tgtgacataa   1860
ccaacgaagt tagtgtaggt ttcagcctcc gtcacaacgc ctgtgcaagt gaacccgttc   1920 attttatgg ctgagatgta tccaactta agttccatgt aggagaaccc tgacaggttg   1980
gtgcatcctt cgtcctccac taccaaattg tttgggcagc tgaggtgatg tatgtcaatc   2040
gggctccagg gaccaagctt gtctggtatc gtgtaaatag ggaatttccc aaaacacaat   2100
ggaaaaacca aagggtac aaacaggaga gcctgaggaa ccggtaccat gggtatttat   2160
attccaaaaa aaaaaataa aatttcaatt tttgctctag acatctatat actatatagt   2220
aataccaata ctcaagacta cgaaactgat acaatctctt atcatgtggg taatgttctc   2280
gatgtcgata gccatatgcc cggtagttgc gatatacata aactgatcac taattccaaa   2340
cccacccgct ttttatagta agttttcac ccataaataa taaatacaat aattaatttc   2400
tcgtaaaagt agaaaatata ttctaattta ttgcacggta aggaagtaga atcataaaga   2460
acagtgacat ggatcccgtc gttttacaac gtcgtgactg gaaaaccct ggcgttaccc   2520 aacttaatcg ccttgcagca catccccctt tcgccagctg gcgtaatagc gaagaggccc   2580
gcaccgatcg cccttcccaa cagttgcgca gcctgaatgg cgaatggcgc tttgcctggt   2640
ttccggcacc agaagcggtg ccggaaagct ggctggagtg cgatcttcct gaggccgata   2700
ctgtcgtcgt cccctcaaac tggcagatgc acggttacga tgcgcccatc tacaccaacg   2760
taacctatcc cattacggtc aatccgccgt ttgttcccac ggagaatccg acgggttgtt   2820
actcgctcac atttaatgtt gatgaaagct ggctacagga aggccagacg cgaattattt   2880
```

```
ttgatggcgt taactcggcg tttcatctgt ggtgcaacgg gcgctgggtc ggttacggcc      2940
aggacagtcg tttgccgtct gaatttgacc tgagcgcatt tttacgcgcc ggagaaaacc      3000
gcctcgcggt gatggtgctg cgttggagtg acggcagtta tctggaagat caggatatgt      3060
ggcggatgag cggcattttc cgtgacgtct cgttgctgca taaaccgact acacaaatca      3120
gcgatttcca tgttgccact cgctttaatg atgatttcag ccgcgctgta ctggaggctg      3180
aagttcagat gtgcggcgag ttgcgtgact acctacgggt aacagtttct ttatggcagg      3240
gtgaaacgca ggtcgccagc ggcaccgcgc ctttcggcgg tgaaattatc gatgagcgtg      3300
gtggttatgc cgatcgcgtc acactacgtc tcaaggtcga aaacccgaaa ctgtggagcg      3360
ccgaaatccc gaatctctat cgtgcggtgg ttgaactgca caccgccgac ggcacgctga      3420
ttgaagcaga agcctgcgat gtcggtttcc gcgaggtgcg gattgaaaat ggtctgctgc      3480
tgctgaacgg caagccgttg ctgattcgag gcgttaaccg tcacgagcat catcctctgc      3540
atggtcaggt catggatgag cagacgatgg tgcaggatat cctgctgatg aagcagaaca      3600
actttaacgc cgtgcgctgt tcgcattatc cgaaccatcc gctgtggtac acgctgtgcg      3660
accgctacgg cctgtatgtg gtggatgaag ccaatattga aacccacggc atggtgccaa      3720
tcaatcgtct gaccgatgat ccgcgctggc taccggcgat gagcgaacgc gtaacgcgaa      3780
tggtgcagcg cgatcgtaat cacccgagtg tgatcatctg gtcgctgggg aatgaatcag      3840 gccacgcgc taatcacgac gcgctgtatc gctggatcaa atctgtcgat ccttcccgcc      3900
cggtgcagta tgaaggcggc ggagccgaca ccacggccac cgatattatt tgcccgatgt      3960
acgcgcgcgt ggatgaagac cagcccttcc cggctgtgcc gaaatggtcc atcaaaaaat      4020
ggctttcgct acctggagag acgcgcccgc tgatcctttg cgaatacgcc cacgcgatgg      4080
gtaacagtct tggcggtttc gctaaatact ggcaggcgtt tcgtcagtat ccccgtttac      4140
agggcggctt cgtctgggac tgggtggatc agtcgctgat taaatatgat gaaaacggca      4200
acccgtggtc ggcttacggc ggtgattttg gcgatacgcc gaacgatcgc cagttctgta      4260
tgaacggtct ggtctttgcc gaccgcacgc cgcatccagc gctgacggaa gcaaaacacc      4320
agcagcagtt tttccagttc cgtttatccg ggcaaaccat cgaagtgacc agcgaatacc      4380
tgttccgtca tagcgataac gagctcctgc actggatggt ggcgctggat ggtaagccgc      4440
tggcaagcgg tgaagtgcct ctggatgtcg ctccacaagg taaacagttg attgaactgc      4500
ctgaactacc gcagccggag agcgccgggc aactctggct cacagtacgc gtagtgcaac      4560
cgaacgcgac cgcatggtca gaagccgggc acatcagcgc ctggcagcag tggcgtctgg      4620
cggaaaacct cagtgtgacg ctccccgccg cgtcccacgc catcccgcat ctgaccacca      4680
gcgaaatgga ttttgcatc gagctgggta ataagcgttg gcaatttaac cgccagtcag      4740
gctttctttc acagatgtgg attggcgata aaaacaact gctgacgccg ctgcgcgatc      4800
agttcacccg tgcaccgctg gataacgaca ttggcgtaag tgaagcgacc cgcattgacc      4860
ctaacgcctg ggtcgaacgc tggaaggcgg cgggccatta ccaggccgaa gcagcgttgt      4920
tgcagtgcac ggcagataca cttgctgatg cggtgctgat tacgaccggt cacgcgtggc      4980
agcatcaggg gaaaacctta tttatcagcc ggaaaaccta ccggattgat ggtagtggtc      5040
aaatggcgat taccgttgat gttgaagtgg cgagcgatac accgcatccg gcgcggattg      5100
gcctgaactg ccagctggcg caggtagcag agcgggtaaa ctggctcgga ttagggccgc      5160
aagaaaacta tcccgaccgc cttactgccg cctgttttga ccgctgggat ctgccattgt      5220
cagacatgta taccccgtac gtcttcccga gcgaaaacgg tctgcgctgc gggacgcgcg      5280
```

-continued

```
aattgaatta tggcccacac cagtggcgcg gcgacttcca gttcaacatc agccgctaca   5340
gtcaacagca actgatggaa accagccatc gccatctgct gcacgcggaa gaaggcacat   5400
ggctgaatat cgacggtttc catatgggga ttggtggcga cgactcctgg agcccgtcag   5460
tatcggcgga attccagctg agcgccgttc gctaccatta ccagttggtc tggtgtcaaa   5520
aataaggatc ctcgatacca acaacggtag aaagtgttac aatatctact acaaaatata   5580
caactagtga ctttatagag atatttggca ttgtttcact aatttttatta ttggccgtgg   5640
cgattttctg tattatatat tatttctgta gtggacggtc tcgtaaacaa gaaacaaata   5700
tattatagat tttaactcag ataaatgtct ggaataatta aatctatcgt tttgagcgga   5760
ccatctggtt ccggcaagac agctatagtc aggagactct tacaagatta tggaaatata   5820
tttggatttg tggtatccca taccactaga tttcctcgtc ctatggaacg agaaggtgtc   5880
gtctaccatt acgttaacag agaggccatt tggaagggaa tagccgctgg aaacttgcta   5940
gaacatacag agttttggg aaatatttat gggacttcta aaacatccat gaacacagct   6000
gctattaata atcgtatatg tgttatggat ttaaacattg acggagttag gagtcttaaa   6060
aacacatact tgatgcctta ctctgtttat ataagaccta catctcttaa aatggtagaa   6120
actgcatgcc ctgatgcggt attttctcct tacgcatctg tgcggtattt cacaccgcat   6180
atggtgcact ctcagtacaa tctgctctga tgccgcatag ttaagccagc ccgacaccc    6240
gccaacaccc gctgacgcgc cctgacgggc ttgtctgctc ccggcatccg cttacagaca   6300
agctgtgacc gtctccggga gctgcatgtg tcagaggttt tcaccgtcat caccgaaacg   6360
cgcgagacga aagggcctcg tgatacgcct atttttatag gttaatgtca tgataataat   6420
ggtttcttag acgtcaggtg gcactttcg gggaaatgtg cgcggaaccc ctatttgttt    6480
attttctaa atacattcaa atatgtatcc gctcatgaga caataaccct gataaatgct   6540
tcaataatat tgaaaagga agagtatgag tattcaacat ttccgtgtcg cccttattcc   6600
cttttttgcg gcattttgcc ttcctgtttt tgctcaccca gaaacgctgg tgaaagtaaa   6660
agatgctgaa gatcagttgg gtgcacgagt gggttacatc gaactggatc tcaacagcgg   6720
taagatcctt gagagttttc gccccgaaga acgttttcca atgatgagca cttttaaagt   6780
tctgctatgt ggcgcggtat tatcccgtat tgacgccggg caagagcaac tcggtcgccg   6840
catacactat tctcagaatg acttggttga gtactcacca gtcacagaaa agcatcttac   6900
ggatggcatg acagtaagag aattatgcag tgctgccata accatgagtg ataacactgc   6960
ggccaactta cttctgacaa cgatcggagg accgaaggag ctaaccgctt ttttgcacaa   7020
catgggggat catgtaactc gccttgatcg ttgggaaccg gagctgaatg aagccatacc   7080
aaacgacgag cgtgacacca cgatgcctgt agcaatggca acaacgttgc gcaaactatt   7140
aactggcgaa ctacttactc tagcttcccg gcaacaatta atagactgga tggaggcgga   7200
taaagttgca ggaccacttc tgcgctcggc ccttccggct ggctggttta ttgctgataa   7260
atctggagcc ggtgagcgtg ggtctcgcgg tatcattgca gcactggggc cagatggtaa   7320
gccctcccgt atcgtagtta ctacacgac ggggagtcag gcaactatgg atgaacgaaa    7380
tagacagatc gctgagatag gtgcctcact gattaagcat tggtaactgt cagaccaagt   7440
ttactcatat atactttaga ttgatttaaa acttcatttt taatttaaaa ggatctaggt   7500
gaagatcctt tttgataatc tcatgaccaa aatcccttaa cgtgagtttt cgttccactg   7560
agcgtcagac cccgtagaaa agatcaaagg atcttcttga gatccttttt ttctgcgcgt   7620
```

```
aatctgctgc ttgcaaacaa aaaaaccacc gctaccagcg gtggtttgtt tgccggatca     7680
agagctacca actcttttc cgaaggtaac tggcttcagc agagcgcaga taccaaatac      7740
tgttcttcta gtgtagccgt agttaggcca ccacttcaag aactctgtag caccgcctac     7800
atacctcgct ctgctaatcc tgttaccagt ggctgctgcc agtggcgata agtcgtgtct     7860 taccggggttg gactcaagac gatagttacc ggataaggcg cagcggtcgg gctgaacggg    7920
gggttcgtgc acacagccca gcttggagcg aacgacctac accgaactga gatacctaca    7980
gcgtgagcta tgagaaagcg ccacgcttcc cgaagggaga aaggcggaca ggtatccggt     8040
aagcggcagg gtcggaacag gagagcgcac gagggagctt ccaggggaa acgcctggta      8100 tctttatagt cctgtcgggt ttcgccacct ctgacttgag cgtcgattt tgtgatgctc      8160 gtcaggggg cggagcctat ggaaaaacgc cagcaacgcg ccttttttac ggttcctggc      8220 ctttgctgg cctttgctc acatgttctt tcctgcgtta tccctgatt ctgtggataa        8280 ccgtattacc gcctttgagt gagctgatac cgctcgccgc agccgaacga ccgagcgcag     8340
cgagtcagtg agcgaggaag cggaagagag ctc                                  8373
```

<210> SEQ ID NO 2  
<211> LENGTH: 21  
<212> TYPE: DNA  
<213> ORGANISM: Artificial Sequence  
<220> FEATURE:  
<223> OTHER INFORMATION: primer

<400> SEQUENCE: 2
gaaacaatgc caaatatctc t                                               21

<210> SEQ ID NO 3  
<211> LENGTH: 27  
<212> TYPE: DNA  
<213> ORGANISM: Artificial Sequence  
<220> FEATURE:  
<223> OTHER INFORMATION: primer

<400> SEQUENCE: 3
tcattgacat ctggagatgc aggtact                                         27

<210> SEQ ID NO 4  
<211> LENGTH: 18  
<212> TYPE: DNA  
<213> ORGANISM: Artificial Sequence  
<220> FEATURE:  
<223> OTHER INFORMATION: primer

<400> SEQUENCE: 4
acactaactt cgttggtt                                                   18

<210> SEQ ID NO 5  
<211> LENGTH: 24  
<212> TYPE: DNA  
<213> ORGANISM: Artificial Sequence  
<220> FEATURE:  
<223> OTHER INFORMATION: primer

<400> SEQUENCE: 5
aacgtaatgg atatattaaa gtct                                            24

<210> SEQ ID NO 6  
<211> LENGTH: 21  
<212> TYPE: DNA  
<213> ORGANISM: Artificial Sequence

```
<220> FEATURE:
<223> OTHER INFORMATION: primer

<400> SEQUENCE: 6
gaaaacgacg cctctttaaa g                                              21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gaaaaggaag cctccttaaa g                                              21

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
tctcctacat ggaactca                                                  18

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
agaacattac ccacatga                                                  18

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tctcacaatc accactttca t                                              21

<210> SEQ ID NO 11
<211> LENGTH: 526
<212> TYPE: PRT
<213> ORGANISM: Rabies virus

<400> SEQUENCE: 11
```

Met Val Pro Val Pro Gln Ala Leu Leu Asn Val Pro Leu Leu Val Asn
1               5                   10                  15

Pro Leu Cys Asn Gly Lys Phe Pro Ile Tyr Thr Ile Pro Asp Lys Leu
20 25 30

Gly Pro Trp Ser Pro Ile Asp Ile His His Leu Ser Cys Pro Asn Asn
35 40 45

Leu Val Val Glu Asp Glu Gly Cys Thr Asn Leu Ser Gly Phe Ser Tyr
50 55 60

Met Glu Leu Lys Val Gly Tyr Ile Ser Ala Ile Lys Met Asn Gly Phe
65 70 75 80

Thr Cys Thr Gly Val Val Thr Glu Ala Glu Thr Tyr Thr Asn Phe Val

```
                    85                  90                  95
Gly Tyr Val Thr Thr Thr Phe Lys Arg Lys His Phe Arg Pro Thr Pro
                100                 105                 110

Asp Ala Cys Arg Ala Ala Tyr Asn Trp Lys Met Ala Gly Asp Pro Arg
                115                 120                 125

Tyr Glu Glu Ser Leu His Asn Pro Tyr Pro Asp Tyr His Trp Leu Arg
                130                 135                 140

Thr Val Lys Thr Thr Lys Glu Ser Leu Val Ile Ile Ser Pro Ser Val
145                 150                 155                 160

Ala Asp Leu Asp Pro Tyr Asp Arg Ser Leu His Ser Arg Val Phe Pro
                165                 170                 175

Gly Gly Lys Cys Ser Gly Val Ala Val Ser Ser Thr Tyr Cys Ser Thr
                180                 185                 190

Asn His Asp Tyr Thr Ile Trp Met Pro Glu Asn Pro Arg Leu Gly Met
                195                 200                 205

Ser Cys Asp Ile Asn Thr Asn Ser Arg Gly Lys Arg Ala Ser Lys Gly
                210                 215                 220

Ser Glu Thr Cys Gly Asn Val Asp Glu Arg Gly Leu Tyr Lys Ser Leu
225                 230                 235                 240

Lys Gly Ala Cys Lys Leu Gln Leu Cys Gly Val Leu Gly Leu Arg Leu
                245                 250                 255

Met Asp Gly Thr Trp Val Ser Met Gln Thr Ser Asn Glu Thr Lys Trp
                260                 265                 270

Cys Pro Pro Gly Gln Leu Ile Asn Leu His Asp Asn Arg Ser Asp Glu
                275                 280                 285

Ile Glu His Leu Val Val Glu Glu Leu Val Lys Lys Arg Glu Glu Cys
                290                 295                 300

Leu Asp Ala Leu Glu Ser Ile Met Thr Thr Lys Ser Val Ser Phe Arg
305                 310                 315                 320

Arg Leu Ser His Leu Arg Lys Leu Val Pro Gly Asn Gly Lys Ala Tyr
                325                 330                 335

Thr Ile Phe Asn Lys Thr Leu Met Glu Ala Asp Ala His Tyr Lys Ser
                340                 345                 350

Val Arg Thr Trp Asn Glu Ile Ile Pro Ser Lys Gly Cys Leu Arg Val
                355                 360                 365

Gly Gly Arg Cys His Pro His Val Asn Gly Val Asn Phe Asn Gly Ile
                370                 375                 380

Ile Leu Gly Pro Asp Gly Asn Val Leu Ile Pro Glu Met Gln Ser Ser
385                 390                 395                 400

Leu Leu Gln Gln His Met Glu Leu Leu Val Ser Ser Val Ile Pro Leu
                405                 410                 415

Met His Pro Leu Ala Asp Pro Ser Thr Val Phe Lys Asn Gly Asp Glu
                420                 425                 430

Ala Glu Asp Asn Val Glu Val His Leu Pro Asp Val His Glu Arg Ile
                435                 440                 445

Ser Gly Val Asp Leu Gly Leu Pro Asn Trp Gly Lys Tyr Val Leu Leu
                450                 455                 460

Ser Ala Gly Ala Leu Thr Ala Leu Met Leu Ile Ile Phe Leu Met Thr
465                 470                 475                 480

Cys Trp Arg Arg Val Asn Arg Ser Glu Pro Thr Gln His Asn Leu Arg
                485                 490                 495

Gly Thr Gly Arg Glu Val Ser Val Thr Pro Gln Ser Gly Lys Ile Ile
                500                 505                 510
```

Ser Ser Trp Glu Ser Tyr Lys Ser Gly Gly Glu Thr Gly Leu
        515                 520                 525

<210> SEQ ID NO 12
<211> LENGTH: 1018
<212> TYPE: PRT
<213> ORGANISM: Escherichia coli

<400> SEQUENCE: 12

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Trp Arg
            20                  25                  30

Asn Ser Glu Glu Ala Arg Thr Asp Arg Pro Ser Gln Gln Leu Arg Ser
        35                  40                  45

Leu Asn Gly Glu Trp Arg Asn Ala Trp Asn Pro Ala Pro Glu Ala Val
    50                  55                  60

Pro Glu Ser Trp Leu Glu Cys Asp Leu Pro Glu Ala Asp Thr Val Val
65                  70                  75                  80

Val Pro Ser Asn Trp Gln Met His Gly Tyr Asp Ala Pro Ile Tyr Thr
                85                  90                  95

Asn Val Thr Tyr Pro Ile Thr Val Asn Pro Pro Asn Val Pro Thr Glu
            100                 105                 110

Asn Pro Thr Gly Cys Tyr Ser Leu Thr Asn Asn Val Asp Glu Ser Trp
        115                 120                 125

Leu Gln Glu Gly Gln Thr Arg Ile Ile Asn Asp Gly Val Asn Ser Ala
    130                 135                 140

Asn His Leu Trp Cys Asn Gly Arg Trp Val Gly Tyr Gly Gln Asp Ser
145                 150                 155                 160

Arg Leu Pro Ser Glu Asn Asp Leu Ser Ala Asn Leu Arg Ala Gly Glu
                165                 170                 175

Asn Arg Leu Ala Val Met Val Leu Arg Trp Ser Asp Gly Ser Tyr Leu
            180                 185                 190

Glu Asp Gln Asp Met Trp Arg Met Ser Gly Ile Phe Arg Asp Val Ser
        195                 200                 205

Leu Leu His Lys Pro Thr Thr Gln Ile Ser Asp Phe His Val Ala Thr
    210                 215                 220

Arg Asn Asn Asp Asp Phe Ser Arg Ala Val Leu Glu Ala Glu Val Gln
225                 230                 235                 240

Met Cys Gly Glu Leu Arg Asp Tyr Leu Arg Val Thr Val Ser Leu Trp
                245                 250                 255

Gln Gly Glu Thr Gln Val Ala Ser Gly Thr Ala Pro Phe Gly Gly Glu
            260                 265                 270

Ile Ile Asp Glu Arg Gly Gly Tyr Ala Asp Arg Val Thr Leu Arg Leu
        275                 280                 285

Lys Val Glu Asn Pro Lys Leu Trp Ser Ala Glu Ile Pro Asn Leu Tyr
    290                 295                 300

Arg Ala Val Val Glu Leu His Thr Ala Asp Gly Thr Leu Ile Glu Ala
305                 310                 315                 320

Glu Ala Cys Asp Val Gly Phe Arg Glu Val Arg Ile Glu Asn Gly Leu
                325                 330                 335

Leu Leu Leu Asn Gly Lys Pro Leu Leu Ile Arg Gly Val Asn Arg His
            340                 345                 350

Glu His His Pro Leu His Gly Gln Val Met Asp Glu Gln Thr Met Val

-continued

```
                355                 360                 365
Gln Asp Ile Leu Leu Met Lys Gln Asn Asn Asn Ala Val Arg Cys
370                 375                 380

Ser His Tyr Pro Asn His Pro Leu Trp Tyr Thr Leu Cys Asp Arg Tyr
385                 390                 395                 400

Gly Leu Tyr Val Val Asp Glu Ala Asn Ile Glu Thr His Gly Met Val
                405                 410                 415

Pro Ile Asn Arg Leu Thr Asp Asp Pro Arg Trp Leu Pro Ala Met Ser
                420                 425                 430

Glu Arg Val Thr Arg Met Val Gln Arg Asp Arg Asn His Pro Ser Val
                435                 440                 445

Ile Ile Trp Ser Leu Gly Asn Glu Ser Gly His Gly Ala Asn His Asp
                450                 455                 460

Ala Leu Tyr Arg Trp Ile Lys Ser Val Asp Pro Ser Arg Pro Val Gln
465                 470                 475                 480

Tyr Glu Gly Gly Gly Ala Asp Thr Thr Ala Thr Asp Ile Ile Cys Pro
                    485                 490                 495

Met Tyr Ala Arg Val Asp Glu Asp Gln Pro Phe Pro Ala Val Pro Lys
                500                 505                 510

Trp Ser Ile Lys Lys Trp Leu Ser Leu Pro Gly Glu Thr Arg Pro Leu
                515                 520                 525

Ile Leu Cys Glu Tyr Ala His Ala Met Gly Asn Ser Leu Gly Gly Phe
530                 535                 540

Ala Lys Tyr Trp Gln Ala Asn Arg Gln Tyr Pro Arg Leu Gln Gly Gly
545                 550                 555                 560

Phe Val Trp Asp Trp Val Asp Gln Ser Leu Ile Lys Tyr Asp Glu Asn
                565                 570                 575

Gly Asn Pro Trp Ser Ala Tyr Gly Gly Asp Asn Gly Asp Thr Pro Asn
                580                 585                 590

Asp Arg Gln Phe Cys Met Asn Gly Leu Val Asn Ala Asp Arg Thr Pro
                595                 600                 605

His Pro Ala Leu Thr Glu Ala Lys His Gln Gln Gln Asn Phe Gln Phe
610                 615                 620

Arg Leu Ser Gly Gln Thr Ile Glu Val Thr Ser Glu Tyr Leu Phe Arg
625                 630                 635                 640

His Ser Asp Asn Glu Leu Leu His Trp Met Val Ala Leu Asp Gly Lys
                645                 650                 655

Pro Leu Ala Ser Gly Glu Val Pro Leu Asp Val Ala Pro Gln Gly Lys
                660                 665                 670

Gln Leu Ile Glu Leu Pro Glu Leu Pro Gln Pro Glu Ser Ala Gly Gln
                675                 680                 685

Leu Trp Leu Thr Val Arg Val Val Gln Pro Asn Ala Thr Ala Trp Ser
690                 695                 700

Glu Ala Gly His Ile Ser Ala Trp Gln Gln Trp Arg Leu Ala Glu Asn
705                 710                 715                 720

Leu Ser Val Thr Leu Pro Ala Ala Ser His Ala Ile Pro His Leu Thr
                725                 730                 735

Thr Ser Glu Met Asp Asn Cys Ile Glu Leu Gly Asn Lys Arg Trp Gln
                740                 745                 750

Asn Asn Arg Gln Ser Gly Asn Leu Ser Gln Met Trp Ile Gly Asp Lys
                755                 760                 765

Lys Gln Leu Leu Thr Pro Leu Arg Asp Gln Phe Thr Arg Ala Pro Leu
770                 775                 780
```

```
Asp Asn Asp Ile Gly Val Ser Glu Ala Thr Arg Ile Asp Pro Asn Ala
785                 790                 795                 800

Trp Val Glu Arg Trp Lys Ala Ala Gly His Tyr Gln Ala Glu Ala Ala
                805                 810                 815

Leu Leu Gln Cys Thr Ala Asp Thr Leu Ala Asp Ala Val Leu Ile Thr
            820                 825                 830

Thr Gly His Ala Trp Gln His Gln Gly Lys Thr Leu Asn Ile Ser Arg
        835                 840                 845

Lys Thr Tyr Arg Ile Asp Gly Ser Gly Gln Met Ala Ile Thr Val Asp
    850                 855                 860

Val Glu Val Ala Ser Asp Thr Pro His Pro Ala Arg Ile Gly Leu Asn
865                 870                 875                 880

Cys Gln Leu Ala Gln Val Ala Glu Arg Val Asn Trp Leu Gly Leu Gly
                885                 890                 895

Pro Gln Glu Asn Tyr Pro Asp Arg Leu Thr Ala Ala Cys Asn Asp Arg
            900                 905                 910

Trp Asp Leu Pro Leu Ser Asp Met Tyr Thr Pro Tyr Val Phe Pro Ser
        915                 920                 925

Glu Asn Gly Leu Arg Cys Gly Thr Arg Glu Leu Asn Tyr Gly Pro His
    930                 935                 940

Gln Trp Arg Gly Asp Phe Gln Phe Asn Ile Ser Arg Tyr Ser Gln Gln
945                 950                 955                 960

Gln Leu Met Glu Thr Ser His Arg His Leu Leu His Ala Glu Glu Gly
                965                 970                 975

Thr Trp Leu Asn Ile Asp Gly Phe His Met Gly Ile Gly Gly Asp Asp
            980                 985                 990

Ser Trp Ser Pro Ser Val Ser Ala Glu Phe Gln Leu Ser Ala Val Arg
        995                 1000                1005

Tyr His Tyr Gln Leu Val Trp Cys Gln Lys
    1010                1015

<210> SEQ ID NO 13
<211> LENGTH: 286
<212> TYPE: PRT
<213> ORGANISM: Escherichia coli

<400> SEQUENCE: 13

Met Ser Ile Gln His Phe Arg Val Ala Leu Ile Pro Asn Asn Ala Ala
1               5                   10                  15

Asn Cys Leu Pro Val Asn Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Asn Arg Pro Glu Glu Arg Asn
    50                  55                  60

Pro Met Met Ser Thr Asn Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
```

-continued

```
                130                 135                 140
Glu Leu Thr Ala Asn Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
                195                 200                 205

Met Glu Ala Asp Lys Val Ala Gly Pro Leu Leu Arg Ser Ala Leu Pro
        210                 215                 220

Ala Gly Trp Asn Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
        275                 280                 285
```

RACCOON POXVIRUS EXPRESSING RABIES GLYCOPROTEINS

CROSS-REFERENCE TO RELATED APPLICATIONS

This application claims the benefit under 35 U.S.C. §119 (e) of U.S. Provisional Application No. 60/932,492 filed May 30, 2007, the disclosure of which is incorporated by reference herein in its entirety.

FIELD OF THE INVENTION

The present invention concerns a recombinant raccoon poxvirus vector that uniquely expresses the rabies glycoprotein genes of at least two different rabies strains inserted into thymidine kinase (tk) and hemagglutinin (ha) loci of the raccoon poxvirus genome. The present invention is useful as a vaccine in the prophylaxis of neurological disease and death caused by the rabies virus.

BACKGROUND OF THE INVENTION

The rabies virus is a non-segmented, single-stranded, linear RNA rhabdovirus or lyssavirus with negative sense polarity of the family Rhabdoviridae, which has a bullet-like shape having one round or conical end while the other end is planar or concave in shape. The round or conical end of the virion possesses a lipoprotein envelope with knob-like spikes composed of glycoprotein G. In addition to glycoprotein G, the lipid membrane or viral envelope surrounding the core structure has a second, inner layer consisting of a matrix protein (M). The external surface glycoprotein G is responsible for cell attachment and has been identified as the antigenic substance that is responsible for the virulence or pathogenicity of the rabies virus as well as the host immune response.

With few exceptions, rabies invariably results in fatal neurological disease in humans and animals, and remains a serious global public health concern. The majority of human deaths stemming from rabies have occurred in Africa, Asia and South America but a rabies epidemic has also recently become problematic in the United States due to a rapidly growing population of infected raccoons. Other primary virus carriers of concern are the skunk, largely in the mid-western states, and bats, the main source for most human cases in the U.S. In addition to the infected wildlife such as the raccoons, skunks, foxes, wolves, etc., humans typically become infected with rabies through the bite of infected dogs and cats. Dogs continue to be the main hosts of the rabies virus in Africa and Asia where canine rabies is endemic and are still responsible for most of the human deaths that occur from rabies worldwide. It is of particular importance to mankind, therefore, to prevent the rabies virus infection in domestic pets such as dogs, cats and ferrets.

Louis Pasteur and Emile Roux developed the first rabies vaccination in 1885. The early nerve tissue-derived vaccine consisted of a virus sample taken from infected rabbits and dried to weaken its pathogenicity. Some developing countries still use comparable neural tissue rabies vaccines and, although much less expensive than modern cell culture vaccines, they are not nearly as effective and carry a significant risk of neurological side effects.

In 1967, the human diploid cell rabies vaccines (HDCV) were developed for human vaccination using the attenuated Pitman-Moore L503 strain of the virus. Now available on the market are less expensive, highly purified chick embryo culture vaccine (PCEC) and purified Vero cell rabies vaccine. The latter Vero cell culture vaccine uses the attenuated Wistar strain of the rabies virus while the Vero cell line is its host. Despite the attenuation, the Vero cell culture vaccine has the potential to revert to virulence. Consequently, preparation of the rabies vaccine requires extreme care by the workers to avoid the accidental dissemination of viral infections with the strain as a result of a rabies virus surviving the inactivation process. The PCEC vaccine has the added disadvantage that it cannot be given to anyone with an allergy to eggs or chickens. Additional difficulties handling, manufacturing or using live rabies virus in vaccines are well known to those in the pharmaceutical and veterinary arts.

In view of the disadvantages of conventional rabies viral vaccines, research has been aimed at the use of recombinant raccoon poxviruses and the insertion of foreign genes such as the rabies virus glycoprotein genes into the thymidine kinase (tk) locus of raccoon poxviruses. It was found that certain early constructs of recombinant raccoon poxviruses could express the foreign viral antigenic substance or foreign DNA and elicit host protective immune responses in other animals such as dogs and cats. However, the construction of safe and effective recombinant raccoon poxviruses to be useful as vaccines is a complex matter and involves many factors that must be taken into consideration. In particular, the ability to create recombinant raccoon poxviruses varying the position of the exogenous or foreign genes inserted into different regions beyond the known tk locus as well as the particular selection of functional foreign antigenic DNA fragments require significant experimental studies to determine the stability, the safety and the efficacy of the resultant recombinant poxviruses. Several attempts, therefore, to obtain a commercially viable recombinant raccoon poxvirus vaccine have been the focus of numerous efforts in the veterinary vaccine field.

As such, there is a significant amount of published information on the topic of recombinant raccoon poxvirus as vaccines. More recently, for instance, an oral genetically recombined virus vaccine for raccoon rabies has been described in U.S. Patent Application No. 2005/0282210. A gene that produces a protein in the rabies viral outer coat was inserted into a live vaccinia virus using recombinant DNA technology. When the modified vaccinia virus infects a normal animal, it produces the antigenic protein normally made by the rabies virus. The biological system of the victim recognizes the protein as foreign; and the animal develops active immunity. Specifically, Patent Application No. 2005/0282210 is drawn to a method of eliciting an immune response in a skunk or mongoose which involves administering a composition that consists of a viral vector comprising a rabies surface glycoprotein gene that has been inserted into the viral vector genome of the vaccinia. The disclosure suggests the potential insertion sites for the polynucleotide or polynucleotides to be expressed at the thymidine kinase (tk) gene or insertion site, the hemagglutinin (ha) gene or insertion site, or the region encoding the inclusion body of the A type (ATI) of a vaccinia virus; ORF(s) C3, C5 and/or C6 in the case of canarypox virus; ORFs F7 and/or F8 in the case of fowlpox virus but the document only exemplifies the use of the vaccinia virus vector in which the rabies glycoprotein G is derived from the ERA strain and is inserted only in the tk site of the vaccinia.

U.S. Pat. No. 7,074,413 discloses the design of recombinant rabies virus vaccines by replacing the glycoprotein of a non-neuroinvasive rabies strain with that of a street or neuroinvasive rabies virus to produce an attenuated recombinant rabies virus for vaccination or constructing a recombinant rabies virus expressing a pro-apoptotic protein.

U.S. Pat. No. 6,719,981 shows attenuated rabies virus mutants and live attenuated anti-rabies vaccines comprising said mutants in which the recombinant rabies virus mutant of a Street Alabama Dufferin strain (SAD D29) comprises a mutation in the G protein of the viral genome, wherein said mutation comprises a particular substitution of a AGA codon encoding $Arg_{333}$ with a GAC codon.

U.S. Pat. No. 6,294,176 relates to a recombinant raccoon poxvirus vaccine that consists of a raccoon poxvirus viral genome which contains a foreign DNA sequence inserted into a non-essential region within the HindIII "U" genomic region, the HindIII "M" genomic region or the HindIII "N" genomic region of the raccoon poxvirus genome. The raccoon poxvirus viral genome is described in the patent as containing a deletion in the raccoon poxvirus host range gene of the viral genome. The patent provides a homology vector for producing the recombinant raccoon poxvirus by inserting the foreign DNA sequence into the raccoon poxvirus genome. While there is the broad suggestion that the recombinant raccoon poxvirus may contain foreign DNA encoding an antigenic polypeptide from the rabies virus, there is no exemplification relevant thereto. In addition, DNA sequence analysis indicates that the HindIII "U" genomic region disclosed by the patentees is not the hemagglutinin (ha) insertion and/or the thymidine kinase (tk) regions of the recombinant raccoon poxvirus genome.

U.S. Pat. No. 6,241,989 and its continuation U.S. Pat. No. 7,087,234 deal with multivalent recombinant raccoon poxviruses, containing more than one exogenous gene inserted into either the thymidine kinase gene or the hemagglutinin gene. Disclosed in these patents is the use of the multivalent recombinant raccoon poxviruses as vaccines to immunize felines against feline pathogens. Also disclosed is a method of making a multivalent recombinant raccoon poxvirus by a recombinant process involving the construction of an insertion vector into which the exogenous genes are inserted; and flanking the inserted genes are sequences which can recombine into the raccoon poxvirus thymidine kinase gene or the hemagglutinin gene; introducing both the insertion vector containing the exogenous genes, and raccoon poxvirus into susceptible host cells; and selecting the recombinant raccoon poxvirus from the resultant plaques. The multivalent, recombinant raccoon poxvirus of the patents can infect and replicate in feline cells, and contains more than one exogenous gene inserted into a region consisting of a hemagglutinin gene or a thymidine kinase gene of the raccoon poxvirus genome which is non-essential for viral replication and each exogenous gene encodes a feline pathogen antigen. The patents describe exogenous genes encoding feline pathogen antigens such as feline leukemia virus (FeLV Env), feline immunodeficiency virus (FIV Gag), feline immunodeficiency virus (FIV Env), feline infectious peritonitis virus (FIPV M), feline infectious peritonitis virus (FIPV N), feline calicivirus (FCV capsid protein), feline panleukopenia virus (FPV VP2) and rabies-G.

Although U.S. Pat. Nos. 6,241,989 and 7,087,234 suggest that both the thymidine kinase (tk) gene and the hemagglutinin (ha) gene of the raccoon poxvirus genome can be used for insertion of exogenous genes by recombination, the specific examples only show how to generate a multivalent RCNV-based recombinant FPV VP2 and rabies virus (RCNV/FPV/RAB-G) by homologous recombination of the flanked vaccinia virus tk gene sequence and a separate homologous recombinant raccoon poxvirus containing FCV capsid protein gene inserted into the ha gene. There are no claims or exemplification teaching how to construct and/or use a recombinant raccoon poxvirus containing multiple foreign antigenic material on both thymidine kinase and the hemagglutinin genes. Moreover, the patents do not teach or disclose any recombinant constructs having the rabies virus glycoprotein gene inserted into the ha site of the raccoon poxvirus genome.

U.S. Pat. No. 6,106,841 relates to a method for immunizing an animal against a heterologous antigen. The method describes administering to the animal via the conjunctival route, a composition comprising a recombinant raccoon poxvirus having a nucleic acid molecule encoding the heterologous antigen. Antigens are described as calicivirus, coronavirus, herpesvirus, immunodeficiency virus, infectious peritonitis virus, leukemia virus, parvovirus antigen, rabies virus, Bartonella, Yersinia, Dirofilaria, Toxoplasma, flea antigen or flea allergen, midge antigen or allergen, mite antigen or allergen and a tumor antigen. The patent further discloses a recombinant raccoon poxvirus that comprises a nucleic acid molecule encoding an immunomodulator such as granulocyte macrophage colony stimulating factor (GM-CSF), granulocyte colony stimulating factor (G-CSF), macrophage colony stimulating factor (M-CSF), colony stimulating factor (CSF), interleukins, interferon gamma and the like. Also described therein are methods using a recombinant raccoon poxvirus genome having a heterologous nucleic acid molecule in the raccoon poxvirus gene selected from thymidine kinase, hemagglutinin, serpin, cytokine receptor and interferon receptor genes in which the heterologous nucleic acid molecule is operatively linked to a transcription control sequence consisting of a p11 poxvirus promoter, a p7.5 poxvirus promoter or a synthetic poxvirus promoter.

U.S. Pat. No. 6,024,953 describes a vaccinia virus that contains all or part of a DNA sequence coding for an antigenic glycoprotein of rabies. In particular, the patent discloses a hybrid vaccinia virus containing a DNA sequence which encodes the amino acid sequence of rabies glycoprotein G that has been inserted in a vaccinia thymidine kinase (tk) gene under the control of the 7.5 K vaccinia virus promoter and a vaccine for preventing and treating rabies that consists of the hybrid vaccinia virus and a pharmaceutically acceptable carrier.

U.S. Pat. No. 5,348,741 deals with a plasmid vector that has been constructed with recombinant DNA comprising a rabies virus glycoprotein G gene operatively linked to a vaccinia $P_{11}$ late promoter. The rabies virus glycoprotein G gene is derived from Challenge Virus Standard strain. The gene and the promoter are inserted into the thymidine kinase (tk) locus of the vaccinia or cowpox virus vector. The patent states that the recombinant vaccinia virus expresses the gene for rabies virus glycoprotein in cells and induces production of glycoprotein for immunization against rabies. The patent indicates that the recombinant virus could be applied for the production of anti-rabies vaccine and of G antigen antibody and related immunological reagents for research or diagnostic purposes. Notably, the patent does not describe inserting the rabies virus glycoprotein G gene into any other site besides the tk locus and does not give any suggestion of using a raccoon poxvirus as the vector.

An early DNA rabies vaccine is described in U.S. Pat. No. 5,830,477, which relates to a vaccinia virus that contains all or part of a DNA sequence coding for an antigenic glycoprotein of rabies. The patent concerns an oral vaccine for preventing or treating rabies in a mammal consisting of a hybrid vaccinia virus that contains and expresses a DNA sequence encoding the amino acid sequence rabies glycoprotein G wherein the DNA sequence is present in a non-essential segment of the vaccinia virus and a pharmaceutically acceptable carrier. Specifically, the patent only exemplifies a hybrid vaccinia virus vaccine in which the rabies glycoprotein G is under the control of a 7.5K vaccinia promoter and is present in the vaccinia thymidine kinase (tk) gene.

U.S. Pat. No. 5,266,313 relates to the use of raccoon poxvirus as a substrate for insertion and expression of the nucleotide coding sequence of heterologous organisms. The patent describes the production of two infectious raccoon poxvirus recombinants for expressing rabies virus surface spike glycoprotein (G) by homologous recombination between raccoon poxvirus DNA and chimeric plasmids used for production of vaccinia virus recombinants by thymidine kinase (tk) insertional inactivation.

Also of interest as background material to the present invention are previous patents relating to the common use of promoters, namely, those sequences that positively regulate the transcription of a gene such as the promoters used with the foreign gene protein coding sequence that comprises the foreign gene or exogenous gene material that is being inserted and expressed by a recombinant vector. For example, U.S. Pat. No. 6,998,252 concerns recombinant poxviruses, such as vaccinia, that comprise a first DNA sequence encoding a polypeptide that is foreign to poxvirus and a poxvirus transcriptional regulatory sequence, wherein the transcriptional regulatory sequence is adjacent to and exerts transcriptional control over the DNA sequence and the segment is positioned within a nonessential genomic region of the recombinant poxvirus. Construction of plasmids containing the promoter from the 7.5K polypeptide gene (7.5K gene) of vaccinia virus, the restriction endonuclease sites for insertion of foreign protein coding sequences and the interrupted vaccinia virus thymidine kinase (tk) gene as flanking DNA are shown.

U.S. Pat. No. 7,045,313 similarly relates to methods and compositions for the use of vaccinia virus or other poxviruses as vectors for expression of foreign genes in which the expression is obtained by combining the vaccinia virus transcriptional regulatory sequence with uninterrupted foreign protein coding sequences in vitro to form a chimeric gene. The patent shows how the chimeric gene is flanked by DNA from a non-essential region of the vaccinia virus genome to provide sites for in vivo homologous recombination. These steps are facilitated in the patent disclosure by the construction of plasmids that contain multiple restriction endonuclease sites, next to the vaccinia transcriptional regulatory sequences, for insertion of the foreign protein coding sequence. The patent further shows the plasmids comprising a segment comprised of a first DNA sequence encoding a polypeptide that is foreign to vaccinia virus and a vaccinia virus promoter sequence, wherein said promoter sequence is adjacent to and exerts transcriptional control over said first DNA sequence; and, flanking said segment, DNA from a nonessential region of a vaccinia genome. Specifically, the promoter sequence is one that in vaccinia virus regulates the thymidine kinase (tk) gene or a vaccinia gene encoding a 7.5 K polypeptide. Transfection procedures are illustrated therein to introduce the DNA into cells where homologous recombination results in the insertion of the chimeric gene into a non-essential region of the vaccinia virus genome.

Also relevant to standard promoters known in the art, U.S. Pat. No. 7,208,313 relates to vaccinia virus expression vectors produced with a negative thymidine kinase (tk) phenotype and a negative vaccinia virus growth factor phenotype. The foreign gene is placed under the control of a vaccinia virus promoter and integrated into the genome of the mutant vaccinia virus. Alternatively, expression can be achieved by transfecting a shuffle vector or plasmid containing the vaccinia promoter-controlled gene into a cell that has been infected with vaccinia virus and introducing the exogenous sequence by homologous recombination.

Synthetic early-late vaccinia virus promoters are illustrated in U.S. Pat. Nos. 6,183,750; 7,067,248 and others. U.S. Pat. No. 6,183,750 describes a recombinant poxvirus, such as vaccinia virus, fowipox virus or canarypox virus, containing foreign DNA from herpesvirus and a promoter operably linked to the DNA for expressing the DNA, wherein the promoter is superimposed on or ligated to the initiation codon of the DNA. The promoter-gene linkage is positioned in the plasmid construct so that the linkage is flanked on both ends by DNA homologous to a DNA sequence flanking a region of pox DNA containing a nonessential locus. A condition for expression of inserted DNA is the presence of the promoter in the proper relationship to the inserted DNA, that is, the promoter should be placed so that it is located upstream from the DNA sequence to be expressed. U.S. Pat. No. 7,067,248 additionally shows ways to use a synthetic early-late promoter to express a substrate protein from vaccinia virus. See also S. Chakrabarti et al., "Compact, Synthetic, vaccinia virus early/late promoter for protein expression," BioTechniques 23: 1094-1097 (1997).

Other material relevant to the background of the present invention can be found in the following literature citations: A. D. Alexander et al, "Survey of wild mammals in a Chesapeake Bay area for selected zoonoses," J. Wildlife Dis. 8: 119-126 (1972); C. Bahloul et al., "DNA-based immunization for exploring the enlargement of immunological cross reactivity against the lyssaviruses," Vaccine 16: 417-425 (1998); S. Chakrabarti et al., "Compact, Synthetic, vaccinia virus early/late promoter for protein expression," BioTechniques 23: 1094-1097 (1997); J. C. DeMartini et al., "Raccoon poxvirus rabies virus glycoprotein recombinant vaccine in sheep," Arch. Virol. 133: 211-222 (1993); B. Dietzschold et al., "Rhabdoviruses," In: Fields Viology, ed. B. N. Fields et al., 3rd edition, New York: Raven Press, pp. 1137-1159 (1996); J. J. Esposito et al., "Vaccinia virus recombinants expressing rabiesvirus glycoprotein protect against rabies," Virus Genes 1: 7-21 (1987); J. J. Esposito et al., "Successful oral rabies vaccination of raccoon poxvirus recombinants expressing rabies virus glycoprotein" Virology 165: 313-316 (1988); J. J. Esposito, "Live poxvirus-vectored vaccines in wildlife immunization programmes: the rabies paradigm. Res. Virol. 140: 480-482 (1989); J. J. Esposito et al., "Oral Immunization of Animals with Raccoon Poxvirus Expressing Rabies Virus Glycoprotein," In: Vaccines 89, eds. R. Lerner, H. Ginsberg, R. M. Chanock and F. Brown, Cold Spring Harbor Laboratory Press, Cold Spring Harbor, N.Y., pp. 403-408 (1989); J. J. Esposito et al., "Raccoon Poxvirus Rabies-Glycoprotein Recombinant Oral Vaccine for Wildlife: Further Efficacy and Safety Studies and Serosurvey for Raccoon Poxvirus," In: Vaccines 92, eds. F. Brown, R. M. Chanock, H. S. Ginsberg and R. A. Lerner, Cold Spring Harbor Laboratory Press, Cold Spring Harbor, N.Y., pp. 321-329 (1992); Y. F. Herman, "Isolation and characterization of a naturally occurring pox virus of raccoons," In: Bacteriol. Proc., 64th Annual Meeting of the American Society for Microbiology, p. 117 (1964); L. Hu et al., "Raccoon poxvirus live recombinant feline panleukopenia virus VP2 and rabies virus glycoprotein bivalent vaccine," Vaccine 15: 1466-1472 (1996); L. Hu et al., "Raccoon poxvirus feline panleukopenia virus VP2 recombinant protects cats against FPV challenge," Virology 218:248-252 (1997); R. I. Macfarlan et al., "Stimulation of cytotoxic T-lymphocyte responses by rabies virus glycoprotein and identification of an immunodominant domain," Mol. Immunol. 23: 733-741 (1986); J. E. Osorio et al., "Recombinant raccoon pox vaccine protests mice against lethal plaque," Vaccine 21: 1232-1238

(2003); P. Perrin et al., "Rabies immunosome (subunit vaccine) structure and immunogenicity. Pre- and post-exposure protection studies," Vaccine 3: 325-332 (1985); S. J. Spatz et al., "Immunological characterization of the feline herpesvirus-1 glycoprotein B and analysis of its deduced amino acid sequence," Virology 197: 125-136 (1993); S. J. Spatz et al., "Identification of the feline herpesvirus type 1 (FHV-1) genes encoding glycoproteins G, D, I and E: expression of FHV-1 glycoprotein D in vaccinia and raccoon poxviruses," J. Gen. Virol. 75: 1235-1244 (1994); J. Taylor et al., "Efficacy studies on a canarypox-rabies recombinant virus," Vaccine 9: 190-192 (1991); E. K. Thomas et al., "Further characterization of raccoonpox virus," Arch. Virol. 49:217-227 (1975); E. Yelverton et al., "Rabies virus glycoprotein analogs: Biosynthesis in *Escherichia coli*," Science 219: 614-620 (1983).

Compared to conventional inactivated rabies vaccines, successful development of a safe and effective, adjuvant-free raccoon poxvirus-vectored rabies vaccine would result in important advantages in avoiding adjuvant-associated sarcoma side effects in cats, ensuring employee safety during vaccine production and completely eliminating any chance of rabies virus surviving inactivation and decontamination procedures used in commercial production. An art-recognized need still exists for a safe and effective rabies virus vaccine for household pets that would adequately protect the pets from being infected with the rabies virus and, in turn, protect their human owners from fatal infections. Also needed is a viable method for the prevention of rabies and the amelioration of harmful neurological effects in mammals.

The foregoing objects are accomplished by providing a safe and efficacious recombinant rabies vaccine that results in long-lasting immunity in dogs and cats in the form of the new raccoon poxvirus vector construct of a rabies vaccine as described herein.

All patents and publications cited in this specification are hereby incorporated by reference in their entirety.

SUMMARY OF THE INVENTION

In its broadest aspect, the present invention provides a new, highly immunogenic recombinant raccoon poxvirus vector (rRCNV) comprising two or more exogenous nucleic acid molecules, each encoding at least one rabies virus glycoprotein, wherein at least two of the nucleic acid molecules are inserted into the hemagglutinin (ha) locus or the thymidine kinase (tk) locus, or at least one of the nucleic acid molecules is inserted into each of the hemagglutinin and thymidine kinase loci, the antigens may come from at least two different rabies virus strains. When two exogenous nucleic acids are inserted into the same locus, they can be contiguous or separated by intervening sequences. The novel recombinant raccoon poxvirus vector vaccine can express exogenous or foreign glycoprotein genes of a rabies virus, at the hemagglutinin (ha) locus or at the thymidine kinase (tk) locus of the poxvirus genome or at both the thymidine kinase (tk) and the hemagglutinin (ha) loci of the poxvirus genome. Beneficially, a new and highly preferred recombinant virus construct of the present invention expresses the rabies glycoproteins (G2) of Challenge Virus Standard (CVS) and Pasteur-Paris (PV) strains at tk and ha loci, respectively. While the source of the nucleic acid molecules encoding the rabies virus glycoprotein may come from the same strain of rabies virus, preferably the genes of at least two different rabies strains are inserted at the thymidine kinase (tk) and the hemagglutinin (ha) loci of the poxvirus genome. The broad spectrum recombinant raccoon poxvirus vectors of this invention are useful as adjuvant-free vaccines. The recombinant vaccine may desirably contain a mixture of other feline and canine antigens for effective immunization of animals. Also disclosed are methods for inducing an immune response to rabies in a mammal which comprises administering to the mammal an effective immunizing amount of the vaccine of the present invention.

Accordingly, a first aspect of the invention provides a recombinant raccoon poxvirus vector (rRCNV) comprising two or more exogenous nucleic acid molecules, each encoding at least one rabies virus glycoprotein, wherein at least two of the nucleic acid molecules are inserted into the hemagglutinin (ha) locus or the thymidine kinase (tk) locus, or at least one of the nucleic acid molecules is inserted into each of the hemagglutinin and thymidine kinase loci.

In one embodiment, the recombinant raccoon poxvirus vectored construct further comprises a nucleic acid molecule encoding a rabies glycoprotein that is inserted into a third non-essential site of the raccoon poxvirus genome in addition to the thymidine kinase and the hemagglutinin loci of the raccoon poxvirus genome.

In one embodiment, the third non-essential site of the raccoon poxvirus genome is the serine protease inhibitor site.

In one embodiment, the two nucleic acid molecules encoding a rabies virus glycoprotein are isolated from the same strain of rabies virus.

In one embodiment, the two nucleic acid molecules encoding a rabies virus glycoprotein are isolated from a different strain of rabies virus.

In one embodiment, the source of a rabies virus glycoprotein is selected from the group consisting of a Challenge Virus Standard rabies strain, a Pasteur-Paris rabies strain, a canine rabies street virus, an Arctic Fox rabies virus, a raccoon rabies virus and a bat rabies virus.

In one embodiment, the nucleic acid molecule encoding the glycoprotein that is inserted at the thymidine kinase locus of the raccoon poxvirus genome is from the Challenge Virus Standard rabies strain.

In one embodiment, the nucleic acid molecule encoding the glycoprotein that is inserted at the hemagglutinin locus of the raccoon poxvirus genome is from the Pasteur-Paris rabies strain.

In one embodiment, the raccoon poxvirus is live and replicable.

In one embodiment, the recombinant raccoon poxvirus vector further comprises a nucleic acid molecule encoding a rabies virus glycoprotein that is inserted into a third non-essential site of the raccoon poxvirus genome in addition to the thymidine kinase and the hemagglutinin loci of the raccoon poxvirus genome.

In one embodiment, the third non-essential site of the raccoon poxvirus genome is the serine protease inhibitor site.

A second aspect of the invention provides a recombinant rabies vaccine comprising an immunologically effective amount of any one of the recombinant raccoon poxvirus vectors as described herein and, optionally, a suitable carrier or diluent.

In one embodiment, the recombinant rabies vaccine comprises an immunologically effective amount of two or more of the recombinant raccoon poxvirus vectors as described herein and, optionally, a suitable carrier or diluent.

In one embodiment, the multivalent vaccine only contains one vector construct.

In one embodiment, the invention provides a recombinant rabies vaccine comprising one or more nucleic acid molecules, wherein each nucleic acid molecule encodes a rabies antigen, wherein:

a) at least one nucleic acid molecule is inserted into the hemagglutinin locus or the thymidine kinase locus of the raccoon poxvirus genome; or b) at least two nucleic acid molecules are inserted into the hemagglutinin locus or the thymidine kinase locus of the raccoon poxvirus genome; or c) at least one nucleic acid molecule is inserted into the hemagglutinin locus and at least one nucleic acid molecule is inserted into the thymidine kinase locus of the raccoon poxvirus genome.

In one embodiment, the recombinant rabies vaccine further comprises a mixture with one or more feline antigens selected from the group consisting of feline calicivirus, *Chlamydophila felis*, feline leukemia virus, feline panleukopenia virus, feline rhinotracheitis virus, feline immunodeficiency virus, feline infectious peritonitis virus and *Bartonella* bacteria.

In one embodiment, the recombinant rabies vaccine further comprises a mixture with one or more canine antigens selected from the group consisting of *Ehrlichia canis*, canine parvovirus, canine distemper, canine parainfluenza virus, canine adenovirus type II, canine adenovirus, canine coronavirus, *Leptospira icterohemorrhagiae, Leptospira canicola, Leptospira grippotyphosa* and *Leptospira* Pomona.

In one embodiment, the recombinant rabies vaccine is adjuvant-free.

In one embodiment, the recombinant rabies vaccine further comprises an adjuvant.

In one embodiment, the adjuvant comprises a mixture of an ethylene/maleic copolymer and an acrylic acid copolymer emulsion.

A third aspect of the invention provides a method for inducing a protective immune response to rabies in a mammal comprising administering to the mammal an effective immunizing amount of any one of the vaccines as described herein.

In one embodiment, the invention provides for inducing a protective immune response to rabies in a cat by administering to the cat an effective immunizing amount of any of the vaccines as described herein, but desirably without any adjuvants.

In one embodiment, the invention provides for inducing a protective immune response to rabies in a dog by administering to the dog an effective immunizing amount of any of the vaccines as described herein.

In one embodiment, the invention provides for inducing a protective immune response to rabies in cattle or horses by administering to the cattle or horses an effective immunizing amount of any of the vaccines as described herein.

In one embodiment, the protective immune response is a humoral or antibody mediated response.

In one embodiment, the protective immune response is a cell-mediated or T cell mediated immune response.

In one embodiment, the protective immune response is induced by administering a vaccine dose that ranges from about 4.5 $Log_{10}TCID_{50}$/ml to about 6.7 $Log_{10}TCID_{50}$/ml.

In one embodiment, the protective immune response is induced by administering a vaccine dose that ranges from about 5.38 $Log_{10}TCID_{50}$/ml to about 6.28 $Log_{10}TCID_{50}$/ml.

In one embodiment, the protective response is induced by administering the vaccine as a single dose or as repeated doses.

A fourth aspect of the invention provides a method of making a recombinant raccoon poxvirus vector, comprising the following steps:

(a) inserting a nucleic acid sequence encoding a glycoprotein of a first rabies strain into the thymidine kinase locus of the raccoon poxvirus genome;

(b) inserting a nucleic acid sequence encoding a glycoprotein of a second rabies strain into the hemagglutinin locus of the raccoon poxvirus genome; and (c) recovering the recombinant raccoon poxvirus vector.

In one embodiment, the nucleic acid sequences of steps (a) and (b) further comprise a promoter sequence operably linked to the nucleic acid sequences to allow expression of the nucleic acid and production of the glycoprotein of the first and second rabies strains by the recombinant raccoon poxvirus vector.

In one embodiment, the first rabies strain is a Challenge Virus Standard rabies strain.

In one embodiment, the second rabies strain is a Pasteur-Paris rabies strain.

A fifth aspect of the invention provides a plasmid pFD2003-GPV-PV having the nucleotide sequence of SEQ ID NO: 1.

BRIEF DESCRIPTION OF THE DRAWINGS

The background of the invention and its departure from the art will be further described herein below with reference to the accompanying drawings, wherein:

FIGS. 1A-1M (which corresponds to SEQ ID NO:1) shows the complete sequence of plasmid pFD2003SEL-GPV-PV (8373 nucleotides) in which the RCNV HA-L fragment comprises base pair positions 1-557, the $P_{SEL}$ (synthetic early-late) promoter region runs base pair positions 2153-2195 C, the rabies Pasteur-Paris G gene encompasses base pair positions 570-2150 C, the vv $P_{7.5}$ early promoter region spans base pair positions 2202-2468, lacZ ORF reporter gene covers base pair positions 2469-5525, RCNV HA-R fragment embraces base pair positions 5532-6123 and the ampicillin ORF include base pair positions 6566-7426.

FIGS. 5A-5B and 5C shows the agarose gel electrophoresis for the PCR identity testing of rRCNV-rabies-G2 MSV and X+5 for the ha locus (FIG. 5A) and the tk locus (FIG. 5B). The DNA template for the samples, including controls, used rRCNV-Rabies G2. MSV in Lane 2; rRCNV-Rabies G2, X+5 in Lane 3; DNA Purification Negative Control-01 in Lane 4; DNA Purification Negative Control-02 in Lane 5; PCR Negative Control (water) in Lane 6; PCR Positive Control (RCNV Esposito −3 dilution) in Lane 7; rRCNV-Rabies G2, MSV in Lane 8; rRCNV-Rabies G2, X +5 in Lane 9; DNA Purification Negative Control-01 in Lane 10; DNA Purification Negative Control-02 in Lane 11; PCR Negative Control (water) in Lane 12; and PCR Positive Control (RCNV Esposito −3 dilution) in Lane 13. Lambda/Hind III Marker was in Lane 1 and 1kb DNA Ladder Marker was in Lane 14. For Lanes 2-7, the primers for Gel A (FIG. 5A) were HA-08. HA-Pat; the primers for Gel B (FIG. 5B) were TK-LW, TK-RW; and the target gene was wt ha/tk. For Lanes 8-13, the primers for Gel A (FIG. 5A) were HA-Pst, gp-1F; the primers for Gel B (FIG. 5B) were TK-RR, gJE-F1; and the target gene was Rabies G. As shown in FIG. 5C, the PCR was negative in Lanes 2-6 and 10-13 while PCR was positive in Lanes 7-9.

FIG. 7 shows the agarose gel electrophoresis of the PCR product containing the full length rabies G genes. The samples being tested, including controls, comprised rRCNV-Rabies G2 MSV in Lane 2; rRCNV-Rabies G2 X+5 in Lane 3; Negative control (water) in Lane 4; rRCNV-Rabies G2 MSV in Lane 5; rRCNV-Rabies G2 X+5 in Lane 6; and negative control (water) in Lane 7; with Lambda/HindIII Marker in Lane 1 and 1 kb DNA ladder Marker in Lane 8. For Lanes 2-4, the primers were HA-Pst, PW4; and the gene target was the 1806-bp Pasteur-Paris rabies G and its flanking region. For Lanes 5-7, the primers were TK-RR, PW-03; and the gene target was the 1910-bp CVS rabies G and its flanking region. As shown in FIG. 7, the PCR was negative in control Lanes 4 and 7 while the PCR product was positive in Lanes 2, 3, 5 and 6.

FIG. 8A-8B illustrate the screening by blue plaque (Lac$^+$) purification of rRCNV-Rabies G2 MSV and X+5 in Vero cells, in which FIG. 8A represents rRCNV-Rabies G2 MSV (undiluted, $10^0$) and FIG. 8B represents rRCNV-Rabies G2 X+5 ($10^{-4}$ dilution). The results indicated that the rRCNV-Rabies G2 MSV is phenotypically stable under pre-manufacture scale up procedure to passage 5 by blue plaque assay.

DETAILED DESCRIPTION OF THE INVENTION

Figure 2A:
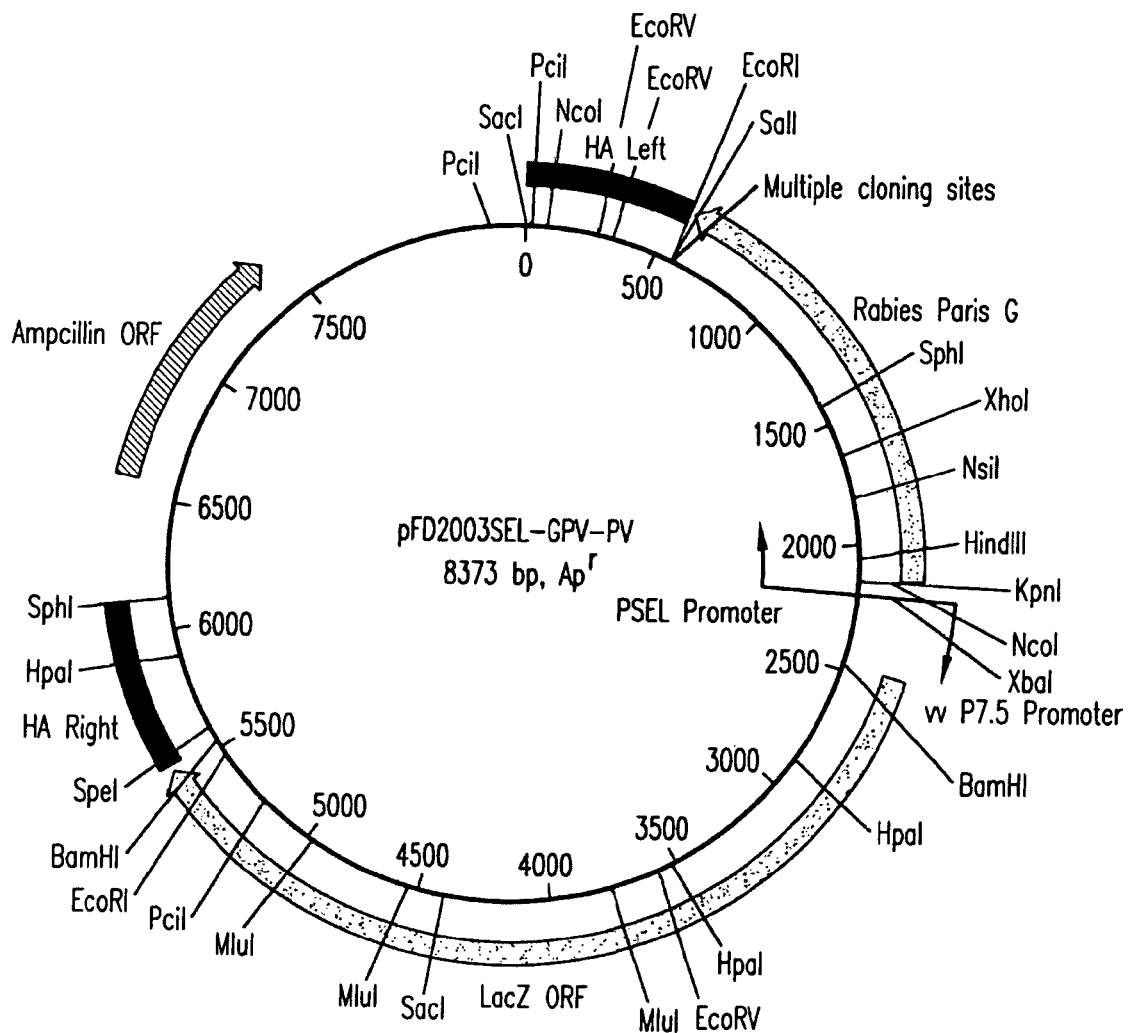
FIGS. 2A and B illustrates the restriction enzyme map of plasmid pFD2003SEL-GPV-PV showing the major restriction enzymes that cut the plasmid between one and three times, namely, BamHI (base pair positions 2471, 5526), EcoRI (positions 558, 5469), EcoRV (positions 265, 324, 3578), HindIII (position 2055), Hpal (positions 2891, 3515, 5895), KpnI (position 2147), MluI (positions 3767, 4547, 4972), NcoI (positions 80, 2147), NsiI (position 1812), PciI (position 24, 5224, 8241), SacI (positions 4405, 8372), SalI (position 564), SpeI (position 5583), SphI (positions 1423, 6128), XbaI (position 2196) and XhoI (position 1633); and the major restriction enzymes that do not cut the plasmid pFD2003-GPV-PV, ie., BglII, KasI, NheI, NotI, NruI, PmeI, PstI, SacII, SmaI and XmaI.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Accordingly, in the present application, there may be employed conventional molecular biology, microbiology, and recombinant DNA techniques within the skill of the art. Such techniques are explained fully in the literature. See, e.g., Byrd, C M and Hruby, D E, Methods in *Molecular Biology*, Vol. 269: Vaccinia Virus and Poxyirology, Chapter 3, pages 31-40; Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Although any methods and materials similar or equivalent to those described herein can be used in the practice or testing of the invention, the preferred methods and materials are now described. All publications mentioned herein are incorporated herein by reference in their entirety.

Definitions

The terms used herein have the meanings recognized and known to those of skill in the art, however, for convenience and completeness, particular terms and their meanings are set forth below.

The term "about" means within 20%, more preferably within 10% and more preferably within 5%.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, Calif., p. 384). Depending on the circumstances, a primary challenge with an antigen alone, in the absence of an adjuvant, may fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable. The term "adjuvant-free" refers to the preparation of any one of the vaccines of the present invention in the absence of an adjuvant, as described above.

"Encoded by" or "encoding" refers to a nucleic acid sequence which codes for a polypeptide sequence, wherein the polypeptide sequence contains an amino acid sequence of at least 3 to 5 amino acids, more preferably at least 8 to 10 amino acids, and even more preferably at least 15 to 20 amino acids, a polypeptide encoded by the nucleic acid sequences. Also encompassed are polypeptide sequences, which are immunologically identifiable with a polypeptide encoded by the sequence. Thus, an antigen "polypeptide," "protein," or "amino acid" sequence may have at least 70% similarity, preferably at least about 80% similarity, more preferably about 90-95% similarity, and most preferably about 99% similarity, to a polypeptide or amino acid sequence of an antigen.

The term "exogenous" refers to a foreign gene or protein encoded by such foreign gene that is produced, originated, derived or developed outside the raccoon poxvirus genome.

An "immune response" to an antigen or vaccine composition is the development in a subject of a humoral and/or a cell-mediated immune response to molecules present in the antigen or vaccine composition of interest. For purposes of the present invention, a "humoral immune response" is an antibody-mediated immune response and involves the generation of antibodies with affinity for the antigen/vaccine of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatibility complex (MHC). This activates antigen-specific CD4+ T helper cells or CD8+ cytotoxic T lymphocyte cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., J. Immunol. (1993) 151:4189-4199; Doe et al., Eur. J. Immunol. (1994) 24:2369-2376.

An "immunologically effective amount" or an "effective immunizing amount", used interchangeably herein, refers to the amount of antigen or vaccine sufficient to elicit an immune response, either a cellular (T cell) or humoral (B cell or antibody) response, as measured by standard assays known to one skilled in the art. In the present invention, an "immunologically effective amount" or an "effective immunizing amount" is a minimal protection dose (titer): 4.5 to 6.7 $Log_{10}TCID_{50}/mL$. The effectiveness of an antigen as an immunogen, can be measured either by proliferation assays, by cytolytic assays, such as chromium release assays to measure the ability of a T cell to lyse its specific target cell, or by measuring the levels of B cell activity by measuring the levels of circulating antibodies specific for the antigen in serum. Furthermore, the level of protection of the immune response may be measured by challenging the immunized host with the antigen that has been injected. For example, if the antigen to which an immune response is desired is a virus or a tumor cell, the level of protection induced by the "immunologically effective amount" of the antigen is measured by detecting the percent survival or the percent mortality after virus or tumor cell challenge of the animals.

As defined herein "a non-essential site" in the raccoon poxvirus genome means a region in the viral genome, which is not necessary for viral infection or replication. Examples of non-essential sites in the raccoon poxvirus genome include, but are not limited to, the thymidine kinase (TK) site, the hemagglutinin (HA) site and the serine protease inhibitor site. The TK site of raccoon poxvirus is described in C. Lutze-Wallace, M. Sidhu and A. Kappeler, Virus Genes 10 (1995), pp. 81-84. The sequence of the TK gene of raccoon poxvirus can also be found in PubMed accession numbers DQ066544 and U08228. The HA site of raccoon poxvirus is described in Cavallaro K F and Esposito, J J, Virology (1992), 190(1): 434-9. The sequence of the HA gene of raccoon poxvirus can also be found in PubMed accession number AF375116.

The term "nucleic acid molecule" or "nucleic acid sequence" has its plain meaning to refer to long chains of repeating nucleotides such as the repeated units of purine and pyrimidine bases that direct the course of protein synthesis, that is, they encode and express the protein substance. As the term is used in the claims, the nucleic acid refers to the known exogenous or foreign genes that encode the rabies virus glycoprotein.

A coding sequence is "operably linked" to a transcriptional and translational control sequence in a cell when RNA polymerase transcribes the coding sequence into mRNA, which is then trans-RNA spliced and translated into the protein encoded by the coding sequence.

A "protective" immune response refers to the ability of a vaccine to elicit an immune response, either humoral or cell mediated, which serves to protect the mammal from an infection. The protection provided need not be absolute, i.e., the infection need not be totally prevented or eradicated, if there is a statistically significant improvement compared with a control population of mammals. Protection may be limited to mitigating the severity or rapidity of onset of symptoms of the infection.

The term "recombinant" as used herein simply refers to the raccoon poxvirus constructs that are produced by standard genetic engineering methods.

The term "replicable" refers to a microorganism, in particular, a virus such as the raccoon poxvirus, that is capable of replicating, duplicating or reproducing in a suitable host cell.

The terms "vaccine" or "vaccine composition" are used interchangeably herein and refer to a pharmaceutical composition comprising at least one immunologically active component that induces an immune response in an animal, and/or protects the animal from disease or possible death due to an infection, and may or may not include one or more additional components that enhance the immunological activity of the active component. A vaccine may additionally comprise further components typical to pharmaceutical compositions.

A "vector" is a DNA molecule, capable of replication in a host organism, into which a gene is inserted to construct a recombinant DNA molecule.

General Description

In accord with the present invention, there is provided a unique recombinant rabies vaccine that uses the raccoon poxvirus (RCNV) strain in the manufacture of a stable, safe, highly efficacious and optionally adjuvant-free product. Specifically, the invention provides a recombinant raccoon poxvirus vector (rRCNV) comprising two or more exogenous nucleic acid molecules, each encoding at least one rabies virus glycoprotein, wherein at least two of the nucleic acid molecules are inserted into the hemagglutinin (ha) locus or the thymidine kinase (tk) locus, or at least one of the nucleic acid molecules is inserted into each of the hemagglutinin and thymidine kinase loci. The source of the exogenous nucleic acid molecules can be the same or different, although it is desirable to obtain the foreign gene from at least two different rabies strains. Advantageously, the new and highly preferred virus construct rRCNV-Rabies G2 of this invention uniquely expresses the rabies glycoproteins (G) of two different rabies virus strains in which it is highly desirable to insert the antigenic glycoproteins of the Challenge Virus Standard (CVS) and the Pasteur-Paris (PV) rabies strains at thymidine kinase (tk) and hemagglutinin (ha) loci, respectively, of the RCNV genome. In vitro expression of rabies glycoprotein in rRCNV-Rabies G2-infected Vero cells is confirmed by an indirect immunofluorescence assay (IFA) using a rabies glycoprotein specific monoclonal antibody. The rRCNV-Rabies G2 construct of the invention is very immunogenic and highly potent. The inoculation of cats and dogs in duration of immunity (DOI) studies, followed by virulent rabies virus challenge, demonstrates that the new recombinant rabies vaccine has excellent potency and usefulness in protecting mammals against rabies infection.

Raccoon poxvirus (Herman strain) was first isolated from the respiratory tract of raccoons with no clinical symptoms by Y. F. Herman in Aberdeen, Md. in 1961-1962 (Y. F. Herman, "Isolation and characterization of a naturally occurring pox virus of raccoons," In: Bacteriol. Proc., 64th Annual Meeting of the American Society for Microbiology, p. 117 (1964)). Several earlier studies reported that the RCNV vector expressing CVS rabies G gene at the tk locus is safe when administered to both wild animals and domestic animals including cats (see, for example, A. D. Alexander et al., "Survey of wild mammals in a Chesapeake Bay area for selected zoonoses," J. Wildlife Dis. 8: 119-126 (1972); C. Bahloul et al., "DNA-based immunization for exploring the enlargement of immunological cross reactivity against the lyssaviruses," Vaccine 16: 417-425 (1998); S. Chakrabarti et al., "Compact, Synthetic, vaccinia virus early/late promoter for protein expression," BioTechniques 23: 1094-1097 (1997); and J. C. DeMartini et al., "Raccoon poxvirus rabies virus glycoprotein recombinant vaccine in sheep," Arch. Virol. 133: 211-222 (1993)).

However, none of the earlier constructs provide the unique design of the present invention in which a rabies G gene is inserted into the ha site or in which at least two rabies G genes are inserted into both the tk and ha locus of the raccoon poxvirus genome. There are no constructs or animal studies showing the novel constructs of this invention.

The previous recombinant rabies construct known as vKB3-JE13 (RCNV Rab-G, sold commercially as RABORAL V-RG® from Merial, Harlow, Essex, UK) used the Herman strain of the RCNV vector but the construct only possesses a single insertion of the G gene of the rabies CVS strain at the tk locus of the RCNV genome. Although the rRCNV-Rabies G2 construct of the present invention also utilizes the Herman strain of the RCNV vector, this novel construct has foreign genes from two different rabies strains inserted into two loci, that is, the foreign gene material comprising the G genes of rabies CVS and PV strains is inserted into the RCNV genome and the insertion sites are specific to provide DNA from the CVS gene at the tk locus and DNA from the PV gene at the ha locus of the RCNV genome. In the new rRCNV-Rabies G2 construct of the present invention, the insertion of rabies G genes into the combination of both tk and ha loci of RCNV genome further attenuates the avirulent Herman strain but, at the same time, provides a potent broad spectrum vaccine.

Similar to the vKB3-JE13, the rRCNV-Rabies G2 of the present invention is prepared initially using the vv P 11 late promoter to insert the CVS gene at the tk locus but then further employs a synthetic early-late promoter to drive and insert the additional PV gene at the ha locus. Stability and usefulness of the rRCNV-Rabies G2 in being able to express foreign rabies antigens from the tk and ha loci are important properties of the new multivalent construct that were heretofore unknown.

The markedly improved rRCNV-Rabies G2 construct of the present invention also provides unforeseen and significant advantages over the prior construct vKB3-JE13 in terms of being a better construct. Surprisingly, the rRCNV-Rabies G2 has better vector safety for handling, substantially better minimal protective dose (i.e., markedly more potent) and wider protective range covering the Challenge Virus Standard (CVS) and the Pasteur-Paris (PV) rabies strains.

For example, the performance of rRCNV-Rabies G2 and vKB3-JE13 (RCNV Rab-G) in the standard National Institutes of Health (NIH) mouse potency test at comparable titers reveals the superior relative potency (RP) value of 6.8 for the rRCNV-Rabies G2 (6.3 $Logs_{10}TCID_{50}$/mL) as compared to a much lower RP value of 0.3 for the vKB3-JE13 (6.4 $Logs_{10}TCID_{50}$/mL). The rRCNV-Rabies G2 construct of the present invention was unexpectedly 23 times more potent than the vKB3-JE13 construct.

While the known recombinant RCNV carrying the rabies glycoprotein gene from CVS alone (vKB3-JE13) did demonstrate efficacy in cats vaccinated subcutaneously with one single dose, vKB3-JE13 required a high titer of 8.3 $Log_{10}TCID_{50}$/mL of RCNV Rab-G to achieve adequate protection against rabies in a one-year duration of immunity study (DOI) showing that 96.2% (25/26) of cats given the high concentration of Rab-G were protected while 93.8% (15/16) of the control died due to rabies challenge. Downstream processing studies, however, indicated that it was not feasible to produce such high titer virus for commercialization. Due to safety and vector concerns, the vKB3-JE13 falls short of practical use in cats.

Additionally, the efficacy data demonstrated that this prior vKB3-JE13 construct failed to meet the statutory requirements (Title 9, Code of Federal Regulations) in one-year DOI study for dogs. Only 79.2% (19/24) of dogs vaccinated subcutaneously with a single dose of 8.3 $Log_{10}TCID_{50}$/mL of RCNV Rab-G were protected against rabies in the one-year duration of immunity study (DOI) while 100% (13/13) of the control died due to rabies challenge.

On comparison, the one-year DOI for the new rRCNV-Rabies G2 construct of the present invention provided excellent results in cats at a much lower concentration than vKB3-JE13 needed. At a titer of 6.28 $Log_{10}TCID_{50}$/mL (per dose), challenge results demonstrated that while 9/10 (90%) controls died due to rabies, advantageously, 25/25 (100%) vaccinates remained well for a period of 90 days, which is a satisfactory test that meets the statutory requirements for rabies vaccine efficacy. The results from the one-year DOI study demonstrate that the recombinant rabies vaccine of the present invention is highly efficacious in the prevention of rabies for at least one year following a single vaccination in cats.

With respect to the one-year DOI study in dogs, the new rRCNV-Rabies G2 construct of this invention provided excellent and successful results in dogs whereas the RCNV Rab-G of the art failed to give adequate protection. At a titer of 6.28 $Log_{10}TCID_{50}$/mL (per dose), challenge results demonstrated that 9/10 (90%) controls died due to rabies while 22/25 (88%) vaccinates remained well for a period of 90 days, which satisfies the statutory requirements for rabies vaccine efficacy. The results from this one-year DOI study demonstrate that the recombinant rabies vaccine of the present invention is efficacious as an aid in the prevention of rabies for at least one year following a single vaccination in dogs.

In addition to the disadvantages of the prior recombinant vKB3-JE13 construct known in the art, other conventional inactivated rabies vaccines also have their technical problems in the veterinary field that the present invention solves. The inactivated rabies vaccines often need adjuvant supplements in order to obtain an effective immune response but, unfortunately, the adjuvant often contributes to the formation of sarcoma in cats and has other safety concerns in cats and dogs. The present invention uniquely solves the art-recognized problems and provides the recombinant raccoon poxvirus (rRCNV)-vectored rabies vaccine as a safer product that maintains an excellent immune response following a single vaccination in the absence of adjuvants.

Advantageously, the adjuvant-free rRCNV vectored rabies vaccine of the present invention also improves employee safety during vaccine production and completely eliminates any chance of rabies virus surviving inactivation and decontamination procedures used during commercial production. The rRCNV-Rabies G2 is further attenuated by the insertion of Pasteur-Paris rabies G gene into the ha locus of the RCNV vector containing the CVS G gene inserted at the tk locus of the RCNV genome. In other words, while the attenuated rabies virus is considered Biosafety Level 2 pathogen of moderate potential health hazard, the rRCNV-Rabies G2 is deemed to be quite safe as a low risk Biosafety Level 1 pathogen.

The novel rabies vaccine, live raccoon poxvirus vector (i.e., the rRCNV-Rabies G2 construct of the invention) is typically employed for the vaccination of healthy cats and dogs at three months of age or older as an aid in the prevention of rabies infection. Other domestic pets such as ferrets will also benefit from inoculation against rabies at an age of sufficient maturity for an adequate immune response. The vaccine may also be used in younger cats, dogs and additional mammals that are exposed to the rabies virus if the vaccine is needed as a post-infection treatment.

Virus shedding was not demonstrated following inoculation of cats with a high level of live RCNV, confirming that RCNV is non-replicative and non-pathogenic in cats. Cats were chosen as the test animal because cats are more susceptible to RCNV than dogs. The natural routes of infection for RCNV is mainly through oral mucous membranes, skin abrasions and the respiratory tract. The tonsil is the preferred location for these viruses to replicate. The oral route, the most common route of infection, was therefore chosen for administering the recombinant viruses in some studies for the examples illustrating the invention below. However, it is contemplated that the vaccine of the present invention may be administered by a variety of conventional routes.

The NIH (National Institute of Health) mouse potency testing demonstrates that the rRCNV-Rabies G2 construct is very immunogenic and highly potent. The dose titration studies indicate full protection against rabies challenge (three months following the vaccination) when cats and dogs are subcutaneously vaccinated with immunologically effective dosages of rRCNV-Rabies G2. Three-month duration of immunity (DOI) studies, one-year DOI studies in cats and dogs and the reversion to virulence study in cats of the Rabies Vaccine, Live Raccoon Poxvirus Vector of the present invention show excellent results. Quite advantageously, the oral administration of raccoon poxvirus vectored vaccines did not revert to virulence or disseminate into body fluids or feces, and no unfavorable reactions were observed after the concentrated stock of rRCNV-Rabies G2 X+3 was administrated subcutaneously in cats and dogs.

Cats and dogs were vaccinated with three different titers of rRCNV-rabies G2 vaccine, followed by virulent rabies virus challenge three months following a single vaccination, to demonstrate the short-term efficacy and determine the proper dosage for a longer duration of immunity study. In cats, 100% (10/10) of cats, subcutaneously vaccinated with a single dose of 6.5, 5.5 and 4.5 $Log_{10}TCID_{50}$/mL of rRCNV-Rabies G2, were beneficially protected while 80% (8/10) of the control died due to rabies challenge. In dogs, 100% (10/10), 90% (9/10), and 70% (7/10) of dogs, subcutaneously vaccinated with a single dose of 6.5, 5.5 and 4.5 $Log_{10}TCID_{50}$/mL of rRCNV-Rabies G2, were respectively protected while 100% (10/10) of the control died due to rabies challenge. The latter results in dogs illustrate standard titration studies used in the veterinary vaccine field to obtain the proper dosage of a new vaccine product, demonstrating that a titer of 4.5 $Log_{10}TCID_{50}$/mL would be an insufficient concentration to protect dogs from rabies but the vaccine shows efficacy in dogs at viable titers of 6.5 $Log_{10}TCID_{50}$/mL and 5.5 $Log_{10}TCID_{501}$ mL.

As described herein above and exemplified in the below examples, the results from the one-year duration of immunity (DOI) studies after a single administration of the recombinant rRCNV-Rabies G2 vaccine of this invention to cats and dogs also show excellent potency and usefulness of the vaccine. The recombinant rabies vaccine surprisingly and beneficially results in significantly long lasting immunity after the single inoculation.

Generally, the virus rRCNV-Rabies G2 may be constructed by the insertion of a rabies glycoprotein gene, for instance, the rabies Pasteur-Paris glycoprotein gene (G), into the hemagglutination (ha) locus of the vKB3-JE13 genome. The known virus vKB3-JE13 expresses the rabies glycoprotein of the Challenge Virus Standard (CVS) strain at the thymidine kinase (tk) locus of raccoon poxvirus, wild type. In one embodiment, the construction processes of rRCNV-Rabies G2 are provided through two major steps. First, the PCR-amplified 1,575 bp rabies Pasteur-Paris G gene (GPV-PV) is cloned into the pFD2003SEL vector of the present invention constructed to generate plasmid pFD2003SEL-GPV-PV. This step includes subcloning KpnI-SalI rabies GPV-PV fragment from the FDAH's rabies DNA vaccine construct pVAX1-GPV-PV (as prepared in WO 00/63242) into the plasmid pFD2003SEL thereby generating pFD2003SEL-GPV-PV. Second, three-way co-infection/transfection of vKB3-JE13 and plasmid pFD2003SEL-GPV-PV in COS-7 cells is conducted to generate the rRCNV-Rabies G2 by allelic exchange at ha locus. The blue plaques (Lac$^+$) are cloned by four successive rounds of plaque purification in Vero cells. The clone candidates are further expanded three more times in Vero cells using Minimum Essential Medium (MEM) supplemented with 0.05% lactalbumin hydrolysate (LAH), 30 µg/mL gentamicin sulfate, and 5% fetal bovine serum, and confirmed by gene-specific PCR and indirect immunofluorescence assay (IFA). The seventh passage is used to prepare a pre-master seed. The Master Seed may be established by a 1:10,000 dilution of pre-master seed, and designated rRCNV-Rabies G2, in which the raccoon poxvirus as a live vector expresses the rabies glycoproteins of Pasteur-Paris and CVS strains at ha and tk loci, respectively. This Master Seed is useful in the further manufacture of a Rabies Vaccine, Live Raccoon Poxvirus vector. The rRCNV-Rabies G2 construct is highly potent, safe and very efficacious as a vaccine for animals in the prophylaxis against rabies.

It is contemplated that the novel method described in the present invention may be applied by the person having ordinary skill in the art to antigenic glycoproteins obtained from other rabies strains in which the rabies glycoprotein of strains other than the illustrated CVS and PV strains are used and inserted at the tk and/or ha loci or, in the case of both the tk and ha loci, another glycoprotein gene may be inserted into an additional, third non-essential regions of the raccoon poxvirus vector such as, for example, at the serine protease inhibitor gene and the like to provide an immunogenic vaccine for the protection against rabies infection. For instance, the nucleotide or nucleic acid molecule encoding the antigenic glycoprotein from other rabies strains such as the canine rabies street virus, Arctic Fox virus, raccoon rabies virus or bat rabies virus strains may readily substitute for, or be used in addition to, the CVS and/or the PV strains. Alternatively, the glycoprotein gene of a new field isolate or rabies mutant may be isolated and utilized in the recombinant vaccine of the invention instead of the CVS and/or PV gene. It is also contemplated that the gene encoding an additional antigenic glycoprotein of a third rabies strain may be inserted into a third non-essential site of the raccoon poxvirus genome. Other non-essential genes beyond the tk and ha loci, for example, include those regions that are not essential for growth and propagation of the poxvirus.

While the examples illustrate the glycoprotein gene of the CVS strain being inserted in the tk locus and the glycoprotein gene of the PV strain being inserted in the ha locus, it is further contemplated that the genes be inserted vice versa where the G gene of CVS is at the ha locus and the G gene of PV is at the tk locus, or the same glycoprotein gene of the same rabies virus strain is inserted into both the tk and the ha sites to construct a strongly effective recombinant vaccine for heightened immune response to the pathogenic rabies virus. It may also appear desirable to construct a recombinant vaccine in which the nucleic acid encoding the rabies virus glycoprotein is only inserted at the ha site of the raccoon poxvirus genome.

Any method known to those skilled in the art may be used to prepare the genetic constructs of the present invention. For example, advantage may be taken of particular restriction sites for insertion of any of the desired nucleic acid sequences into the raccoon poxvirus vector using standard methodologies. Alternatively, one may utilize homologous recombination techniques when the insertion of large sequences is desired, or when it is desirable to insert multiple genes, as described herein. In this method, the plasmid sequences flanking the insertion site into which are to be inserted multiple genes, contain sequences which have sufficient homology with sequences present in the raccoon poxvirus genome to mediate recombination. The flanking sequences must be homologous to a region of the raccoon poxvirus that is non-essential for the growth and propagation of the raccoon poxvirus, such as the hemagglutinin locus, or the thymidine kinase locus, or the serine protease inhibitor locus. Although one promoter may be used to drive the expression of two exogenous genes to be recombined, the use of two promoters in an insertion vector, each promoter operably linked to an individual gene will also provide efficient expression.

This invention also provides a new method of protecting mammals against rabies or treating animals post-infection with the rabies virus by administering the potent new recombinant vaccines to the mammals in need of protection.

In the method of the invention, an immunologically effective amount of the vaccines of the present invention is administered to a mammal, particularly cats and dogs, in need of protection against or treatment of rabies infection in order to induce a protective immune response to rabies. Also contemplated is the use of the vaccine for immunizing cattle and horses against rabies. An effective immunizing amount given to the mammal is one in which a sufficient immunological response to the vaccine is attained to protect the mammal from the fatal neurological effect of the rabies virus. A protective immune response to rabies is considered to be obtained when the vaccine meets or exceeds the statutory guidelines for USDA approved rabies vaccines. The immunologically effective dosage or the effective immunizing amount that inoculates the animal and elicits satisfactory vaccination effects can be easily determined or readily titrated by routine testing such as, for example, by standard dose titration studies.

The vaccine can be administered in a single dose or in repeated doses, particularly as a post-infection treatment. Desirably, the vaccine is administered to healthy animals in a single inoculation to provide long term protection against rabies, protecting the animals from rabies for at least one year to three years or longer. Dosages may range, for example, from approximately 5.4 to approximately 6.7 $Log_{10}TCID_{50}$/mL (minimal protective dose) when administered to cats and dogs although some smaller cats can benefit from dosages about 4.5 $Logs_{10}TCID_{50}$/mL and higher. Ferrets can receive a similar dosage as used in cats and dogs.

Since there is a problem of rabies in horses and cattle in some countries, a suitable vaccination dose will be given to the large animals expressed as a titer per dose (1-2 mL) but not usually by body weight. The titer can be determined through routine titration studies known to those having ordinary skill in the veterinary art. It is contemplated that the rRCNV-Rabies G2 of the present invention can also find use in wildlife animals such as foxes, skunks, mongooses, raccoons, bats and the like as a means of controlling the spread of rabies.

The vaccine may contain an immunologically effective amount of any one of the recombinant raccoon poxvirus vector constructs described herein. In another embodiment, the vaccine may contain an immunologically effective amount of any two or more of the recombinant raccoon poxvirus vector constructs described herein. In one embodiment, the multivalent vaccine only contains one vector construct.

The vaccine can be readily given by any route of administration, orally, intranasally, transdermally (i.e., applied on or at the skin surface for systemic absorption), parenterally, etc., though some routes may be logistically more difficult depending on the animal and the handler. The parenteral route of administration includes, but is not limited to, subcutaneous, intramuscular, intravenous, intraperitoneal, intradermal (i.e., injected or otherwise placed under the skin) routes and the like. Preferably, the vaccine is administered subcutaneously to healthy cats, dogs and other domestic pets.

The poxvirus vector may be live or inactivated by conventional procedures for preparing inactivated viral vaccines, for example, using BEI (binary ethyleneimine), formalin and the like, with BEI being a preferred inactivant, though it is highly desirable for the vaccine of the present invention to use a live raccoon poxvirus for optimal and potent immunological efficacy. The live raccoon poxvirus is also replicable, meaning it can reproduce in suitable culture to make copies of itself for vaccine development from the master seed virus. Beneficially, the live recombinant RCNV expressing rabies glycoproteins (G2) of rabies Challenge Virus Standard (CVS) and Pasteur-Paris strains is useful as a vaccine, either alone or in combination with suitable carriers, diluents and adjuvants. A suitable carrier is non-toxic and pharmaceutically acceptable to administer to all mammals. It is contemplated that the product used for inoculation of cats, however, be adjuvant-free. The vaccine product can be in the form of a liquid or a lyophilized powder to be reconstituted with standard, non-toxic diluents shortly before use. The lyophilized powder has the advantage that it maintains its potency under long term storage with no titer loss when lyophilized and stored at 2-7° C.

When administered as a liquid, the present vaccine may be prepared in the conventional form of an aqueous solution, syrup, elixir, tincture and the like. Such formulations are known in the art and are typically prepared by dissolution or dispersion of the antigen and other additives in the appropriate carrier or solvent systems for administration. Suitable nontoxic, physiologically acceptable carriers or solvents include, but are not limited to, water, saline, ethylene glycol, glycerol, etc. The vaccine may also be lyophilized or otherwise freeze-dried and then aseptically reconstituted or rehydrated using a suitable diluent shortly before use. Suitable diluents include, but are not limited to, saline, Eagle's minimum essential media and the like. Typical additives or co-formulants are, for example, certified dyes, flavors, sweeteners and one or more antimicrobial preservatives such as thimerosal (sodium ethylmercurithiosalicylate), neomycin, polymyxin B, amphotericin B and the like. Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of feline body fluids. Isotonicity can be appropriated adjusted with sodium chloride and other salts as necessary. At the time of vaccination, the virus is thawed (if frozen) or reconstituted (if lyophilized) with a physiologically-acceptable carrier such as deionized water, saline, phosphate buffered saline, or the like. Suitable solvents, such as propylene glycol, can be used to increase the solubility of the ingredients in the formulation and the stability of liquid preparations.

For inoculation of dogs and other animals that do not have untoward effect from immune-enhancing adjuvant systems, the vaccine product may optionally contain a variety of typical, non-toxic, pharmaceutically acceptable additives, diluents and adjuvants that include, but are not limited to, preservatives; stabilizers; emulsifiers; aluminum hydroxide; aluminum phosphate; pH adjusters such as sodium hydroxide, hydrochloric acid, etc.; surfactants such as Tween® 80 (polysorbate 80, commercially available from Sigma Chemical Co., St. Louis, Mo.); liposomes; iscom adjuvant; synthetic glycopeptides such as muramyl dipeptides; extenders such as dextran or dextran combinations, for example, with aluminum phosphate, dextran sulfate, DEAE-Dextran and the like; carboxypolymethylene, such as CARBOPOL® (polyacrylic polymer commercially available from B.F. Goodrich Company, Cleveland, Ohio); ethylene maleic anhydride or ethylenelmaleic anhydride copolymers (EMA®, a linear ethylene/maleic anhydride copolymer having approximately equal amounts of ethylene and maleic anhydride, having an estimated average molecular weight of about 75,000 to 100,000, commercially available from Monsanto Co., St. Louis, Mo.); acrylic copolymer emulsions such as a copolymer of styrene with a mixture of acrylic acid and methacrylic acid like NEOCRYL® A640 (e.g. U.S. Pat. No. 5,047,238, an uncoalesced aqueous acrylic acid copolymer of acrylic acid and methacrylic acid mixed with styrene, commercially available from Polyvinyl Chemicals, Inc., Wilmington, Mass.); bacterial cell walls such as mycobacterial cell wall extract; *Corynebacterium*-derived adjuvants such as *Corynebacterium parvum*; *Propionibacterium*-derived adjuvants such as *Propionibacterium* acne; *Mycobacterium bovis* (Bacille Calmette-Guerin, or BCG); subviral particle adjuvants such as orbivirus; cholera toxin; N,N-dioctadecyl-N',N'-bis(2-hydroxyethyl)-propanediamine (pyridine); monophosphoryl lipid A; dimethyldioctadecylammonium bromide (DDA, commercially available from Kodak, Rochester, N.Y.); synthetics and mixtures thereof. Further additives that may be employed in the present vaccine include, but are not limited to, dextrose, conventional antioxidants and conventional chelating agents, such as ethylenediamine tetraacetic acid (EDTA). Other pharmaceutically acceptable adjuvants that may optionally supplement the vaccine formulation include, but are not limited to, polyanions, polycations, peptides, mineral oil emulsion, immunomodulators, a variety of combinations and the like. Further non-limiting examples of suitable adjuvants include squalane and squalene (or other oils of animal origin); polyoxyethylene-polyoxypropylene block copolymers such as PLURONIC® (L121, for example, commercially available from BASF Aktiengesellschaft, Ludwigshafen, Germany); saponin; Quil A (commercial name of a purified form of *Quillaja saponaria*, available from Iscotec AB, Sweden and Superfos Biosector a/s, Vedbaek, Denmark); mineral oils such as MARCOL® (a purified mixture of liquid saturated hydrocarbons, commercially available from Exxon-Mobil, Fairfax, Va.); vegetable oils such as peanut oil; interleukins such as interleukin-2 and interleukin-12; interferons such as gamma interferon; animal poxvirus proteins or mixtures thereof. Examples of suitable stabilizers include, but are not limited to, sucrose, gelatin, peptone, digested protein extracts such as NZ-Amine or NZ-Amine AS. Examples of emulsifiers include, but are not limited to, mineral oil, vegetable oil, peanut oil and other standard, metabolizable, nontoxic oils useful for injectables or intranasal vaccines. Desirably, aluminum hydroxide is admixed with other adjuvants such as saponin or Quil A to form combinations such as saponin-aluminum hydroxide or Quil A-aluminum hydroxide. A preferred adjuvant comprises ethylene/maleic anhydride copolymer, copolymer of styrene with a mixture of acrylic acid and methacrylic acid, mineral oil emulsion or combinations thereof.

The particularly preferred adjuvant system that significantly enhances the potency of the rRCNV-Rabies G2 construct of the present invention for canine use comprises the combination of an ethylene/maleic copolymer such as EMA-31® (a linear ethylene/maleic anhydride copolymer having approximately equal amounts of ethylene and maleic anhydride, having an estimated average molecular weight of about 75,000 to 100,000, commercially available from Monsanto Co., St. Louis, Mo.) and an acrylic acid copolymer emulsion such as NEOCRYL® (an uncoalesced aqueous acrylic acid copolymer of acrylic acid and methacrylic acid mixed with styrene (acrylic-styrene emulsion), commercially available from Polyvinyl Chemicals, Inc., Wilmington, Mass.). Studies substantiated that the rRCNV-Rabies G2 construct at a titer of 6.4 $Log_{10}TCID_{50}$/mL (per dose) is highly efficacious in the presence of the combination adjuvant system comprising EMA-31® and NEOCRYL®. Challenge results indicated that 10/10 (100%) control dogs died or showed rabies signs, indicating that the study was a valid challenge test. By contrast, 9/10 (90%), 10/10 (100%), and 10/10 (100%) vaccinates in three inoculated groups remained well over the duration of the study.

In the case of dogs, the recombinant rabies vaccine of the present invention may also optionally contain a mixture with one or more additional canine antigens such as, for example, *Ehrlichia canis*, canine parvovirus (CPV), canine distemper, canine parainfluenza virus (CPI), canine adenovirus type II (CAV-2), canine adenovirus (CDV), canine coronavirus (CCV), *Leptospira icterohemorrhagiae* (LI), *Leptospira canicola* (LC), *Leptospira grippotyphosa* (LG), *Leptospira pomona* (LP) and the like. A particularly preferred combination of antigens encompasses isolates of canine parvovirus, canine distemper, canine adenovirus and canine parainfluenza, with or without coronavirus and *Leptospira* (including the emerging serovars, *L. grippotyphosa* and *L. pomona*).

In the case of cats, the recombinant rabies vaccine of the present invention may also optionally contain a mixture with one or more additional feline antigens such as, for example, feline calicivirus (FCV), *Chlamydophila felis* (*C. felis*, also previously and commonly known as *Chlamydia psittaci* (FCP)), feline leukemia virus (FeLV), feline panleukopenia virus (FPV), feline rhinotracheitis virus (FVR), feline immunodeficiency virus (FIV), feline infectious peritonitis virus (FIPV), *Bartonella* bacteria (e.g. typical cat scratch disease) and the like.

As terms are used herein, the conventional meanings known to those having ordinary skill in the art prevails. For instance, the term "nucleic acid molecule" or "nucleic acid sequence" has its plain meaning to refer to long chains of repeating nucleotides such as the repeated units of purine and pyrimidine bases that direct the course of protein synthesis, that is, they encode and express the protein substance. As the term is used in the claims, the nucleic acid refers to the known exogenous or foreign genes that encode the rabies virus glycoprotein. The term "recombinant" as used herein simply refers to the raccoon poxvirus constructs that are produced by standard genetic engineering methods.

EXAMPLES

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the present invention may be obtained from the examples that follow below. These working examples are intended to illustrate the invention without limiting its scope.

Example 1

Construction of rRCNV-Rabies G2

Briefly, the virus rRCNV-Rabies G2 was constructed by insertion of the rabies Pasteur-Paris glycoprotein gene (G) into the hemagglutination (ha) locus of the vKB3-JE13 genome. The complete construct comprises the rabies glycoprotein genes of CVS and Pasteur-Paris strains inserted into the RCNV thymidine kinase (tk) and hemagglutination (ha) loci, respectively, further attenuating the wild type raccoon poxvirus, an avirulent Herman strain.

The virus vKB3-JE13, which was obtained from Dr. Joseph J. Esposito (Centers for Disease Control and Prevention (CDC), Atlanta, Ga.), expresses the rabies glycoprotein of the Challenge Virus Standard (CVS) strain at the thymidine kinase (tk) locus of raccoon poxvirus (see also U.S. Pat. Nos. 7,087,234; 6,241,989; 5,348,741 and 5,266,313 for additional information). The Pasteur-Paris G gene was obtained from the rabies DNA vaccine that can be produced according to the methods of WO 00/63242. The construction processes of rRCNV-Rabies G2 were provided through two major steps. First, the PCR-amplified 1,575 bp rabies Pasteur-Paris G gene (GPV-PV) from the FDAH's rabies DNA vaccine construct pVAX1-GPV-PV was cloned into a plasmid pFD2003SEL vector to generate plasmid pFD2003SEL-GPV-PV. Second, three-way co-infection/transfection of vKB3-JE13 and plasmid pFD2003SEL-GPV-PV in COS-7 cells was conducted to generate rRCNV-Rabies G2 by allelic exchange at the ha locus. The blue plaques (Lac$^+$) were cloned by four successive rounds of plaque purification in Vero cells. The clone candidates were further expanded three more times in Vero cells using Minimum Essential Medium (MEM) supplemented with 0.05% lactalbumin hydrolysate (LAH), 30 µg/mL gentamicin sulfate and 5% fetal bovine serum, and thereafter confirmed by gene-specific PCR and indirect immuno-fluorescence assay (IFA). The seventh passage was used to prepare a pre-master seed. The Master Seed was established by a 1:10,000 dilution of pre-master seed, and designated rRCNV-Rabies G2, in which the raccoon poxvirus as a live vector is capable of uniquely expressing the rabies glycoproteins of the Pasteur-Paris and CVS strains at the ha and tk loci, respectively. The master seed virus of the rabies vaccine, live raccoon poxvirus vector (rRCNV-Rabies G2) was identified by RCNV ha, tk and rabies G genes-specific PCR testing. The expression of rabies glycoprotein was confirmed by IFA using rabies G protein specific monoclonal antibody from Accurate Chemical & Scientific Corporation, Westbury, N.Y. Purity testing for detection of bacterial, fungal and mycoplasma contamination plus safety testing in cats and dogs were conducted in accordance with APHIS standard protocols. Satisfactory results of all purity and safety testing were reported.

In more detail, the following protocol was followed to prepare the recombinant organism rRCNV-Rabies G2:

Regarding the recipient characterization, as noted and described above, the parental organism was the Herman strain of raccoon poxvirus (RCNV) that was first isolated from the respiratory tract of raccoons with no clinical symptoms by Y. F. Herman in Aberdeen, Md. in 1961-1962. The RCNV is a member of the Poxyiridae Family containing a linear and nearly 200 kb double-stranded DNA genome with a hairpin loop at each end. Like other poxviruses (vaccinia virus, fowlpox virus and canarypox virus), RCNV replicates in the cytoplasm, uses its own transcription systems, and has been used as a live vector to express the foreign genes for vaccine development. However, the previous, known use of RCNV has been limited to the insert of the glycoprotein G of only one rabies virus strain at only the tk locus of the raccoon poxvirus genome.

For genetic markers, the RCNV wild type contains the tk gene, designated TK$^+$ phenotype. The insertion of rabies CVS G gene in the prior virus vKB3-JE13 construct disrupts the open reading frame of tk gene and renders the RCNV TK$^-$. Similarly, the RCNV wild type contains the ha gene, designated HA+ phenotype. The insertion of rabies Pasteur-Paris G gene by the method of the present invention disrupted the open reading frame of ha gene and rendered the RCNV HA−.

With respect to the donor characterization, the donor organisms are described as follows: Rabies virus, a negative-stranded RNA virus, is a member of the genus Lyssavirus within the family Rhabdoviridae. Rabies virus can infect all warm-blooded animals. Infection with this virus can result in fatal neurological disease. Five structural proteins: the nucleoprotein (N), phosphoprotein (M1), matrix protein (M2), transmembrane glycoprotein (G) and RNA-dependent RNA polymerase (L), are encoded by the 12-kb viral genome. It is known that the viral antigen G protein can induce virus neutralizing antibody and protection against lethal rabies virus challenge.

To obtain the donor genes, the rabies G-cDNAs were amplified from rabies CVS and Pasteur-Paris strains using reverse transcriptase (RT)-PCR. The size of CVS and Pasteur-Paris rabies G genes is 1575-bp. The complete nucleotide sequence and restriction enzyme map of plasmid pFD2003-GPV-PV are shown in FIGS. 1A through 1M and FIGS. 2A and 2B. Further DNA sequence analysis indicated that rabies CVS G gene shares 89% identity with rabies Pasteur-Paris G gene, and these two rabies G genes were inserted at the tk and ha loci, respectively, of rRCNV-Rabies G2 genome in the opposite orientation.

Figure 3B:
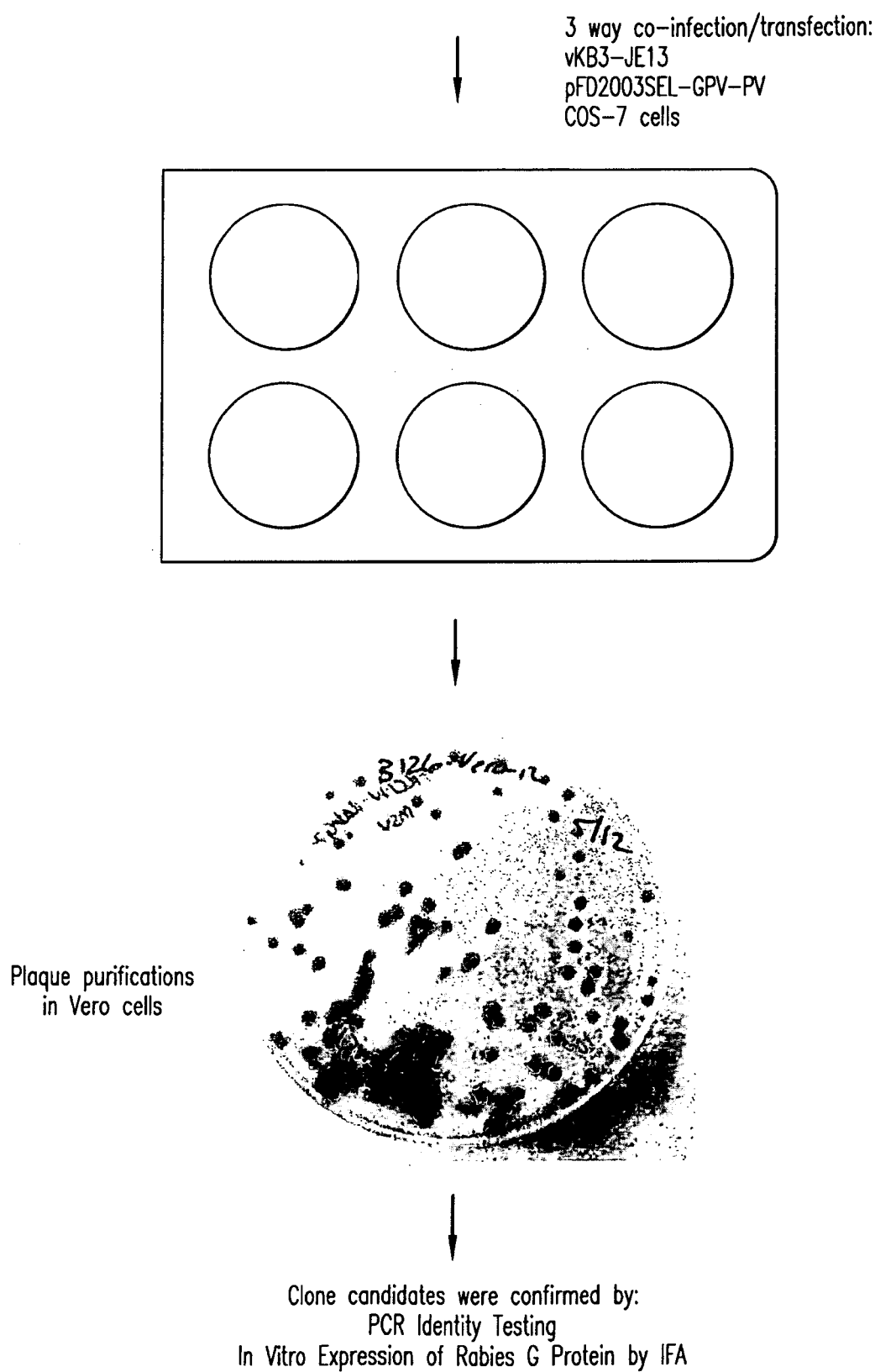
FIGS. 3A and B shows the diagram of the key steps in the construction of rRCNV-Rabies G2. KpnI-SalI rabies GPV-PV fragment was subcloned from the rabies DNA vaccine pVAX1-GPV-PV (as prepared in WO 00/63242) into the plasmid pFD2003SEL to generate the plasmid pFD2003SEL-GPV-PV. Three-way co-infection/transfection using vKB3-JE13, pFD2003SEL-GPV-PV and COS-7 cells generates the pool clones of rRCNV-Rabies G2. Next step involves plaque purification in Vero cells and pure clone selection. Clone candidates are confirmed by PCR identity testing and in vitro expression of rabies G protein by IFA from which rRCNV-Rabies G2 is obtained.
Figure 4:
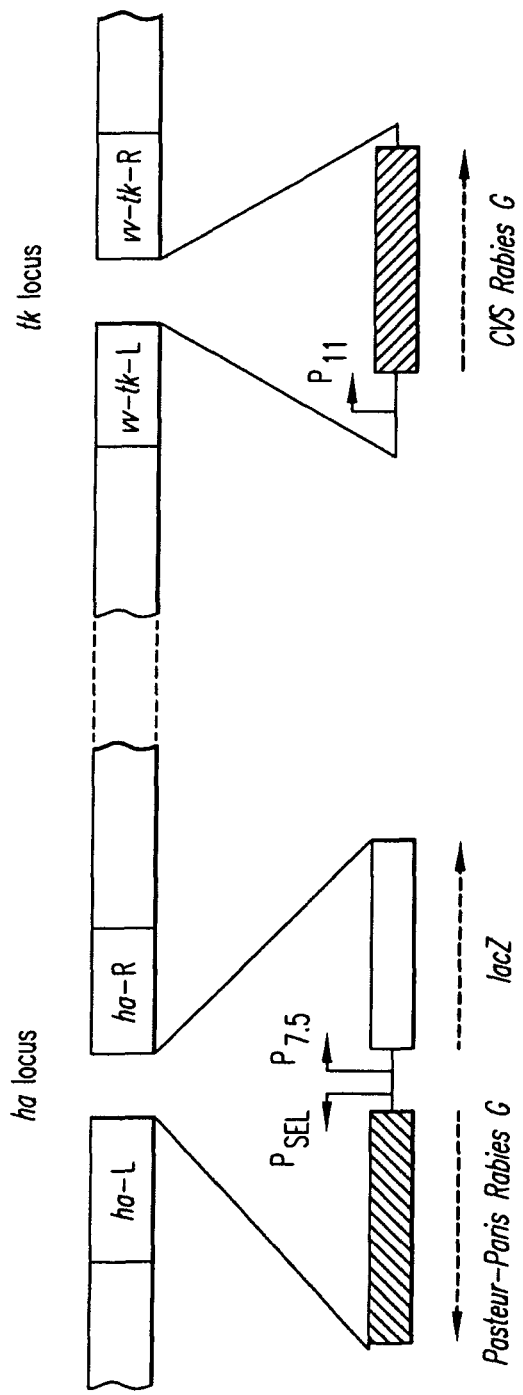
FIG. 4 illustrates the diagram of rRCNV-Rabies G2 genome (about 200 kb linear dsDNA) in which the Pasteur-Paris rabies G2 lacZ is constructed at the ha locus and the CVS rabies G is constructed at the tk locus of the recombinant raccoon poxvirus genotype.

To construct the recombinant organism, the virus rRCNV-Rabies G2 was constructed by insertion of the rabies Pasteur-Paris glycoprotein gene (G) into hemagglutination (ha) locus of vKB3-JE13 genome. The construction process of rRCNV-Rabies G2 involved two major steps. First, the KpnI-SalI fragment containing 1,575 bp rabies Pasteur-Paris G cDNA (GPV-PV) amplified by PCR using the plasmid pVAX1-GPV-PV that was constructed from the plasmid pGPV-PV (see the rabies DNA vaccine and pGPV-PV prepared in WO 00/63242) as a template was inserted into the pFD2003SEL vector to generate plasmid pFD2003SEL-GPV-PV. In this construct, the expression of GPV-PV was regulated by the synthetic early-late promoter (PSEL), and the expression of E. coli β-galactosidase as a reporter gene was under the transcriptional control of the vaccinia virus 7.5 kDa promoter ($P_{7.5}$) in the opposite orientation. The entire expression cassette was flanked by RCNV ha sequence. Second, three-way infection/transfection of vKB3-JE13 and plasmid pFD2003SEL-GPV-PV in COS-7 cells was conducted to generate the rRCNV-Rabies G2 by allelic exchange at ha locus. The blue plaques (Lac+) were cloned by five successive rounds of plaque purification in Vero cells. The gene (ha or tk)-specific PCR was used to confirm no presence of mixed population, and indirect immunofluorescence assay (IFA) to determine the expression of rabies glycoprotein. See FIG. 3 for an illustration of the key steps in the construction of rRCNV-Rabies G2, and FIG. 4 for the diagram of rRCNV-Rabies G2 genome.

As an intermediate cloning vector, the plasmid pFD2003SEL-GPV-PV was constructed as described herein. The complete sequence and restriction enzyme map of the plasmid pFD2003SEL-GPV-PV are shown in FIGS. 1A through 1M and FIGS. 2A and 2B, respectively.

To introduce the genetic modifications to the recipient, the G genes of rabies CVS and Pasteur-Paris were inserted into the tk and ha loci, respectively, of the RCNV genome by homologous recombination. The previously described procedure with vaccinia virus (see J. J. Esposito et al., "Vaccinia virus recombinants expressing rabiesvirus glycoprotein protect against rabies," Virus Genes 1: 7-21 (1987)) was used to accomplish this process of introducing the new genetic modification of the present invention to the raccoon poxvirus.

Screening methods and protocols for the identification and purification of the recombinant organism were performed as follows: The recombinant viruses were purified by a standard viral plaque purification technique. The vKB3-JE13 was generated by homologous recombination within CV-1 cells. The TK− viruses were selected in the presence of the mutagenic compound 5-bromodeoxyuridine (BUdR), and the recombinants were further screened by a variety of methods, including DNA hybridization, PCR, and immunological screening of rabies glycoprotein protein expression. The rRCNV-Rabies G2 was screened by blue plaque (Lac+) purification, gene (ha or tk)-specific PCR and IFA.

Example 2

PCR Identity Testing of rRCNV-Rabies G2 MSV and X+5

To identify the ha and tk genes in RCNV wild type and the rabies glycoprotein (G) gene inserted at both the ha and tk loci of the rRCNV-Rabies-G2 genome and to demonstrate that there is no mixed population present in rRCNV-Rabies G2 MSV and X+5, comprehensive PCR testing was performed using the following materials and methods.

Materials
1. Viruses:
   a) rRCNV-Rabies G2 MSV
   b) rRCNV-Rabies G2 X+5
   c) RCNV wild type Esposito
2. QIAGEN DNeasy Tissue Kit (commercially available from Qiagen Inc, Valencia, Calif., USA)
3. Gene-specific primers:
   a) Primers HA-08 and HA-Pst were used to amplify a 563-bp ha gene fragment of RCNV wild type for identity testing.
      i) HA-08: 5'-GAA ACA ATG CCA AAT ATC TCT-3' (which corresponds to SEQ ID NO:2)
      ii) HA-Pst: 5'-TCA TTG ACA TCT GGA GAT GCA GGT ACT-3' (which corresponds to SEQ ID NO:3)
   b) Primers HA-Pst and gp-1F were used to amplify a 1303-bp G gene fragment of rabies Pasteur-Paris at ha locus of rRCNV-Rabies G2 genome for identity testing.
      i) HA-Pst: see above-noted sequence
      ii) gp-1F: 5'-ACA CTA ACT TCG TTG GTT-5' (which corresponds to SEQ ID NO:4)
   c) Primers TK-LW and TK-RW were used to amplify a 503-bp tk gene fragment of RCNV wild type for identity testing.
      i) TK-LW: 5'-AAC GTA ATG GAT ATA TTA AAG TCT-3' (which corresponds to SEQ ID NO:5)
      ii) TK-RW: 5'-GAA AAC GAC GCC TCT TTA AAG-3' (which corresponds to SEQ ID NO:6)
   d) Primers TK-RR and gJE-F1 were used to amplify a 1637-bp G gene fragment of rabies CVS at tk locus of rRCNV-Rabies G2 genome for identity testing.
      i) TK-RR: 5'-GAA AAG GAA GCC TCC TTA AAG-3' (which corresponds to SEQ ID NO:7)
      ii) gJE-F1: 5'-TCT CCT ACA TGG AAC TCA-3' (which corresponds to SEQ ID NO:8)
4. Applied Biosystems AmpliTaq Gold DNA Polymerases (commercially available from Applied Biosystems, Foster City, Calif.)
5. Amersham-Pharmacia-Biotech Inc. dNTPs (commercially available from Amersham Biosciences, Piscataway, N.J.)
6. Applied Biosystems GeneAmp PCR System 9700 (commercially available from Applied Biosystems, Foster City, Calif.)

Methods

A. DNA Preparation

The rRCNV genomic DNA preparation was performed using a QIAGEN DNeasy Tissue kit (commercially available from Qiagen Inc, Valencia, Calif., USA) as described in the instruction manual provided by Qiagen.

B. PCR Testing

In this comprehensive PCR testing, the primers HA-08 and HA-Pst were used to screen for RCNV wild type; the primers HA-Pst and gp-1F were used to screen for rRCNV-Rabies G2 at the ha locus; the primers TK-LW and TK-RW were used to screen for the RCNV wild type; and the primers TK-RR and gJE-F1 were used to screen for rRCNV-Rabies G2 at the tk locus.

1. For each PCR reaction, prepare the following reaction mixture:

| | |
|---|---|
| 5 μL | 10 × PCR Buffer |
| 3 μL | 25 mM MgCl$_2$ |
| 5 μL | 2 mM dNTPs |
| 5 μL | each of primers (10 μM) |
| 5 μL | DNA template |
| 0.5 μL | 5 units/μL ABI AmpliTaq Gold |
| 21.5 μL | ddH$_2$0 |

2. Incubate samples in thermal cycler at 95° C. for 10 min to completely denature the DNA template.
3. Amplify the target template for 35 cycles:

| Step | Temp | Time |
|---|---|---|
| Denaturation | 94° C. | 1.0 min |
| Annealing | 59° C. | 1.0 min |
| Extension | 72° C. | 2.0 min |

4. Hold samples at 72° C. for an additional 5 min.
5. Hold samples at 4° C. indefinitely.

C. Agarose Gel Electrophoresis

1. Combine 10 μL of each PCR product with 2 μL of loading buffer.
2. Run samples on 1% agarose gel with Promega Lambda DNA/Hind III and Promega 1 kb DNA ladder as markers (both products are commercially available from Promega Corporation, Madison, Wis.).

Results

Figure 5B:
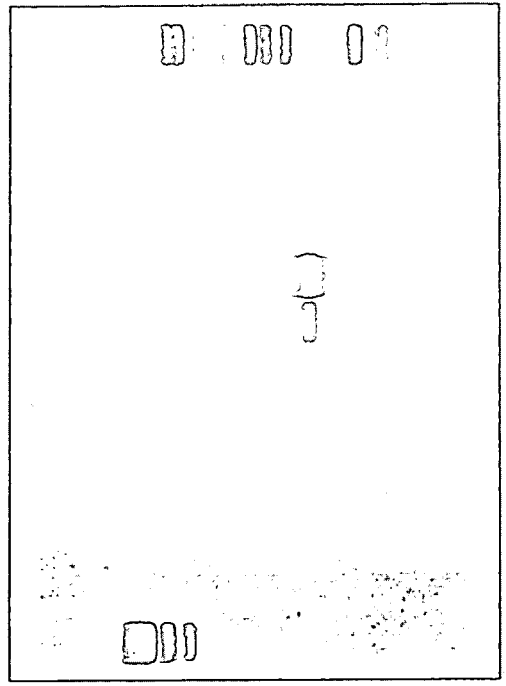
Figure 5A:
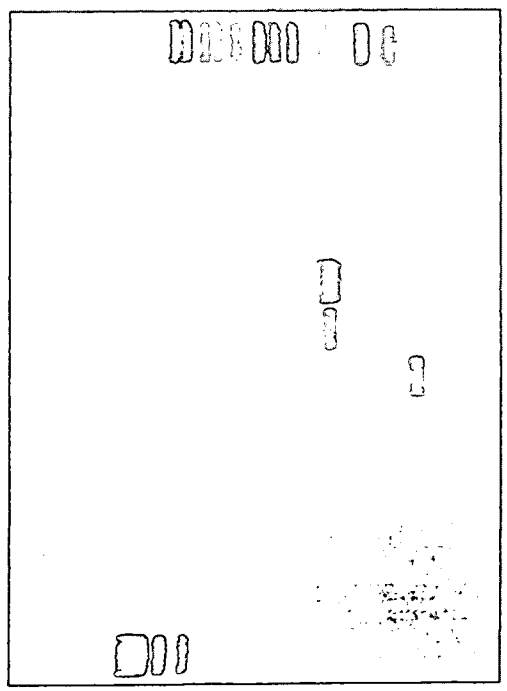

The results of PCR identity testing for rRCNV-Rabies G2 MSV and X+5 using gene-specific primers are shown in FIG. 5. When primers HA-08 and HA-Pst were used to detect RCNV ha gene (FIG. 5A, Gel A), and primers TK-LW and TK-RW were used to detect RCNV tk gene (FIG. 5B, Gel B), no band was observed in MSV and X+5 (Lanes 2-6). By contrast, both a 563-bp band for ha locus and a 503-bp band for tk locus were observed in RCNV wild type Esposito (Lane 7). These results indicated that no RCNV wild type was mixed in rRCNV-Rabies G2. When primers HA-Pst and gp-1F were used to examine if the rabies Pasteur-Paris G gene was inserted in the ha locus of rRCNV-Rabies G2 genome, and primers TK-RR and gJE-F1 were used to examine if the rabies CVS G gene was inserted in the tk locus of rRCNV-Rabies G2 genome, both a 1303-bp band for ha locus and 1637-bp band for tk locus were observed in MSV and X+5 (Lanes 8-9), respectively. By contrast, no band was observed in the RCNV wild type Esposito (Lane 13). The results indicated that the rabies Pasteur-Paris and CVS G genes were inserted into ha and tk loci, respectively, of rRCNV-Rabies G2 genome. These results are summarized in the below Table 1:

TABLE 1

Results of PCR Identity Testing

| LANE | SAMPLES (DNA TEMPLATE) | PRIMERS (GEL A) | PRIMERS (GEL B) | TARGET GENE | RESULTS |
|---|---|---|---|---|---|
| 1 | Lambda/Hind III Marker | NA | NA | NA | NA |
| 2 | rRCNV-Rabies G2, MSV | HA-08, HA-Pst | TK-LW, TK-RW | wt ha/tk | −* |
| 3 | rRCNV-Rabies G2, x + 5 | HA-08, HA-Pst | TK-LW, TK-RW | wt ha/tk | − |
| 4 | DNA Purification Negative Control-01 | HA-08, HA-Pst | TK-LW, TK-RW | wt ha/tk | − |
| 5 | DNA Purification Negative Control-02 | HA-08, HA-Pst | TK-LW, TK-RW | wt ha/tk | − |
| 6 | PCR Negative Control (water) | HA-08, HA-Pst | TK-LW, TK-RW | wt ha/tk | − |
| 7 | PCR Positive Control (RCNV Esposito-3) | HA-08, HA-Pst | TK-LW, TK-RW | wt ha/tk | +** |
| 8 | rRCNV-Rabies G2, MSV | HA-Pst, gp-1F | TK-RR, gJE-F1 | Rabies G | + |
| 9 | rRCNV-Rabies G2, x + 5 | HA-Pst, gp-1F | TK-RR, gJE-F1 | Rabies G | + |
| 10 | DNA Purification Negative Control-01 | HA-Pst, gp-1F | TK-RR, gJE-F1 | Rabies G | − |
| 11 | DNA Purification Negative Control-02 | HA-Pst, gp-1F | TK-RR, gJE-F1 | Rabies G | − |
| 12 | PCR Negative Control (water) | HA-Pst, gp-1F | TK-RR, gJE-F1 | Rabies G | − |

TABLE 1-continued

Results of PCR Identity Testing

| LANE | SAMPLES (DNA TEMPLATE) | PRIMERS (GEL A) | PRIMERS (GEL B) | TARGET GENE | RESULTS |
|---|---|---|---|---|---|
| 13 | PCR Positive Control (RCNV Esposito-3) | HA-Pst, gp-1F | TK-RR, gJE-F1 | Rabies G | – |
| 14 | 1kb DNA Ladder Marker | NA | NA | NA | NA |

Note:
NA, not applicable;
*–, PCR negative;
**+, PCR positive; RCNV Esposito-3 dilution used as positive control.

Conclusions

It is concluded from the results of this PCR identity testing that rabies Pasteur-Paris and CVS G genes were physically present in ha and tk loci of rRCNV-Rabies G2 genome, and that no RCNV wild type was mixed in the rRCNV-Rabies G2 MSV and X+5. This PCR testing can also be used for: 1) identity testing of RCNV wild type and of the rabies Pasteur-Paris and CVS G genes in the ha and tk loci of rRCNV-Rabies G2 genome; and 2) clone screening to differentiate rRCNV-Rabies G2 from RCNV wild type during the plaque purification of recombinant virus construction.

Example 3

In Vitro Expression of Rabies Glycoprotein in rRCNV-Rabies G2 MSV and X+5

To determine the expression of rabies glycoprotein in rRCNV-Rabies G2 MSV and passage 5-infected Vero cells, an indirect immunofluorescence assay (IFA) was performed.

| | Materials |
|---|---|
| Virus: | rRCNV-Rabies G2 MSV<br>rRCNV-Rabies G2 X + 5 |
| Vero cells: | P18-Vero-12 |
| Medium: | 1 x MEM supplemented w/ 0.05% LAH & Gent |
| Primary Antibody: | anti-Rabies IgG$_2$ mAb (commercially available from Accurate Chemical & Scientific Corp., Westbury, NY) |
| Secondary Antibody: | Fluorescein conjugated goat anti-mouse IgG (H + L) 0.5 mg |
| Diluent/wash buffer: | 0.01M PBS |
| Enhancing Solution: | 1 mg/mL p-Phenylenediamine<br>90% Glycerol<br>10% 0.01M PBS<br>0.5M Carbonate buffer<br>pH 9.0, store in dark at −20° C. |
| Fluorescence microscope: | Olympus BX51 |

Methods

1. Plant two 8-well chamber slides with $1.0 \times 10^5$ Vero cells in 500 μL of 1× Minimum Essential Medium (MEM) supplemented with 0.05% Lactalbumin Hydrolysate (LAH), 30 μL/mL Gentamicin and 5% Fetal Bovine Serum (FBS).
2. Incubate at 37° C. in a 5% $CO_2$ chamber overnight.
3. Perform serial ten-fold dilutions on samples from undiluted to $10^{-1}$ for rRCNV-Rabies G2 MSV, and from $10^{-2}$ to $10^{-4}$ for rRCNV-Rabies G2 X+5 using 1×MEM w/0.05% LAH & Gent medium.
4. Place 100 μL of each dilution into wells of chamber slide in duplicate, and leave the fourth well as a negative control.
5. Incubate for 48 hours at 37° C. in a 5% $CO_2$ chamber overnight.
6. Observe the cytopathic effect, and further examine the plaque for rabies G protein expression by IFA (Indirect Immunofluorescence Assay) using rabies G protein-specific monoclonal antibodies (G protein-specific MAb).

Results

Figure 6A:
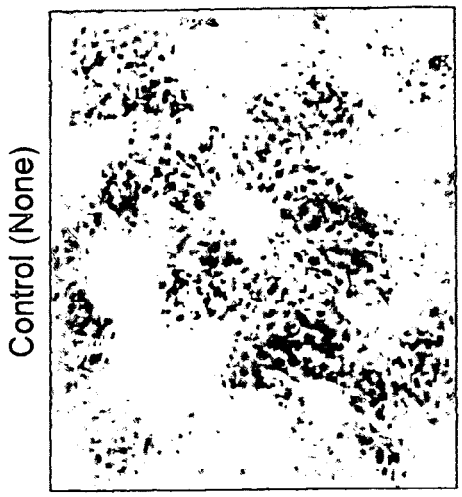
FIGS. 6A-6C reveal the in vitro expression of the rabies glycoprotein in the rRCNV-rabies G2-infected Vero cells. The cytopathic effect and fluorescence was observed in all dilutions of rRCNV-Rabies G2 MSV- and X+5-infected Vero cells (FIGS. 6A and 6B), but not in the negative control consisting of uninfected Vero cells only (FIG. 6C). This result indicated that rabies G protein was expressed and detected by rabies G protein specific monoclonal antibody in rRCNV-Rabies G2 MSV and passage 5.
Figure 6B:
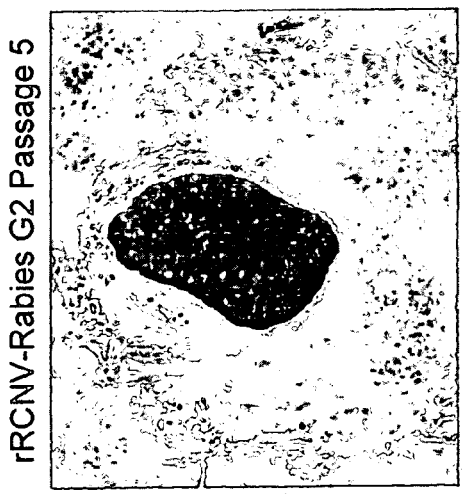
Figure 6C:
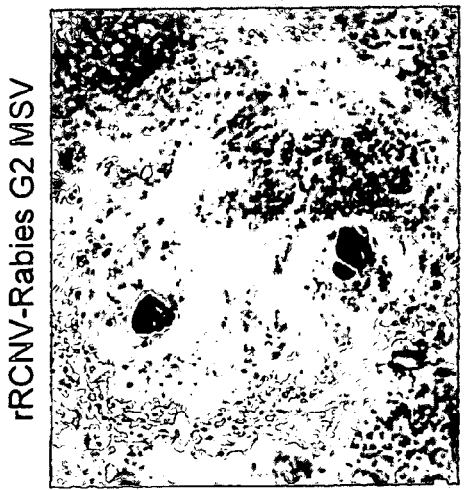

Results are shown in FIGS. 6A-6C. The cytopathic effect and fluorescence was observed in all dilutions of rRCNV-Rabies G2 MSV- and X+5-infected Vero cells (see FIGS. 6A and 6B), but not in the negative control consisting of uninfected Vero cells only (see FIG. 6C). This result indicated that rabies G protein was expressed and detected by rabies G protein specific monoclonal antibody in rRCNV-Rabies G2 MSV and passage 5.

Example 4

NIH Mouse Potency Testing

An initial comparative study of rRCNV-Rabies G2 and vKB3-JE13 (RCNV Rab-G) constructs was conducted using the standard NIH mouse potency testing. The results are summarized in the below Table 2:

TABLE 2

Results of NIH Mouse Potency Comparison of rRCNV-Rabies G2 and vKB3-JE13

| CONSTRUCT | TITER (Logs$_{10}$ TCID$_{50}$/mL) | RP VALUE |
|---|---|---|
| rRCNV-Rabies G2 | 6.3 | 6.8 |
| vKB3-JE13 | 6.4 | 0.3 |
| vKB3-JE13 | 8.3 | 9.1 |

The above results indicated that rRCNV-Rabies G2 construct of the present invention was surprisingly 23 times more potent than the vKB3-JE13 construct.

Described in more detail below, an additional study was thereafter performed using the same industry recognized techniques to determine the NIH mouse potency for the rabies vaccine, live raccoon poxvirus vector of the present invention in different formulations as compared to the previous rabies vaccines known in the art.

Materials

Virus or Vaccine:
rRCNV-Rabies G2, live vector (7.0 Logs$_{10}$ TCID$_{50}$/mL)
rRCNV-Rabies G2, live vector (6.5 Logs$_{10}$ TCID$_{50}$/mL)
vKB3-JE13 (CDC Old Construct) (7.2 Logs$_{10}$ TCID$_5$ mL)
Merial PUREVAX® Feline Rabies (a monovalent rabies glycoprotein vaccine using a live canarypox vector, commercially available from Merial, Harlow, Essex, UK)
rRCNV-Rabies G2 (6.38 Logs$_{10}$ TCID$_{50}$/mL)

Inactivated rRCNV-Rabies G2 (Pre-inactivation titer: 6.38 $Log_{10}$ $TCID_{50}$/mL)

NIH Rabies Reference Vaccine: inactivated rabies vaccine with adjuvant, a golden standard vaccine used as reference in the NIH mouse potency testing.

Methods

NIH Mouse Potency Test:

This test was performed as Standard Method "NIH Mouse Potency Test of Rabies Vaccine" with test virus/vaccine at 1:5, 1:25, 1:125 and 1:625 in the original method or at undiluted, 1:10, 1:100 and 1:1000 in the revised method. Briefly, 16 mice were vaccinated intraperitoneally (IP) with two doses of 0.5 mL of the test virus (diluted or undiluted) or NIH rabies reference vaccine at 7 days interval (otherwise indicated). 14 days following the first vaccination, all vaccinated mice were challenged intracerebrally (IC) with 0.03 mL of virulent rabies at 1:80,000 dilution (challenge virus was back titrated at 5-fold dilutions in unvaccinated mice (10 mice each dilution) to insure the proper challenge dose). All mice were observed daily for 14 days post challenge.

Results

In Table 3 below, the relative potency (RP) of rRCNV-Rabies G2 is 27.9 at 6.5 $Logs_{10}$ $TCID_{50}$/mL, and 101.9 at 7.0 $Logs_{10}$ $TCID_{50}$/mL, respectively. In below Table 4, rRCNV-Rabies G2 at 6.5 $Logs_{10}$ $TCID_{50}$/mL was more potent than Merial PUREVAX® Feline Rabies Vaccine (a monovalent rabies glycoprotein vaccine using a live canarypox vector, commercially available from Merial, Harlow, Essex, UK, which was purchased from the market for purposes of this experimental comparison), and vKB3-JE13 (CDC Old Construct) at 7.2 $Logs_{10}$ $TCID_{50}$/mL. In below Table 5, the results indicated live rRCNV-Rabies G2 is more potent than the inactivated vaccine product.

Conclusions

The NIH mouse potency test indicated that the rRCNV-Rabies G2 construct of the present invention is highly potent in the mouse model.

TABLE 3

NIH Mouse Potency Test of rRCNV-Rabies G2*

| Dilution | rRCNV-Rabies G2 (7.0 $Log_{10}$ $TCID_{50}$/mL) | rRCNV-Rabies G2 (6.5 $Log_{10}$ $TCID_{50}$/mL) | NIH Rabies Ref** Lot #757 |
|---|---|---|---|
| Undiluted | 16/16 | 16/16 | 14/16 |
| 1:10 | 16/16 | 15/16 | 11/16 |
| 1:100 | 14/16 | 12/16 | 2/16 |
| 1:1000 | 13/16 | 7/16 | 0/16 |
| Potency (RP) | 101.9 | 27.9 | 1.0 |

*Number of surviving mice at 14 DPC
**Rabies Ref: NIH rabies reference vaccine

TABLE 4

NIH Mouse Potency Comparison of rRCNV-Rabies G2, vKB3-JE13 and Merial PUREVAX ® Feline Rabies Vaccine*

| Dilution | rRCNV-Rabies G2 (6.5 $Log_{10}$ $TCID_{50}$/mL) | vKB3-JE13 (7.2 $Log_{10}$ $TCID_{50}$/mL) | Merial PUREVAX® ≥Minimal Release Titer | NIH Rabies Reference Vaccine Lot #764 |
|---|---|---|---|---|
| Undiluted | 16/16 | 15/15 | 16/16 | 16/16 |
| 1:10 | 14/16 | 12/15 | 16/16 | 15/16 |
| 1:100 | 12/15 | 10/16 | 10/16 | 7/16 |
| 1:1000 | 4/16 | 2/16 | 3/16 | 0/16 |
| Potency (RP) | 3.55 | 1.50 | 2.74 | 1.0 |

*Number of surviving mice at 14 DPC.

TABLE 5

NIH Mouse Potency Test of Live/Inactivated rRCNV-Rabies G2*

| Dilution | Live rRCNV-Rabies G2** One Dose | Live rRCNV-Rabies G2** Two Doses | Inactivated rRCNV-Rabies G2 (without Adjuvant)*** Two Doses | NIH Rabies Reference Vaccine Lot #768 (Two doses) |
|---|---|---|---|---|
| 1:5 | 11/16 | 16/16 | 15/16 | 16/16 |
| 1:25 | 3/16 | 16/16 | 9/16 | 9/16 |
| 1:125 | 1/15 | 9/16 | 0/16 | 2/16 |
| 1:625 | 0/16 | 5/16 | 1/16 | 0/16 |
| Potency (RP) | 0.30 | 6.76 | 0.82 | 1.0 |

*Number of surviving mice at 14 DPC.
**Live rRCNV-Rabies G2 at 6.38 $Log_{10}$ $TCID_{50}$/mL.
***Inactivated rRCNV-Rabies G2 (without adjuvant) at pre-inactivation titer of 6.38 $Log_{10}$ $TCID_{50}$/mL.

Example 5

Genetic Stability Testing of rRCNV-Rabies G2 MSV and X+5 by PCR Testing

The objective of the experimental study was to determine the genetic stability of rRCNV-Rabies G2 MSV and X+5 by PCR testing.

Materials

1. Viruses:
    a) rRCNV-Rabies G2 MSV
    b) rRCNV-Rabies G2 X+5
2. Primers:
    a) For amplification of 1806-bp Pasteur-Paris rabies G gene and its partial flanking region at ha locus
    HA-Pst: 5'-TCA TTG ACA TCT GGA GAT GCA GGT ACT-3' (which corresponds to SEQ ID NO:3)
    PW-04: 5'-AGA ACA TTA CCC ACA TGA-3' (which corresponds to SEQ ID NO:9)
    b) For amplification of 1910-bp Challenge Virus Standard (CVS) rabies G gene and its partial flanking region at tk locus
    TK-RR: 5'-GM AAG GAA GCC TCC TTA AAG-3' (which corresponds to SEQ ID NO:7)
    PW-03: 5'-TCT CAC AAT CAC CAC TTT CAT-3' (which corresponds to SEQ ID NO:10)
3. Kits/reagents for DNA purification and PCR cloning
    a) QIAGEN DNeasy Tissue Kit (commercially available from Qiagen Inc., Valencia, Calif., USA)
    b) Applied Biosystems AmpliTaq Gold DNA polymerase (commercially available from Applied Biosystems, Foster City, Calif.)
    c) Amersham-Pharmacia-Biotech Inc. dNTPs (commercially available from Amersham Biosciences, Piscataway, N.J.)

4. Applied Biosystems GeneAmp PCR System 9700 (commercially available from Applied Biosystems, Foster City, Calif.)

Methods

A. DNA Preparation

The preparation of genomic DNA from rRCNV-Rabies G2 MSV and X+5 was performed using a QIAGEN DNeasy Tissue kit (commercially available from Qiagen Inc, Valencia, Calif., USA) as described in the instruction manual provided by Qiagen.

B. PCR Testing

In this PCR testing, the primers HA-Pst and PW-04 were used to amplify 1806-bp Pasteur-Paris rabies G gene and its insertion flanking region at ha locus, and the primers TK-RR and PW-03 were used to amplify 1910-bp CVS rabies G gene and its insertion flanking region at tk locus.

1. For each PCR reaction, prepare the following reaction mixture:

| | |
|---|---|
| 5 μL | 10 × PCR Buffer |
| 3 μL | 25 mM MgCl$_2$ |
| 5 μL | 2 mM dNTPs |
| 5 μL | each of primers (10 μM) |
| 5 μL | DNA template |
| 0.5 μL | 5 units/μL ABI AmpliTaq Gold |
| 21.5 μL | ddH$_2$0 |

2. Incubate samples in thermal cycler at 95° C. for 10 min to completely denature the DNA template.
3. Amplify the target template for 35 cycles:

| Step | Temp | Time |
|---|---|---|
| Denaturation | 94° C. | 1.0 min |
| Annealing | 59° C. | 1.0 min |
| Extension | 72° C. | 2.0 min |

4. Hold samples at 72° C. for an additional 5 min.
5. Hold samples at 4° C. indefinitely.

C. Agarose Gel Electrophoresis

1. Combine 10 μL of each PCR product with 2 μL of loading buffer.
2. Run samples on 1% agarose gel with Promega Lambda DNA/Hind III and 1 kb DNA ladder as markers (both products are commercially available from Promega Corporation, Madison, Wis.) (see FIG. 7).

Results

PCR results indicated that 1806-bp (ha locus) and 1910-bp (tk locus) identical bands were amplified from rRCNV-Rabies G2 MSV and X+5 (see FIG. 7). The result indicated that no noticeable insertion or deletion occurs within the insertion flanking regions and rabies G gene of CVS rabies strain at tk locus, and of Pasteur-Paris rabies strain at ha locus, respectively, from rRCNV-Rabies G2 MSV and X+5. The difference in band density between rRCNV-Rabies G2 MSV and X+5 is because viral titer of the passage 5 was about 10,000 times higher than the Master Seed. The results are summarized in the below Table 6:

TABLE 6

Results of Genetic Stability Testing of rRCNV-Rabies G2 MSV and X + 5

| LANE | SAMPLES | PRIMERS | GENE TARGET | RESULTS |
|---|---|---|---|---|
| 1 | | | Lambda/HindIII Marker | |
| 2 | rRCNV-Rabies G2 MSV | HA-Pst, PW-04 | 1806-bp Pasteur- | + |
| 3 | rRCNV-Rabies G2 X + 5 | HA-Pst, PW-04 | Paris rabies G and its | + |
| 4 | Negative control (water) | HA-Pst, PW-04 | flanking region | − |
| 5 | rRCNV-Rabies G2 MSV | TK-RR, PW-03 | 1910-bp CVS rabies | + |
| 6 | rRCNV-Rabies G2 X + 5 | TK-RR, PW-03 | G and its flanking | + |
| 7 | Negative control (water) | TK-RR, PW-03 | region | − |
| 8 | | | 1 kb DNA ladder Marker | |

Conclusions

It is concluded from the PCR testing that rRCNV-Rabies G2 MSV is genetically stable under pre-manufacture scale up procedure to passage 5.

Example 6

Phenotypic Stability Testing of rRCNV-Rabies G2 MSV and X+5 by Blue Plaque Assay This study examines whether the rRCNV-Rabies G2 MSV (Master Seed Virus) was phenotypically stable under pre-manufacture scale up procedure to passage 5 (rRCNV-Rabies G2 X+5) by blue plaque assay.

Method

A. Seed Vero Cells

1 Cells are planted on 100 mm dishes at a concentration of $7 \times 10^5$/mL (10 mL in 1×MEM/0.05% LAH/Gent Medium+5% FBS) and grown overnight so cells reach approximately 80% confluency for infection.

B. Virus Dilution

2. Thaw out viruses at room temperature and optionally sonicate on ice for 15 seconds three times.
3. Make serial 1 0-fold dilutions in 1×MEM/0.05% LAH/Gent Medium:
a) rRCNV-Rabies G2 MSV was diluted to $10^{-1}$,
b) rRCNV-Rabies G2 X+5 was diluted to $10^{-5}$.

C. Infection

4. Remove the medium from the 100 mm dishes and rinse twice with 6 mL of 0.01M PBS.
5. Remove all fluid from the plates and add diluted virus to each dish.
a) For MSV: 1 mL of $10^0$ and $10^{-1}$ diluted virus was added in triplicate.
b) For X+5: 1 mL of $10^{-3}$, $10^{-4}$, and $10^{-5}$ diluted virus was added in triplicate.
6. Add 4 mL of 1×MEM/0.05% LAH/Gent Medium to each dish so that the total volume in each dish is 5 mL.
7. Incubate for 2 hours at 37° C. and 5% CO$_2$, and let virus infect the Vero cells.

D. Agar Overlay

8. Add 10% FBS to the 2×MEM/0.05% LAH/Gent Medium and warm to 42° C.
9. After melting, Noble agar is cooled to 56° C.
10. Mix equal volumes of 2.5% Noble agar with 2×MEM/0.05% LAH/Gent Medium+10% FBS, and allow it to sit at room temperature in a beaker of 56° C. water for 10 min.

11. Remove the entire medium from plates at Step 7 after 2-hr infection, and overlay the cell monolayer with 15 mL of growth medium/Noble agar mixture from Step 10
12. Allow the agar to solidify for 10-15 min.
13. Incubate dishes at 37° C. and 5% $CO_2$.

E. Staining

After a 5 day-incubation, dishes are overlayed with 7 mL of the staining solution as follows:

14. Prepare staining solution (100 mL): 50 mL of 2.5% Noble Agar, 50 mL of PBS, and 1 mL of 50 mg/mL X-Gal.
15. Before mixing, Noble agar is cooled to 56° C. and PBS is warmed to 42° C. Mix PBS and X-Gal first, and then add X-Gal/PBS into Noble agar. The mixture sits at room temperature in a beaker containing 56° C. water for 10 min.
16. After 10 min, add 7 mL of staining solution onto each plate.
17. Allow the agar to solidify for 10-15 min.
18. Incubate at 37° C. for 4-6 hours
19. Count the blue plaques and record the digital images.

Results

The total blue plaques were counted on each plate and are summarized in the below Table 7. No white plaques were observed in any plate. The digital images of blue plaques from rRCNV-Rabies G2 MSV and X+5 in Vero cells are shown in FIGS. 8A and 8B, respectively. The calculated titers of rRCNV-Rabies G2 MSV and X+5 are shown below.

Conclusions

Neither white plaques nor significant titer loss were observed in rRCNV-Rabies G2 MSV and X+5. This result indicated that rRCNV-Rabies G2 MSV is phenotypically stable under pre-manufacture scale up procedure to passage 5.

TABLE 7

Blue plaque count of rRCNV-Rabies G2 MSV and X + 5 in Vero cells

| Virus | Dilution | # of Blue plaque | | | | Titer |
|---|---|---|---|---|---|---|
| | | 1 | 2 | 3 | Ave | pfu/mL |
| rRCNV-Rabies G2 MSV | $10^0$ | 224 | 159 | 112 | 165 | 2.22 |
| | $10^{-1}$ | 29 | 3 | 14 | 15 | 2.18 |
| rRCNV-Rabies G2 X + 5 | $10^{-3}$ | Too many to be counted | | | | |
| | $10^{-4}$ | 173 | 220 | 217 | 203 | 6.31 |
| | $10^{-5}$ | 12 | 12 | 14 | 13 | 6.11 |

Example 7

Dose Titration Study of rRCNV-Rabies G2 in Cats

This study was performed to demonstrate the short-term (3 months) efficacy of the rRCNV-Rabies G2 vaccine.

Dose titration study of rRCNV-Rabies G2 was conducted in 40 cats. The adjuvant-free test vaccine consisted of live rRCNV-Rabies G2 and 1×MEM (Minimum Essential Medium). The vaccine was stored at 2-7° C. In this study, there were 4 groups (10 cats at 12 weeks of age for each group): cats in Groups 1-3 were administered subcutaneously (SQ) a single dose (1 mL/dose) of 6.5, 5.5 and 4.5 $Log_{10}$ $TCID_{50}$/mL of rRCNV-Rabies G2, respectively, while cats in Group 4 (Control) were not vaccinated. Cats were 12 weeks of age at the time of vaccination. Three months following vaccination, cats were challenged with rabies NYC street strain. At 42 days post challenge, no vaccinated cat died while 80% (8/10) of the control cats died due to rabies infection. Showing that 100% of the cats vaccinated at three different dosages were protected, the excellent results of this study indicated that the rRCNV-Rabies G2 construct of this invention was able to induce full protection against rabies challenge in cats.

In this dose titration study, there were four groups: cats (n=3×10) in the three vaccinate groups were administrated a single-dose of Rabies Vaccine, Live Raccoon Poxvirus Vector (rRCNV-Rabies G2) with three different titers (6.50, 5.39 and 4.42 $Log_{10}TCID_{50}$/mL/dose), respectively, at 12 weeks of age, and cats (n=10) in the control group were not vaccinated. On 28, 63, and 98 days post vaccination, all cats were bled and individual serum samples tested for neutralizing antibodies to rabies virus. Significant rabies neutralizing antibody titers were observed in the majority of vaccinated cats while non-vaccinated cats remained rabies sero-negative until challenge.

More than three months following the vaccination (at 98 DPV), all cats (30 vaccinates and 10 controls) were challenged with a 1:150 direct dilution of rabies street NYC strain Lot 92-5, supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). All challenged cats were observed daily for 42 days and the rabies-associated clinical signs and mortality recorded. Challenge results demonstrated that 8/10 (80%) controls died due to rabies while 10/10 (100%) vaccinates in each vaccinate group remained well for a period of 42 days. There was a significant difference in mortality between the vaccinated and control groups. The vaccine efficacy was 100%, for all 3 vaccinate groups.

In summary, results from this dose titration study demonstrated that the recombinant rabies vaccine of the present invention using the live raccoon poxvirus vector is efficacious even at a titer as low as 4.42 $Log_{10}TCID_{50}$/mL (per dose) in the prevention of rabies for at least three months following a single vaccination, in cats.

More than three months following the vaccination (at 98 DPV), all cats were challenged with a 1:150 direct dilution of rabies street challenge virus (Lot 92-5, 3-1-92, NYC strain in Fox) supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). Briefly, the animals were tranquilized before the inoculation and then intramuscularly inoculated with 0.5 mL of the diluted challenge into each masseter muscle (total 1.0 mL). The animals were placed and secured in individual cages within the rabies challenge area for the 42-day observation period. The 42-day post challenge observation period was justified by previous rabies challenge results that all rabid animals died in the first 4 weeks post challenge.

The lethal challenge dose was determined to be acceptable by the mortality rate of the control cats in this study. The challenge results indicated that 8/10 (80%) controls died due to rabies. Thus this was a valid challenge test.

Six mL of whole blood from each cat was collected for serum at 0 day post vaccination (DPV), 28 DPV, 63, and 98 DPV.

Serum samples were tested by the Rapid Fluorescent Focus Inhibition Test (RFFIT), a tissue culture fluorescent antibody procedure published by NVSL (National Veterinary Services Laboratories of the United States Department of Agriculture), to determine serum neutralization (SN) titers against rabies virus.

The rRCNV-rabies G2 vaccine used in this study was titrated in five replicates on Vero cells. The average titer of the test vaccines was 6.50 (V1), 5.39 (V2), and 4.42 (V3) $Log_{10}TCID_{50}$/mL (per dose), respectively.

On 28, 63, and 98 days post vaccination, all cats were bled and individual serum samples tested for neutralizing antibodies to rabies virus by the RFFIT. Significant rabies neutralizing antibodies titers were observed in the majority of vaccinated cats while non-vaccinated cats remained rabies sero-negative until challenge.

Following challenge, cats were observed daily for 42 days, and rabies-associated clinical signs and death were recorded. 8/10 (80%) non-vaccinated control cats died or showed rabies signs, indicating that this was a valid challenge test. By contrast, all vaccinated cats (10/10, 100%) in three groups remained well. It was found that the death of 8 cats due to rabies infection took place between 12 DPC and 25 DPC. There was a significant difference in mortality between vaccinates and control groups. The vaccine efficacy was 100%, for all 3 vaccinate groups.

It is concluded from this dose titration study that the new rabies vaccine using the live raccoon poxvirus vector (rRCNV-rabies G2) is efficacious even at a titer as low as 4.42 $Log_{10}TCID_{50}$/mL per dose, in the prevention of rabies for at least three months following single vaccination, in cats.

Example 8

Dose Titration Study of rRCNV-Rabies G2 in Dogs

The objectives of this study were to demonstrate the short-term (3 months) efficacy of the rRCNV-Rabies G2 vaccine.

Dose titration study of rRCNV-Rabies G2 was conducted in 40 dogs. The test vaccine consisted of live rRCNV-Rabies G2 and 1×MEM without adjuvants, In this study, there were 4 groups (10 dogs at 12 weeks of age for each group): dogs in Groups 1-3 were administered subcutaneously (SQ) a single dose (1 mudose) of 6.5, 5.5 and 4.5 $Logs_{10}$ $TCID_{50}$/mL of rRCNV-Rabies G2, respectively, while dogs in Group 4 (Control) were not vaccinated. Dogs were 12 weeks of age at the time of vaccination. Three months following vaccination, dogs were challenged with rabies NYC street strain. At 42 days post challenge, 0% (0/10) in Group 1, 10% (1/10) in Group 2 and 30% (3/10) in Group 3 of dogs died while 100% (10/10) of the control dogs died due to rabies infection. The excellent results in which 100% (10/10) of dogs in Group 1 were protected against infection indicate that the rRCNV-Rabies G2 of this invention elicited and successfully achieved full protection against rabies challenge when dogs were vaccinated with an effective immunizing dosage of 6.5 $Logs_{10}$ $TCID_{50}$/mL. Group 2 demonstrating that 90% (9/10) dogs vaccinated with the effective amount of 5.5 $Log_{10}$ $TCID_{50}$/mL were protected against infection also had a satisfactory outcome. This study shows that standard dose titration techniques can establish the effective immunizing amount or dosage of the rRCNV-Rabies G2 construct of the invention having satisfactory results that would meet the U.S. government requirements for acceptance of a live rabies vaccine (9 C.F.R. §113.312).

In this dose titration study, there were four groups: Dogs (n=3×10) in the three vaccinate groups were administrated a single-dose of Rabies Vaccine, Live Raccoon Poxvirus Vector (rRCNV-Rabies G2) with three different titers (6.50, 5.39 and 4.42 $Log_{10}TCID_{50}$/mL/dose), respectively, at 12 weeks of age, and dogs (n=10) in the control group were not vaccinated. On 28, 64, and 91 days post vaccination, all dogs were bled and individual serum samples tested for neutralizing antibodies to rabies virus. Significant rabies neutralizing antibodies titers were observed in the majority of vaccinated dogs while non-vaccinated dogs remained rabies sero-negative until challenge.

More than three months following the vaccination (at 98 DPV), all dogs (30 vaccinates and 10 controls) were challenged with a 1:$10^{-5}$ direct dilution of rabies street NYC strain (NYC strain in Fox), supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). Briefly, the animals were tranquilized before the inoculation and then intramuscularly inoculated with 0.5 mL of the diluted challenge into each masseter muscle (total 1.0 mL). All challenged dogs were observed daily for 42 days and the rabies-associated clinical signs and mortality recorded. Challenge results demonstrated that 10/10 (100%) controls died due to rabies while 10/10 (100%), 9/10 (90%), and 7/10 (70%) dogs vaccinated at a dose of 6.50, 5.39 and 4.42 $Log_{10}TCID_{50}$/mL/dose, respectively, remained well for a period of 42 days. There was a significant difference in mortality between the vaccinated and control groups. The vaccine efficacy was 100% (V1), 90% (V2) and 70% (V3), respectively.

In summary, results from this dose titration study demonstrate that the novel rabies vaccine using the live RCNV is efficacious even at a titer as low as 5.39 $Log_{10}TCID_{50}$/mL (per dose), as an aid in the prevention of rabies for at least three months following a single vaccination, in dogs.

The lethal challenge dose was determined to be acceptable by the mortality rate of the control dogs in this study. The challenge results indicated that 10/10 (100%) controls died due to rabies. This was obviously a valid challenge test.

Serum samples were taken. Eight mL of whole blood from each dog was collected for serum at 0 day post vaccination (DPV), 28 DPV, 63, and 91 DPV. Serum samples were tested by the Rapid Fluorescent Focus Inhibition Test (RFFIT), a tissue culture fluorescent antibody procedure published by NVSL (National Veterinary Services Laboratories of the United States Department of Agriculture), to determine serum neutralization (SN) titers against rabies virus.

The rRCNV-Rabies G2 used in this study was titrated in five replicates on Vero cells. The average titer of the test vaccines was 6.50 (V1), 5.39 (V2), and 4.42 (V3) $Log_{10}TCID_{50}$/mL (per dose), respectively.

On 28, 63, and 91 days post vaccination, all dogs were bled and individual serum samples tested for neutralizing antibodies to rabies virus by the RFFIT. Significant rabies neutralizing antibodies titers were observed in the majority of vaccinated dogs while non-vaccinated dogs remained rabies sero-negative until challenge.

Post-Challenge Observations: Following challenge, dogs were observed daily for 42 days, and rabies-associated clinical signs and death were recorded. 10/10 (100%) non-vaccinated control dogs died or showed rabies signs, indicating that this was a valid challenge test. By contrast, 10/10 (100%), 9/10 (90%), and 7/10 (70%) dogs vaccinated at a dose of 6.50, 5.39 and 4.42 $Log_{10}TCID_{50}$/mL/dose, respectively, remained well for a period of 42 days. It was interestedly found that the death of 14 dogs due to rabies infection took place between 13 DPC and 25 DPC. There was a significant difference in mortality between the vaccinated and control groups. The vaccine efficacy was 100% (V1), 90% (V2) and 70% (V3), respectively.

It is concluded from this dose titration study that the Rabies Vaccine, Live Raccoon Poxvirus Vector product (rRCNV-rabies G2) is efficacious even at a titer as low as 5.39 $Log_{10}TCID_{50}$/mL, as an aid in the prevention of rabies for at least three months following single vaccination, in dogs.

Example 9

One-year Duration of Immunity Study of Rabies Vaccine (Low Dose and Regular Dose), Live Raccoon Poxvirus Vector, in Cats To determine the protective dose for use of the vaccine product in cats, two, one-year duration of immunity (DOI) studies of rRCNV-Rabies G2 vaccine were conducted, and the efficacy was demonstrated by virulent rabies virus challenge. The objective of these studies was to demonstrate the efficacy and the immunogenicity of the adjuvant-free recombinant rabies vaccine in cats after a one-year duration following a single vaccination, using two different doses of the rabies virus vaccine, a low dose of 5.38 $Log_{10}TCID_{50}$/ml and a regular dose of 6.28 $Log_{10}TCID_{50}$/ml.

A. Low Dose Study Summary

Briefly, in this one-year duration of immunity (DOI) study, there were two groups: cats (n=28) in the vaccinate group were administrated a single-dose of Rabies Vaccine, Live Raccoon Poxvirus Vector (VS Code 1901.R5) at 12 weeks of age, and cats (n=13) in the control group were not vaccinated. On 28, 91, 183, 272, and 365 days post vaccination, all cats were bled and individual serum samples tested for neutralizing antibodies to rabies virus. More than one year (421 days) following the vaccination, 35 cats (25 vaccinates and 10 controls) were randomly chosen for rabies challenge. The challenge material was prepared by a 1:40 direct dilution of rabies street NYC strain Lot 92-5, supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). All challenged cats were observed daily for 90 days and the rabies-associated clinical signs and mortality recorded. The brain of each dead or euthanized cat was examined for rabies by fluorescent antibody (FA) test. APHIS/CVB inspectors were on site to observe all procedures for vaccination, challenge material preparation and challenge in this study.

The Rabies Vaccine, Live Raccoon Poxvirus Vector was titrated in five replicates with an average titer of 5.38 $Log_{10}TCID_{50}$/mL (per dose), referred to as the "low" dose. Significant rabies neutralizing antibodies titers were observed in the vaccinated cats while non-vaccinated cats remained rabies sero-negative until challenge.

Challenge results demonstrated that 8/10 (80%) of non-vaccinated controls died due to rabies while only 3/25 or 12% of vaccinated cats died due to rabies and 22/25 (88%) vaccinates remained well for a period of 90 days. The brains of the 9 dead control cats were confirmed as positive for rabies virus by FA testing. There was a significant difference in mortality between the vaccinated and control groups. The vaccine efficacy for prevention of rabies was 85% (95% CI 55, 97). This is a satisfactory test to meet the statutory requirements (Title 9, Code of Federal Regulations and EP) for rabies vaccine efficacy.

Protocol for Low Dose Study

The protocol for this study is described in further detail below:

There were 28 test animals and 13 control animals at the time of vaccination. Thirty-five of these cats (25 vaccinates and 10 controls) were randomly selected for challenge. Cats were twelve weeks of age at the time of vaccination. The lyophilized rRCNV-Rabies G2 vaccine for this study was stored at 2-7° C. The lyophilized vaccine consisted of live rRCNV-Rabies G2 and SGGK stabilizer. This test recombinant rabies vaccine was adjuvant-free. The test vaccine was titrated in five replicate assays in order to establish the dose administrated to the cats in this study. The average titer of the vaccine was 5.38 $Log_{10}TCID_{50}$/mL (per dose).

There were 41 experimental units (28 vaccinates and 13 controls) at the time of vaccination. Thirty-five of these cats (25 vaccinates and 10 controls) were randomly selected for challenge. The animals were randomized, according to litter, into vaccinates and controls. The randomization process was completed by random number assignment to the animals of each litter using Microsoft Excel. The random numbers in each litter were sorted in ascending order for the placement of animals from that litter into each group. The process was repeated until animals from all litters had been randomized.

This was a randomized complete block design. 41 cats were randomly divided into two groups as follows:

| Group | VACCINE | # OF ANIMALS* |
|---|---|---|
| Vaccinates | rRCNV-Rabies G2 (5.38 $Log_{10}TCID_{50}$/mL/Dose) | 28 |
| Controls | None | 13 |

*25 vaccinates and 10 controls were randomly chosen for rabies challenge.

Vaccination Protocol

The lyophilized vaccine was rehydrated by the 1.0 mL sterile water diluent supplied. The vaccination route was subcutaneous. Each animal in the vaccinate group was given one dose (1 mL/dose) of the vaccine in the nape of the neck. The control animals were not vaccinated. APHIS/CVB inspector was on site to observe the whole procedure of vaccination. For the sake of the long study duration, all cats were vaccinated with Fel-O-Vax PCT according to label direction.

Challenge Protocol

More than one year (421 DPV) following the vaccination with rRCNV-Rabies G2 vaccine, 10 controls and 25 vaccinates were randomly chosen for challenge. The randomization was performed using the random number generator in Microsoft Excel: the vaccinates were assigned numbers, sorted and the highest numbered cats excluded from the challenge until the number of vaccinates equaled 25; analogous procedure was used to reduce the number of controls to 10. As a result, three controls and two vaccinates were randomly excluded from the challenge phase. In addition, one additional vaccinate that had various skin diseases, was excluded from this study before challenge.

All 35 cats were challenged with a 1:40 direct dilution of rabies street challenge virus (NYC strain in Fox) supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). Briefly, the animals were tranquilized before the inoculation and then intramuscularly inoculated with 0.5 mL of the diluted challenge into each masseter muscle (total 1.0 mL). The animals were placed and secured in individual cages within the rabies challenge area for the 90-day observation period. APHIS/CVB inspector was on site to observe the whole procedures of challenge virus dilution and rabies challenge.

The lethal challenge dose was determined to be acceptable by the mortality rate of the control cats in this study. The challenge results indicated that 8/10 (80%) controls died due to rabies. Thus this was a valid challenge test.
Sample Collection and Testing
Serum Samples Serum samples were taken. Six mL of whole blood from each cat was collected for serum at 0 day post vaccination (DPV), 28 DPV, 91 DPV, 183 DPV, 272 DPV, and 365 DPV.
Serology Testing Serum samples were tested by the Rapid Fluorescent Focus Inhibition Test (RFFIT), a tissue culture fluorescent antibody procedure published by NVSL (National Veterinary Services Laboratories of the United States Department of Agriculture), to determine serum neutralization (SN) titers against rabies virus.
Testing of Animals During the post-challenge observation period, all animals euthanized or found dead were tested for rabies virus. More particularly, the brain was collected (the ammons horn), sectioned, processed and stained by a fluorescent antibody technique.
Results
Vaccine Titration The vaccine used in this study was titrated in five replicates on Vero cells by standard techniques. The average titer of the test vaccine was 5.38 $Log_{10}TCID_{50}$/mL (per dose).
Neutralizing Antibody to Rabies On 28, 91, 183, 272, and 365 days post vaccination, all cats were bled and individual serum samples tested for neutralizing antibodies to rabies virus by the RFFIT. Significant rabies neutralizing antibodies titers were observed in the majority of vaccinated cats while non-vaccinated cats remained rabies sero-negative until challenge.
Post-Challenge Obserations Following challenge, cats were observed daily for 90 days, and rabies-associated clinical signs and death were recorded. It was found that 8/10 (80%) non-vaccinated control cats died or showed rabies signs, indicating that this was a valid challenge test. By contrast, only 3/25 (12%) vaccinated cats died or showed rabies signs. It was found that the death of 11 cats due to rabies infection took place between 10 DPC and 20 DPC. At the end of the study, 22 vaccinates and 2 controls remained well. There was a significant difference in mortality between vaccinate and control groups. The preventable fraction was 85% (95% CI 55, 97).
Fluorescent Antibody Test The brains of the euthanized cats noted above (8 control and 3 vaccinates) tested positive for rabies virus, thereby confirming that the death of these 11 cats was due to rabies infection.
Conclusions It is concluded from this one-year DOI study that the Rabies Vaccine, Live Raccoon Poxvirus Vector is efficacious even at a titer as low as 5.38 $Log_{10}TCID_{50}$/mL, as an aid in the prevention of rabies for at least one year following single vaccination of cats.
B. Regular Dose Study Summary The one year duration of immunity study was repeated but with the average titer of the recombinant vaccine at 6.28 $Log_{10}TCID_{50}$/mL (per dose), referred to as the "regular" dose. The lyophilized vaccine consisted of live rRCNV-Rabies G2 and SGGK stabilizer. This recombinant rabies vaccine was adjuvant-free. The test vaccine was titrated in five replicate assays in order to establish the dose administered into the cats in this study.

In this one-year duration of immunity (DOI) study, there were two groups: cats (n=28) in the vaccinate group were administered a single-dose of Rabies Vaccine, Live Raccoon Poxvirus Vector (VS Code 1901.R5) at 12 weeks of age, and cats (n=13) in the control group were not vaccinated. On 31, 91, 182, 273, and 364 days post vaccination, all cats were bled and individual serum samples tested for neutralizing antibodies to rabies virus. More than one year (399 days) following the vaccination, 35 cats (25 vaccinates and 10 controls) were randomly chosen for rabies challenge. The challenge material was prepared by a 1:40 direct dilution of rabies street NYC strain Lot 92-5, supplied by the NVSL-BVL, USDA. All challenged cats were observed daily for 90 days and the rabies-associated clinical signs and mortality recorded. The brain of each dead or euthanized cat was examined for rabies by fluorescent antibody (FA) test. APHIS/CVB inspectors were on site to observe all procedures for vaccination, challenge material preparation and challenge in this study.

Rabies Vaccine, Live Raccoon Poxvirus Vector was titrated in five replicates with an average titer of 6.28 $Log_{10}TCID_{50}$/mL (per dose). Significant rabies neutralizing antibodies titers were observed in all vaccinated cats while non-vaccinated control cats remained rabies sero-negative until challenge.

Challenge results demonstrated that 9/10 (90%) controls died due to rabies while 25/25 (100%) vaccinates remained well for a period of 90 days. The brains of the 9 dead control cats were confirmed as positive for rabies virus by FA testing. There was a significant difference in mortality between the vaccinated and control groups. The vaccine efficacy for prevention of rabies was 100% (95% CI 84, 100). This is a satisfactory test to meet the 9 CFR and EP requirements for rabies vaccine efficacy.

In summary, results from this one-year DOI study demonstrate that Fort Dodge Animal Health's Rabies Vaccine, Live Raccoon Poxvirus Vector is efficacious at a titer of 6.28 $Log_{10}TCID_{50}$/mL (per dose) in the prevention of rabies for at least one year following a single vaccination.
Protocol for Regular Dose Study This was a randomized complete block design. 41 cats were randomly divided into two groups as follows:

| Group | VACCINE | # OF ANIMALS* |
|---|---|---|
| Vaccinates | rRCNV-Rabies G2 (6.28 $Log_{10}TCID_{50}$/mL/Dose) | 28 |
| Controls | None | 13 |

*25 vaccinates and 10 controls were randomly chosen for rabies challenge.

Vaccination Protocol

The lyophilized vaccine was rehydrated by the 1.0 mL sterile water diluent supplied. The vaccination route was subcutaneous. Each animal in the vaccinate group was given one dose (1 mL/dose) of the vaccine in the nape of the neck. The control animals were not vaccinated. APHIS/CVB inspector was on site to observe the whole procedure of vaccination. For the sake of the long study duration, all cats were vaccinated with Fel-O-Vax PCT according to label direction.
Challenge Protocol More than one year (399 days) following the vaccination, 10 controls and 25 vaccinates were randomly chosen for challenge. The randomization was performed using the random number generator in Microsoft Excel: the vaccinates were assigned numbers, sorted and the highest numbered cats excluded from the challenge until the number of vaccinates equaled 25; analogous procedure was used to reduce the number of controls to 10. As a result, three controls were randomly excluded from the challenge phase and transferred to QC for safety testing. Three vaccinates were also randomly excluded from the challenge phase and euthanized.

All 35 cats were challenged with a 1:40 direct dilution of rabies street challenge virus (NYC strain in Fox) supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). Briefly, the animals were tranquilized before the inoculation and then intramuscularly inoculated with 0.5 mL of the diluted challenge into each masseter muscle (total 1.0 mL). The animals were placed and secured in individual cages within the rabies challenge area for the 90-day observation period. APHIS/CVB inspector was on site to observe the whole procedures of challenge virus dilution and rabies challenge.

The lethal challenge dose was determined to be acceptable by the mortality rate of the control cats in this study. The challenge results indicated that 9/10 (90%) controls died due to rabies. Thus this was a valid challenge test.

Results
Vaccine Titration

The vaccine used in this study was titrated in five replicates on Vero cells. The average titer of the test vaccine was 6.28 $Log_{10}TCID_{50}$/mL (per dose).

Sample Collection and Testing
Serum Samples

Six milliliters of whole blood was collected at 0 day post vaccination and at days 31, 91, 182, 273, and 364 days post vaccination.

Serology Testing

On 31, 91, 182, 273, and 364 days post vaccination, all cats were bled and individual serum samples tested for neutralizing antibodies to rabies virus by the RFFIT. Significant rabies neutralizing antibodies titers were observed in the majority of vaccinated cats while non-vaccinated cats remained rabies sero-negative until challenge.

Post Challenge Observations

Following challenge, cats were observed daily for 90 days, and rabies-associated clinical signs and death were recorded. It was seen that 9/10 (90%) non-vaccinated control cats died or showed rabies signs, indicating that this was a valid challenge test. By contrast, none (0/25, 0%) of vaccinated cats died or showed rabies signs. It was found that the death of the 9 cats due to rabies infection took place between 10 DPC and 15 DPC. At the end of study, all 25 vaccinates and one control remained well. There was a significant difference in mortality between vaccinate and control groups. The preventable fraction was 100% (95% CI 84, 100).

Fluorescent Antibody Test

The dead and euthanized cats during the period of post-challenge observations were securely transported to the Veterinary Diagnostic Laboratory at the Iowa State University College of Veterinary Medicine, for fluorescent antibody testing. The brains of the 9 dead cats (9 controls) were tested positive for rabies virus. These results further confirmed that the death of the 9 cats was due to rabies.

CONCLUSION

It is concluded from the results of this one-year DOI study that the new Rabies Vaccine, Live Raccoon Poxvirus Vector (rRCNV-Rabies G2 construct) is efficacious in cats at a titer of 6.28 $Log_{10}TCID_{50}$/mL in the prevention of rabies for at least one year following a single vaccination.

Example 10

One-year Duration of Immunity Study of Rabies Vaccine, Live Raccoon Poxvirus Vector, in Dogs To determine the protective dose of the new vaccine in dogs, a one-year duration of immunity (DOI) study of rRCNV-Rabies G2 vaccine was conducted, and the efficacy demonstrated by virulent rabies virus challenge in dogs. The objective of this study was to demonstrate the efficacy of the adjuvant-free recombinant rabies vaccine in dogs after a one-year duration following a single vaccination.

Briefly, in this one-year duration of immunity (DOI) study, there were two groups: dogs (n=28) in the vaccinate group were administrated a single-dose of Rabies Vaccine, Live Raccoon Poxvirus Vector (VS Code 1901.R5) at 12 weeks of age, and dogs (n=13) in the control group were not vaccinated. On 28, 91, 182, 273, and 365 days post vaccination, all dogs were bled and individual serum samples tested for neutralizing antibodies to rabies virus. More than one year (420 days) following the vaccination, 35 dogs (25 vaccinates and 10 controls) were randomly chosen for rabies challenge. The challenge material was prepared by a $10^{-4}$ direct dilution of rabies street NYC strain Lot 92-5, supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). All challenged dogs were observed daily for 90 days and the rabies-associated clinical signs and mortality recorded. The brain of each dead or euthanized dog was examined for rabies by fluorescent antibody (FA) test. APHIS/CVB inspectors were on site to observe all procedures for vaccination, challenge material preparation and challenge in this study.

Rabies Vaccine, Live Raccoon Poxvirus Vector was titrated in five replicates with an average titer of 6.28 $Log_{10}TCID_{50}$/mL (per dose). Significant rabies neutralizing antibodies titers were observed in the majority of vaccinated dogs while non-vaccinated dogs remained rabies sero-negative until challenge.

Challenge results demonstrated that 9/10 (90%) controls died due to rabies while 22/25 (88%) vaccinates remained well for a period of 90 days. The brains of the 9 dead control and 3 vaccinate dogs were confirmed as positive for rabies virus by FA testing. There was a significant difference in mortality between the vaccinated and control groups. The vaccine efficacy for prevention of rabies was 87% (95% CI 62, 97). This is a satisfactory test to meet the statutory requirements (Title 9, Code of Federal Regulations) for rabies vaccine efficacy.

Specifically, there were 28 test animals and 13 control animals at the time of vaccination. Thirty-five of these dogs (25 vaccinates and 10 controls) were randomly selected for challenge. Dogs were twelve weeks of age at the time of vaccination. The lyophilized rRCNV-Rabies G2 vaccine that was used for this study was stored at 2-7° C. and consisted of live rRCNV-Rabies G2 and SGGK stabilizer. This recombinant rabies vaccine was adjuvant-free. The test vaccine was titrated in five replicate assays in order to establish the dose administrated into the dogs in this study. The average titer of the vaccine was 6.28 $Log_{10}TCID_{50}$/mL (per dose).

No placebo was used in the control group. Lack of placebo did not introduce any special observation bias, as outcome was live or dead. The outcome was judged by blinded observers more than a full year after vaccination date, at which point any potential temporary effect of lack of placebo would have been long past.

There were 41 experimental units (28 vaccinates and 13 controls) at the time of vaccination. Thirty-five of these dogs (25 vaccinates and 10 controls) were randomly selected for challenge. The animals were randomized according to litter, into vaccinates and controls. The randomization process was completed by random number assignment to the animals of each litter using Microsoft Excel. The random numbers in each litter were sorted in ascending order for the placement of animals from that litter into each group. The process was repeated until animals from all litters had been randomized.

This study was not blinded during the first 3 weeks because vaccinates and controls were housed separately to prevent any potential shedding across groups. Groups had to be known for Animal Care staff to ensure no vaccine carryover across groups. Three-weeks post vaccination, animals were re-randomized and the remainder of the study was blinded.

This was a randomized complete block design. 41 dogs were randomly divided into two groups as follows:

| Group | VACCINE | # OF ANIMALS* |
|---|---|---|
| Vaccinates | rRCNV-Rabies G2 (6.28 $Log_{10}TCID_{50}$/mL/Dose) | 28 |
| Controls | None | 13 |

*25 vaccinates and 10 controls were randomly chosen for rabies challenge.

Vaccination

The lyophilized vaccine was rehydrated by the 1.0 mL sterile water diluent supplied. The vaccination route was subcutaneous. Each animal in the vaccinate group was given one dose (1 mL/dose) of the vaccine in the nape of the neck. The control animals were not vaccinated. APHIS/CVB inspector was on site to observe the whole procedure of vaccination.

Challenge

More than one year (420 days) following the vaccination, 10 controls and 25 vaccinates were chosen for challenge. Four dogs (two vaccinates and two controls) were excluded due to recurring ear infections. Two dogs (one vaccinate and one control) were excluded randomly. The randomization was performed using the random number generator in Microsoft Excel: the vaccinates were assigned numbers, sorted and the highest numbered dogs excluded from the challenge until the number of vaccinates equaled 25; analogous procedure was used to reduce the number of controls to 10. As a result, one control and one vaccinate were randomly excluded from the challenge phase.

All 35 dogs were challenged with a $10^{-4}$ direct dilution of rabies street challenge virus (NYC strain in Fox) supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). Briefly, the animals were tranquilized before the inoculation and then intramuscularly inoculated with 0.5 mL of the diluted challenge into each masseter muscle (total 1.0 mL). The animals were placed and secured in individual cages within the rabies challenge area for the 90-day observation period. APHIS/CVB inspector was on site to observe the whole procedures of challenge virus dilution and rabies challenge.

The lethal challenge dose was determined to be acceptable by the mortality rate of the control dogs in this study. The challenge results indicated that 9/10 (90%) controls died due to rabies. Thus this was a valid challenge test.

No abnormal signs were observed in the 35 healthy dogs for the two days prior to challenge. Serum samples were taken. Six mL of whole blood from each dog was collected for serum at 0 day post vaccination (DPV), 28 DPV, 91 DPV, 182 DPV, 273 DPV and 365 DPV. Serum samples were tested by the Rapid Fluorescent Focus Inhibition Test (RFFIT), a tissue culture fluorescent antibody procedure published by NVSL (National Veterinary Services Laboratories of the United States Department of Agriculture), to determine serum neutralization (SN) titers against rabies virus.

The vaccine used in this study was titrated in five replicates on Vero cells per standard procedures. The average titer of the test vaccine was 6.28 $Log_{10}TCID_{50}$/mL (per dose).

On 28, 91, 182, 273, and 365 days post vaccination, all dogs were bled and individual serum samples tested for neutralizing antibodies to rabies virus by the RFFIT. Rabies neutralizing antibodies titers were observed in the majority of vaccinated dogs while non-vaccinated dogs remained rabies sero-negative until challenge.

Following challenge, dogs were observed daily for 90 days, and rabies-associated clinical signs and death were recorded. 9/10 (90%) non-vaccinated control dogs died or showed rabies signs, indicating that this was a valid challenge test. By contrast, 3/25 (12%) vaccinated dogs died or showed rabies signs. It was found that the death of the dogs due to rabies infection took place between 11 DPC and 17 DPC. At the end of study, 22 vaccinates and one control remained well. There was a significant difference in mortality between vaccinate and control groups. The preventable fraction was 87% (95% CI 62, 97).

The dead and euthanized dogs during the period of post-challenge observations were securely transported to the Veterinary Diagnostic Laboratory at the Iowa State University College of Veterinary Medicine, for fluorescent antibody testing. The brains of the 12 dead dogs (9 controls and three vaccinates) tested positive for rabies virus. These results further confirmed that the death of the 13 dogs was due to rabies.

Conclusion

The results from this one-year DOI study demonstrated that the Rabies Vaccine, Live Raccoon Poxvirus Vector (rRCNV-Rabies G2) is efficacious at a titer of 6.28 $Log_{10}TCID_{50}$/mL (per dose) as an aid in the prevention of rabies for at least one year following a single vaccination of dogs.

Example 11

Reversion to Virulence Study of Rabies Vaccine, Live Raccoon Poxvirus Vector, in Cats The objectives of this study were to determine whether or not rRCNV-Rabies G2 could revert to virulence upon back-passage in cats, and to examine the potential for virus shedding and spreading of the virus among cats.

Reversion to virulence of live recombinant raccoon poxvirus (rRCNV-Rabies G2), which expresses the rabies glycoproteins of Challenge Virus Standard and Pasteur-Paris strains at thymidine kinase and hemagglutination loci, respectively, was evaluated in this study. The initial passage and confirmatory back-passage were conducted in a total of 35 healthy cats eight weeks of age. All 35 cats were serologically negative for raccoon poxvirus at the time of inoculation.

The initial passage was conducted in a total of 15 cats: 10 cats inoculated orally with a 1.0 mL dose of 7.41 $Log_{10}TCID_{50}$ rRCNV-Rabies G2, and 5 cats as contact controls with no inoculation. Oral swabs and five random fecal samples were collected daily from −2 to 15 days post inoculation (DPI). At 15 DPI all cats were necropsied for tissue sample collection. No gross lesion was observed, and no virus was isolated from any of oral swabs, fecal and tissue samples.

To ensure accuracy, a confirmatory back-passage was preformed in 20 cats: 10 cats inoculated orally with a 1.0 mL dose of the same virus (7.57 $Log_{10}TCID_{50}$) as in the initial passage, and 10 cats inoculated orally with a 1.0 mL dose of the pooled tissue homogenate collected from the initial passage. Oral swabs and five random fecal samples were taken daily from −2 to 21 DPI. At 21 DPI all cats were necropsied for tissue sample collection. As in the initial passage, no gross lesion was observed, and no virus was isolated from any of the collected samples.

In both passages, all cats were monitored daily for rectal temperatures, clinical signs associated with infection of raccoon poxvirus, and any other local or systemic reactions during study period. None of the tested cats showed any of the clinical signs associated with infection of raccoon poxvirus, or significant rectal temperature elevation.

In summary, the results from this study demonstrated that rRCNV-Rabies G2 could not revert to virulence and/or disseminate into body fluids or feces when passed in cats. In addition, none of the tested cats developed clinical signs. These results further indicated that rRCNV-Rabies G2 is non-replicative and non-pathogenic in cats.

Virus shedding was not demonstrated following inoculation with a high level of live RCNV, confirming that RCNV is non-replicative and non-pathogenic in cats.

Specifically, a total of 35 healthy cats were used for this study. The initial passage used 10 inoculated cats and 5 untreated (contact) control cats. The confirmatory passage used 20 cats, in which 10 cats were inoculated with the pooled tissue homogenate from the initial passage, and 10 cats were inoculated with the same virus as the initial passage.

Cats were approximately eight weeks of age at the time of inoculation in both passages. The target population was healthy cats. With respect to their immune function, the animals selected for this study were deemed as representative of cats. All cats tested negative to RCNV (SN titer <2).

The initial passage consisted of 15 cats, 10 inoculated with rRCNV-Rabies G2 x+3 and 5 untreated contact controls. The confirmatory back-passage included 20 cats. Ten cats were inoculated with the pooled tissue homogenate from the initial passage, and 10 cats were inoculated with the same virus (rRCNV-Rabies G2 x+3) as in the initial passage.

The cats used for the initial inoculation and confirmatory back-passage were randomized into the appropriate groups by litter. Randomization was completed by the assignment of random numbers to the animals of each litter using Microsoft Excel. The random number was sorted in ascending order to place the animals of each litter into their respective groups. The study was blinded to the scientists performing the observations, sample collection and testing for the initial passage and confirmatory back-passage of the study.

Initial Passage

Ten inoculated cats were gang housed with five untreated (contact) control cats to evaluate the ability of the vaccine virus to spread by animal-to-animal contact. Oral swabs and fecal samples were collected daily from −2 to 15 days post inoculation (DPI). Rectal temperatures and observations for general health and clinical signs were monitored daily from −2 to 15 DPI.

At 15 DPI, the 10 inoculated and the 5 contact control cats were euthanized and necropsied. Tissue samples (cervical lymph node, liver, spleen and tonsil) were collected aseptically for virus isolation.

Confirmatory Back-Passage

Since no virus was isolated from the oral swabs, fecal samples, or tissue samples in the initial passage, a confirmatory back-passage was conducted using 20 cats. Ten cats were inoculated with the pooled tissue homogenate and 10 cats were inoculated with the virus as in initial inoculation. These cats were observed from −2 DPI to 21 DPI. The cats were euthanized and necropsied at 21 DPI.

Inoculation

All cats except contact controls (no inoculation) were administered orally with a 1.0 mL dosage volume in both initial and confirmatory back-passages.

Observation and Procedure

Rectal temperatures, and clinical signs such as coughing, sneezing, nasal and ocular discharge, glossitis, and stomatitis were monitored daily from −2 to 15 DPI for initial passage, and −2 to 21 DPI for the confirmatory back-passage. Serum samples, oral swabs, fecal samples and tissue samples after necropsy were collected and analyzed.

Antibody to RCNV was measured by serum neutralization using a constant virus (50-300 $TCID_{50}$) varying serum method. Endpoints were read by microscopic examination for cytopathic effect (CPE) characteristic of RCNV infection on Vero cells. Titers were calculated as the serum dilution causing 50% inhibition of virus replication according to the method of Reed and Muench.

The rRCNV-Rabies G2 inoculum used in the initial and confirmatory back-passages was titrated on Vero cells in a 24-well plate.

Briefly, serial ten-fold dilutions were made for rRCNV-Rabies G2 using 1×MEM containing 0.05% LAH and gentamicin (30 µg/mL). 100 µL of diluted virus per well were inoculated on a more than 90% confluent monolayer. Plates were incubated at 36±2° C. with 4-6% $CO_2$ for 2 hours. Following the incubation, 1.0-1.5 mL of 1×MEM containing 0.05% LAH, gentamicin (30 µg/mL) and 5% FBS was added into each well, and plates further incubated at 36±2° C. with 4-6% $CO_2$ for 5 days. After incubation, plates were stained for observation of the typical CPE or plaques. $TCID_{50}$ titers were calculated using Reed and Muench method.

To determine the sensitivity of virus isolation method, rRCNV-Rabies G2 was diluted (spiked) in the pooled oral swabs, tissue homogenate and fecal samples, and titrated by above described method.

To demonstrate a lack of reversion to virulence of the rRCNV-Rabies G2 when passed in the cats, the following criteria should be met:

a) Cats inoculated with rRCNV-Rabies G2 should show no signs of clinical disease. Mild and transient clinical abnormalities such as faucitis are expected for oral administration of modified live virus and should be considered normal reactions of inoculation.

b) No phenotypic and/or genotypic changes are observed in the rRCNV-Rabies G2 isolated from the confirmatory backpassage as compared to the virus inoculated in the initial passage.

c) There is no virus shedding and spreading if no virus is isolated from the fecal, oral and tissue samples.

Titration of the inoculum rRCNV-Rabies G2 x+3 was conducted in five replicates. The average titer for the initial passage was 7.41 $Log_{10}TCID_{50}$/mL, and 7.57 $Log_{10}TCID_{50}$/mL for the confirmatory back-passage. These titers were approximately 13-20 times higher than the regular dose (6.28

$Log_{10}TCID_{50}/mL$) administered to cats and dogs in the One-Year Duration of Immunity Studies.

Antibody to RCNV was measured by serum neutralization to confirm that cats were negative for RCNV antibodies. The serum neutralization assay showed that all cats were negative (SN<2) for RCNV antibody at the time of inoculation in both passages.

The rectal temperatures and clinical signs for all cats were recorded as normal in the initial passage and the confirmatory back-passage. Some of the cats in both the controls and inoculated groups occasionally had elevated temperatures (103.0° F. to 103.9° F.), and this is most likely due to the cats becoming excited during the observation times and while being restrained. There were no abnormal signs observed during the study period. At 15 DPI (initial passage) and 21 DPI (confirmatory back-passage), all cats were necropsied and no gross lesions were observed. These results indicated that rRCNV-Rabies G2 is non-pathogenic for cats.

Viral isolation from all oral swabs, fecal and tissue samples was negative for initial passage and confirmatory back-passage. The virus titer was not calculated since no virus was isolated from any passage. These results indicated that rRCNV-Rabies G2 is non-replicative in cats.

To examine if the oral swabs, fecal and tissue samples have any negative impact on virus titration, rRCNV-Rabies G2 x+3 was titrated in duplicate using the above samples as diluent, and compared with MEM medium as a control. The average titer of rRCNV-Rabies G2 x+3 was 7.6 (oral swabs), 7.0 (fecal), 7.0 (tissue), and 7.6 $Log_{10}TCID_{50}/mL$ (MEM), respectively. These results indicated no significant impact of oral swabs, fecal and tissue samples on the titration assay. Further spiking test for sensitivity indicated that the isolation would be positive if there were viral particles in the test samples.

Since no virus was isolated from any of the test samples, the comparison of the rRCNV-Rabies G2 phenotypic and/or genotypic changes between initial passage and confirmatory back-passage was not conducted.

Conclusion

The results from this study indicated that rRCNV-Rabies G2 is unable to revert to virulence when passed in cats. It is also demonstrated that the rRCNV-Rabies G2 virus did not shed or disseminate among the cats.

Example 12

Dose Titration of Inactivated rRCNV-Rabies G2 Fraction in Combination with DURAMUNE® DA2PPv or DURAMUNE® DA2PPv/CvK/LCIGP in Dogs Briefly, in this dose titration study, there were four groups: Dogs (n=3×10) in the three vaccinate groups were administrated a single-dose of DURAMUNE® DA2PPv (Cake)/Inactivated rRCNV-Rabies G2 with 6.7 or 6.4 $Log_{10}TCID_{50}/mL$ pre-inactivation titer (Diluent), or CvK/LCIGP/Inactivated rRCNV-rabies G2 with 6.7 $Log_{10}TCID_{50}/mL$ pre-inactivation titer (Diluent), respectively, at 12 weeks of age, and dogs (n=10) in the control group were vaccinated with DURAMUNE® DA2PPv (Cake)/Water (Diluent). At the time of vaccination, all test dogs were rabies sero-negative.

Twenty weeks following the vaccination (at 140 DPV), all dogs (30 vaccinates and 10 controls) were challenged with a 1:$10^{-5}$ direct dilution of rabies street NYC strain, supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). All challenged dogs were observed daily for 33 days, and the rabies-associated clinical signs and mortality recorded. Challenge results demonstrated that 10/10 (100%) controls died due to rabies while 9/10 (90%) vaccinates in Group 1, 10/10 (100%) vaccinates in Group 2, and 10/10 (100%) vaccinates in Group 3 remained well for a period of 33 days, respectively. There was a significant difference in mortality between the vaccinated and control groups. The vaccine efficacy was 90% (V1), 100% (V2) and 100% (V3), respectively.

DURAMUNE® 10 combination product (commercially available from Fort Dodge Animal Health, a division of Wyeth, Madison, N.J.), Canine Distemper—Adenovirus Type 2—Coronavirus—Parainfluenza—Parvovirus Vaccine, Modified Live and Killed Virus, *Leptospira* Bacterin (DA2PPv/CvK/LCIGP) is an USDA licensed vaccine. The lyophilized DAPPv modified live fraction contains canine distemper virus (CDV), canine adenovirus Type 2 (CAV2), canine parainfluenza virus (CPI), and canine parvovirus (CPV). The diluent CvK/LCIGP fraction contains inactivated canine coronavirus (CCV) and *leptospira* bacterin (L) consisting of the outer membrane proteins (OMC) of *Leptospira icterohaemorrhagiae, Leptospira canicola, Leptospira grippotyphosa*, and *Leptospira pomona*. The DA2PPv cake is reconstituted with the CvK/LCIGP diluent and administered by the subcutaneous (SQ) route to puppies six weeks of age or older as an aid to protect against diseases caused by CDV, infectious canine hepatitis virus (ICHV), CAV2, CPV, CPI, CCV, *L. canicola, L. icterohaemorrhagiae, L. grippotyphosa*, and *L. pomona*.

In this dose titration study, dogs were vaccinated with a single dose of DURAMUNE® DA2PPv/Inactivated rRCNV-Rabies G2 or DURAMUNE® DA2PPi/CvK/LCIGP/Inactivated rRCNV-Rabies G2, and challenged with virulent rabies virus about 5 months following the vaccination. The objectives of this study were: (1) to determine whether the recombinant virus (rRCNV-Rabies G2) is immunogenic as an inactivated vaccine; (2) to evaluate 5 month DOI of inactivated rRCNV-rabies G2 in combination with DA2PPv or DURAMUNE® DA2PPi, and (3) to optimize the dosage for immunogenicity.

There were 30 test animals and 10 control animals. Dogs were twelve weeks of age at the time of vaccination.

Composition of Test Vaccines

Vaccine 1 (V1) consisted of lyophilized DA2PPv cake and Diluent 1. Diluent 1 contained inactivated rRCNV rabies G2 fraction (approximately 6.7 $Log_{10}TCID_{50}$ pre-inactivation titer per dose) and adjuvant (1% EMA and 3% NEOCRYL®).

Vaccine 2 (V2) consisted of lyophilized DA2PPv cake and Diluent 2. Diluent 2 contained inactivated rRCNV rabies G2 fraction (approximately 6.4 $Log_{10}TCID_{50}$ pre-inactivation titer per dose) and adjuvant (1% EMA and 3% NEOCRYL®).

Vaccine 3 (V3) consisted of lyophilized DAPPv cake and Diluent 3. Diluent 3 contained inactivated rRCNV rabies G2 fraction (approximately 6.7 $Log_{10}TCID_{50}$ pre-inactivation titer per dose), inactivated canine coronavirus (CvK), *Leptospira* bacterin (LCIGP—the OMC of *Leptospira icterohaemorrhagiae, Leptospira canicola, Leptospira grippotyphosa*, and *Leptospira pomona*), and adjuvant (1% EMA® and 3% NEOCRYL®).

The lyophilized DA2PPv fraction and the CvK/LCIGP diluent were produced according to conventional manufacturing methods. The Inactivated rRCNV-Rabies G2 fraction was inactivated by BEI (binary ethyleneimine) by standard techniques for inactivating virus cultures for vaccine preparation. The lyophilized DA2PPv fraction was rehydrated by respective diluent at the time of vaccination. In this study, the DURAMUNE® DA2PPv cake was reconstituted with 1 mL of sterile Super Q water, and the rehydrated DA2PPv was used as a placebo.

Methods

The dogs were randomly divided into 4 groups as follows:

| Group | VACCINE | | # OF ANIMALS |
|---|---|---|---|
| | MLV-CAKE | INACTIVATED-DILUENT | |
| 1 | DA2PPv | Inactivated rRCNV-Rabies G2 (6.7 $Log_{10}TCID_{50}$ per dose) | 10 |
| 2 | DA2PPv | Inactivated rRCNV-Rabies G2 (6.4 $Log_{10}TCID_{50}$ per dose) | 10 |
| 3 | DA2PPv | CvK/LCIGP + Inactivated rRCNV-Rabies G2 (6.7 $Log_{10}TCID_{50}$ per dose) | 10 |
| 4 | DA2PPv | SQ water | 10 |

*CvK/LCIGP fraction: inactivated canine coronavirus (CvK) and *leptospira* bacterin (L) consisting of the OMC of *Leptospira icterohaemorrhagiae*, *Leptospira canicola*, *Leptospira grippotyphosa*, and *Leptospira pomona* at the release levels.

Vaccination

The vaccination route was subcutaneous (SQ). Each animal was given one dose (1 mL/dose) of the vaccine/placebo in the nape of the neck.

Challenge

Twenty weeks (about 5 months) following the vaccination, all dogs were challenged with a 1: $10^{-5}$ direct dilution of rabies street challenge virus (NYC strain in Fox) supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). Briefly, the animals were tranquilized before the inoculation and then intramuscularly inoculated with 0.5 mL of the diluted challenge into each masseter muscle (total 1.0 mL). The animals were placed and secured in individual cages within the rabies challenge area for the 33-day observation period. The 33-day post challenge observation period was justified by previous rabies challenge results that all rabid animals died in the first 4 weeks post challenge.

The lethal challenge dose was determined to be acceptable by the mortality rate of the control dogs in this study. The challenge results indicated that 10/10 (100%) controls died due to rabies. This was obviously a valid challenge test.

Observation

No abnormal signs were observed in the 40 healthy dogs for the two days prior to challenge.

After challenge, the animals were monitored daily by personnel trained by clinical Veterinarians to recognize signs of rabies until 33 days post challenge (DPC). The observation were recorded and graded as per statutory requirements for rabies vaccines.

Following challenge, dogs were observed daily for 33 days, and rabies-associated clinical signs and death were recorded. 10/10 (100%) control dogs died or showed rabies signs, indicating that this was a valid challenge test. By contrast, 9/10 (90%), 10/10 (100%), and 10/10 (100%) vaccinates in Group 1, 2, or 3 remained well for a period of 33 days, respectively. It was interestedly found that the death of 11 dogs due to rabies infection took place between 11 DPC and 22 DPC. There was a significant difference in mortality between the vaccinated and control groups, The vaccine efficacy was 90% (V1), 100% (V2) and 100% (V3), respectively.

Conclusion

The results from this dose titration study demonstrate that the inactivated rRCNV-rabies G2 fraction of the present invention combined with DURAMUNE® DA2PPv or DURAMUNE® DAP2Pv/CvK/LCIGP is efficacious even at a pre-inactivation titer of 6.4 $Log_{10}TCID_{50}$/mL (per dose), as an aid in the prevention of rabies for at least 5 months following a single vaccination, in dogs.

Example 13

Three-year Duration of Immunity Study of Rabies Vaccine (Regular Dose), Live Raccoon Poxvirus Vector, in Cats To determine the protective dose for use of the vaccine product in cats, a three-year duration of immunity (DOI) study of rRCNV-Rabies G2 vaccine was conducted using materials and methods similar to those described previously in Example 9, and the efficacy was demonstrated by virulent rabies virus challenge. The objective of this study was to demonstrate the efficacy and the immunogenicity of the adjuvant-free recombinant rabies vaccine in cats after a three-year duration following a single vaccination, using a dose of 6.28 $Log_{10}TCID_{50}$/ml.

Briefly, in this one-year duration of immunity (DOI) study, there were two groups: cats (n=28) in the vaccinate group were administrated a single-dose of Rabies Vaccine, Live Raccoon Poxvirus Vector (VS Code 1901.R5) at 12 weeks of age, and cats (n=13) in the control group were not vaccinated. On 0, 28, 91, 181, 273, 365, 549, 730, 912, and 1095 days post vaccination, all cats were bled and individual serum samples tested for neutralizing antibodies to rabies virus as described previously. More than three years (1128 days) following the vaccination, 35 cats (25 vaccinates and 10 controls) were randomly chosen for rabies challenge. The challenge material was prepared by a 1:25 direct dilution of rabies street NYC strain Lot 92-5, supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). All challenged cats were observed daily for 90 days and the rabies-associated clinical signs and mortality recorded. The brain of each dead or euthanized cat was examined for rabies by fluorescent antibody (FA) test. APHIS/CVB inspectors were on site to observe all procedures for vaccination, challenge material preparation and challenge in this study.

The Rabies Vaccine, Live Raccoon Poxvirus Vector was titrated in five replicates with an average titer of 6.28 $Log_{10}TCID_{50}$/mL (per dose). Significant rabies neutralizing antibodies titers were observed in the vaccinated cats while non-vaccinated cats remained rabies sero-negative until challenge.

Challenge results demonstrated that 10/10 (100%) controls died due to rabies while 21/25 (84%) vaccinates remained well for a period of 90 days. The brains of the 10 dead controls and 4 dead vaccinated cats were confirmed as positive for rabies virus by FA testing. There was a significant difference in mortality between the vaccinated and control groups. The vaccine efficacy for prevention of rabies was 84% (95% CI 64, 96).

Example 14

One-year Duration of Immunity Study of Rabies Vaccine (Regular Dose), Live Raccoon Poxvirus Vector Combined with Fel-O-Vax-LvK IV+CaliciVax, in Cats To determine the protective dose for use of the vaccine product in cats, a one-year duration of immunity (DOI) study of rRCNV-Rabies G2 fraction was conducted, and the efficacy was demonstrated by virulent rabies virus challenge. The objective of this study was to demonstrate the efficacy and the immunogenicity of the rRCNV-Rabies G2 fraction in combination with Fel-O-Vax-LvK IV+CaliciVax in cats after a one-year duration.

Briefly, in this one-year duration of immunity (DOI) study, there were two groups: cats (n=28) in the vaccinate group were administrated subcutaneously 1 mL of Rabies Vaccine, Live Raccoon Poxvirus Vector (cake) combined with Fel-O-Vax LvK IV+Calici Vax (diluent) at 12 weeks of age, and cats (n=13) in the control group were administrated subcutaneously 1 mL of Fel-O-Vax LvK IV+Calici Vax (diluent). At 8 weeks of age all cats were given 1 mL of Fel-O-Vax LvK IV+Calici Vax. On 0, 28, 91, 182, 274, and 398 days post vaccination, all cats were bled and individual serum samples tested for neutralizing antibodies to rabies virus. More than one year (400 days) following the vaccination, 35 cats (25 vaccinates and 10 controls) were randomly chosen for rabies challenge. The challenge material was prepared by a 1:25 direct dilution of rabies street NYC strain Lot 92-5, supplied by the NVSL-BVL, USDA (National Veterinary Services Laboratories of the United States Department of Agriculture and Berrimah Veterinary Laboratories of the Northern Territory of Australia under the National Association of Testing Authorities (NATA) quality accredited laboratories). All challenged cats were observed daily for 90 days and the rabies-associated clinical signs and mortality recorded. The brain of each dead or euthanized cat was examined for rabies by fluorescent antibody (FA) test. APHIS/CVB inspectors were on site to observe all procedures for vaccination, challenge material preparation and challenge in this study.

The Rabies Vaccine, Live Raccoon Poxvirus Vector was titrated in five replicates with an average titer of 6.28 $Log_{10}TCID_{50}$/mL (per dose). Significant rabies neutralizing antibodies titers were observed in the vaccinated cats while non-vaccinated cats remained rabies sero-negative until challenge.

Challenge results demonstrated that 7/10 (70%) controls died due to rabies while 25/25 (100%) vaccinates remained well for a period of 90 days. The brains of the 7 dead control cats were confirmed as positive for rabies virus by FA testing. There was a significant difference in mortality between the vaccinated and control groups. The vaccine efficacy for prevention of rabies was 100% (95% CI 82, 100).

In the foregoing, there has been provided a detailed description of particular embodiments of the present invention for purpose of illustration and not limitation. It is to be understood that all other modifications, ramifications and equivalents obvious to those having skill in the art based on this disclosure are intended to be included within the scope of the invention as claimed.

SEQUENCE DESCRIPTION AND IDENTIFIERS

| Sequence Identifier | Description |
| --- | --- |
| 1 | Complete sequence of plasmid pFD2003SEL-GPV-PV |
| 2 | HA-08 primer |
| 3 | HA-Pst: primer |
| 4 | gp-1F primer |
| 5 | TK-LW primer |
| 6 | TK-RW primer |
| 7 | TK-RR primer |
| 8 | gJE-F1 primer |
| 9 | PW-04 primer |
| 10 | PW-03 primer |
| 11 | Rabies virus G protein |
| 12 | LacZ ORF |
| 13 | Ampicillin ORF |

---

What is claimed is:

1. A recombinant raccoon poxvirus vector (rRCNV) comprising two or more exogenous nucleic acid molecules, each encoding a rabies virus glycoprotein from different strains of the rabies virus, wherein at least two of the nucleic acid molecules are inserted into: (a) the hemagglutinin (ha) locus, or (b) the thymidine kinase (tk) locus, or (c) the hemagglutinin and thymidine kinase loci.

2. The recombinant raccoon poxvirus vector according to claim 1, wherein a source of rabies virus glycoprotein is selected from the group consisting of a Challenge Virus Standard rabies strain, a Pasteur-Paris rabies strain, a canine rabies street virus, an Arctic Fox rabies virus, a raccoon rabies virus and a bat rabies virus.

3. The recombinant raccoon poxvirus vector according to claim 2, wherein the nucleic acid molecule encoding the glycoprotein that is inserted at the thymidine kinase locus of the raccoon poxvirus genome is from the Challenge Virus Standard rabies strain.

4. The recombinant raccoon poxvirus vector according to claim 2, wherein the nucleic acid molecule encoding the glycoprotein that is inserted at the hemagglutinin locus of the raccoon poxvirus genome is from the Pasteur-Paris rabies strain.

5. The recombinant raccoon poxvirus vector according to claim 1, wherein the raccoon poxvirus is live and replicable.

6. The recombinant raccoon poxvirus vector according to claim 5, further comprising a nucleic acid molecule encoding a rabies virus glycoprotein that is inserted into a third non-essential site of the raccoon poxvirus genome in addition to the thymidine kinase and the hemagglutinin loci of the raccoon poxvirus genome.

7. The recombinant raccoon poxvirus vector of claim 6, wherein the third non-essential site of the raccoon poxvirus genome is the serine protease inhibitor site.

8. A recombinant rabies vaccine comprising an immunologically effective amount of the recombinant raccoon poxvirus vector of claim 1 and, optionally, a suitable carrier or diluent.

9. The recombinant rabies vaccine according to claim 8, further comprising a mixture with one or more feline pathogen antigens selected from the group consisting of feline calicivirus, *Chlamydophila felis*, feline leukemia virus, feline panleukopenia virus, feline rhinotracheitis virus, feline immunodeficiency virus, feline infectious peritonitis virus and *Bartonella bacteria*.

10. The recombinant rabies vaccine according to claim 8, further comprising a mixture with one or more canine pathogen antigens selected from the group consisting of *Ehrlichia canis*, canine parvovirus, canine distemper, canine parainfluenza virus, canine adenovirus type II, canine adenovirus, canine coronavirus, *Leptospira icterohemorrhagiae*, *Leptospira canicola*, *Leptospira grippotyphosa* and *Leptospira pomona*.

11. The recombinant rabies vaccine according to claim 8, further comprising an adjuvant.

12. The recombinant rabies vaccine according to claim 11, wherein the adjuvant comprises a mixture of an ethylene/maleic copolymer and an acrylic acid copolymer emulsion.

13. The recombinant rabies vaccine according to claim 9, further comprising an adjuvant.

14. The recombinant rabies vaccine according to claim 13, wherein the adjuvant comprises a mixture of an ethylene/maleic copolymer and an acrylic acid copolymer emulsion.

15. The recombinant rabies vaccine according to claim 10, further comprising an adjuvant.

16. The recombinant rabies vaccine according to claim 15, wherein the adjuvant comprises a mixture of an ethylene/maleic copolymer and an acrylic acid copolymer emulsion.

17. A method for inducing a protective immune response to rabies in a mammal comprising administering to the mammal an effective immunizing amount of the vaccine of claim 8.

18. A method for inducing a protective immune response to rabies in a mammal comprising administering to the mammal an effective immunizing amount of the vaccine of claim 11.

19. A method for inducing a protective immune response to rabies in a cat which comprises administering to the cat an effective immunizing amount of the vaccine of claim 9.

20. A method for inducing a protective immune response to rabies in a dog which comprises administering to the dog an effective immunizing amount of the vaccine of claim 10.

21. A method of making a recombinant raccoon poxvirus vector, comprising the following steps:(a) inserting a nucleic acid sequence encoding a glycoprotein of a first rabies strain into the thymidine kinase locus of the raccoon poxvirus genome;(b) inserting a nucleic acid sequence encoding a glycoprotein of a second rabies strain into the hemagglutinin locus of the raccoon poxvirus genome; and(c) recovering the recombinant raccoon poxvirus vector.

22. The method according to claim 21, wherein the nucleic acid sequences of steps (a) and (b) further comprise a promoter sequence operably linked to the nucleic acid sequences to allow expression of the nucleic acid and production of the glycoprotein of the first and second rabies strains by the recombinant raccoon poxvirus vector.

23. The method of claim 21, wherein the first rabies strain is a Challenge Virus Standard rabies strain.

24. The method of claim 21 wherein the second rabies strain is a Pasteur-Paris rabies strain.

25. The method of claim 17, wherein the effective immunizing amount of the vaccine ranges from about 4.5 $Log_{10}TCID_{50}$/ml to about 6.7 $Log_{10}TCID_{50}$/ml.

26. The method of claim 17, wherein the effective immunizing amount of the vaccine ranges from about 5.38 $Log_{10}TCID_{50}$/ml to about 6.28 $Log_{10}TCID_{50}$/ml.

27. The method of claim 17, wherein the vaccine is administered as a single dose or as repeated doses.

28. The recombinant rabies vaccine of claim 8, wherein the vaccine is adjuvant-free.

\* \* \* \* \*